US012721621B1

(12) United States Patent
Bogran

(10) Patent No.: US 12,721,621 B1
(45) Date of Patent: Sep. 1, 2026

(54) HANDHELD MEDICAL SUTURING DEVICE

(71) Applicant: Luis Bogran, Kenner, LA (US)

(72) Inventor: Luis Bogran, Kenner, LA (US)

(*) Notice: Subject to any disclaimer, the term of this patent is extended or adjusted under 35 U.S.C. 154(b) by 581 days.

(21) Appl. No.: 17/834,816

(22) Filed: Jun. 7, 2022

Related U.S. Application Data

(60) Provisional application No. 63/326,216, filed on Mar. 31, 2022.

(51) Int. Cl.
*A61B 17/04* (2006.01)

(52) U.S. Cl.
CPC ...... *A61B 17/0491* (2013.01); *A61B 17/0482* (2013.01); *A61B 2017/0488* (2013.01); *A61B 2017/0496* (2013.01)

(58) Field of Classification Search
CPC . A61B 17/0491; A61B 17/0482; A61B 17/06; A61B 2017/0488; A61B 2017/0496
See application file for complete search history.

(56) References Cited

U.S. PATENT DOCUMENTS

| | | | |
|---|---|---|---|
| 4,417,532 A | 11/1983 | Yasukata | |
| 4,557,265 A | 12/1985 | Anderson | |
| 4,899,746 A | 2/1990 | Brunk | |
| 5,364,408 A | 11/1994 | Gordon | |
| 5,458,609 A | 10/1995 | Gordon et al. | |
| 5,540,704 A | 7/1996 | Gordon et al. | |
| 5,578,044 A | 11/1996 | Gordon et al. | |
| 6,641,592 B1 | 11/2003 | Sauer et al. | |
| 8,628,545 B2 | 1/2014 | Cabrera et al. | |
| 9,125,645 B1 * | 9/2015 | Martin ............... | A61B 17/0469 |
| 9,386,980 B2 | 7/2016 | Smith | |
| 9,554,793 B2 | 1/2017 | Lane et al. | |
| 2002/0173800 A1 * | 11/2002 | Dreyfuss ............ | A61B 17/0057 606/139 |
| 2006/0224184 A1 | 10/2006 | Stefanchik et al. | |

(Continued)

OTHER PUBLICATIONS

Gurusamy KS, Toon CD, Allen VB, Davidson BR, Continuous versus interrupted skin sutures for non-obstetric surgery, Cochrane Database Syst Rev. Feb. 14, 2014, https://pubmed.ncbi.nlm.nih.gov/24526375/.

(Continued)

*Primary Examiner* — Brooke Labranche
(74) *Attorney, Agent, or Firm* — Kilpatrick Townsend & Stockton LLP

(57) ABSTRACT

The present disclosure provides for a handheld medical suturing device having a handle body with a hinge operatively connected to a handle lever. At a distal end of the handle lever is an actuating arm operatively connected to a bent constrained rigid body, which is operatively connected to a pivoting radial arm. The pivoting radial arm is operatively connected to a curved suturing needle assembly which actuates suture through a tissue upon a user's pivoting of the handle lever relative to the handle body. A bobbin containing suture is disposed in a bobbin carrier, which is engagingly fitted within a fixed bobbin channel that is positioned within the handle body. At least a first thumb lever is fixed to an axle having a mutilated spur gear that engages a rack on the bottom of the bobbin carrier, such a rotation of the at least first thumb lever moves the bobbin and suture side to side within the bobbin carrier through a bow to form a knot of suture through the tissue.

23 Claims, 42 Drawing Sheets

(56) References Cited

U.S. PATENT DOCUMENTS

| | | | | |
|---|---|---|---|---|
| 2010/0042116 | A1 | 2/2010 | Chui et al. | |
| 2016/0243343 | A1* | 8/2016 | Miller | A61M 25/104 |
| 2020/0291562 | A1* | 9/2020 | Asami | D05B 57/26 |
| 2020/0383679 | A1* | 12/2020 | Alfia | A61B 17/0401 |

OTHER PUBLICATIONS

Leif A. Israelsson, M.D., PHD, Daniel Millbourn, MD, PHD, Prevention of Incisional Hernias, How to Cloase a Midline Incision, www.surgical.theclinics.com, 2013.

* cited by examiner 224
222
174
192
190
164
218
182
180
214
142d
168
152
216
194
178
142
D
220
172
226
136
196
198
160
156
158
Y
X
159
E
166
162

HANDHELD MEDICAL SUTURING DEVICE

CROSS-REFERENCE TO RELATED APPLICATIONS

This application claims the benefit of priority of U.S. Provisional Application No. 63/326,216, filed Mar. 31, 2022, the disclosure of which is hereby incorporated herein by reference in its entirety.

BACKGROUND OF THE INVENTION

Field of the Invention

The present invention generally relates to a suturing instrument for joining two edges of biological tissue together and more particularly relates to a handheld medical suturing device for joining two edges of biological tissue together with a curved needle and tying knots or locking sutures.

Description of the Related Art

People around the world encounter lacerations and other broken tissues in need of medical suturing (stitching). During operations, surgeons make a cut (incision) in the skin to gain access to the surgical site, or an incision already exists due to a injury. Incisions are closed with sutures (stitches), staples, tissue adhesives or tapes. One of the problems inherent in many surgical procedures is that of limited access of the surgeon's hands, as well as the needle and suturing implements, into the incision or wound. In performing surgical procedures, surgeons often rely on existing methods of manually suturing and tying knots that are slow, time consuming and tedious. In conventional methods, a patient's wounds can be left open longer than desired, which increases the risk of infection or other complications. It is well known that impaired wound healing increases costs of health care and leads to poor cosmetic results (Continuous versus interrupted skin sutures for non-obstetric surgery, Gurusamy KS, Toon CD, Allen VB, Davidson BR, Cochrane Database Syst Rev. 2014 Feb. 14). Also, existing methods and devices further can cause fatigue and repetitive physical strain ailments or injuries for surgeons when manually manipulating existing tools to suture wounds and tie knots.

These problems are amplified under circumstances where delicate surgery such as heart, brain, and spinal surgery, as well as surgery on infants and children is undertaken, since the surgical areas of interest involve minute features. Such conventional methods include the use of tools such as small curved needles, needle drivers, tweezers, and clamps to secure sutures and close external wounds. Many surgical procedures that would otherwise be possible on adults and children are impossible due to the tiny operating fields, and many conditions that might otherwise be corrected by surgery are, therefore, considered to be inoperable. The same situation occurs under circumstances such as suturing within interior and normally inaccessible areas of the body where no known surgical techniques and/or instruments can access these areas and provide the necessary surgical relief.

Moreover, incisional ventral hernias are the most common complication after a laparotomy (open abdomen surgery) and are the most common indication for reoperation after laparotomy, but roughly half of these hernias are preventable if better suturing techniques are implemented, including smaller sutures that are more closely placed together. More than 150,000 patients a year undergo incisional ventral hernia repair in the United States alone, at an approximate cost of one billion dollars. Studies of the effects of changes to our usual method of closing abdominal surgical wounds by using the techniques for continuous suturing of midline abdominal wound incisions proposed by Leif Israelsson et al. have shown that smaller sutures (6 mm to 8 mm from the fascial wound edge) that are more closely placed together to yield a suture-to-wound length ratio of 4:1 or greater cut the incidence of incisional hernias by half. This has been verified by subsequent studies and indicates that about half the incisional hernias are preventable when surgeons implement smaller sutures that are more closely placed together and would save much patient suffering and as much as half a billion dollars a year in surgical expenses. Thus, a need exists for new medical devices and methods for placing sutures more closely together.

Various devices and methods have been discovered over the years for suturing and other surgical techniques, such as those disclosed in U.S. Pat. No. 4,417,532 to Yasukata, U.S. Pat. No. 4,557,265 to Anderson, U.S. Pat. No. 4,899,746 to Brunk, U.S. Pat. No. 5,364,408 to Gordon, U.S. Pat. No. 5,458,609 to Gordon et al, U.S. Pat. No. 5,540,704 to Gordon et al., U.S. Pat. No. 5,578,044 to Gordon et al., U.S. Pat. No. 6,641,592 to Sauer et al., U.S. Patent Publication No. 2010/0042116 to Chui et al., U.S. Pat. No. 8,628,545 to Cabrera et al., U.S. Pat. No. 9,386,980 to Smith, and U.S. Pat. No. 9,554,793 to Lane et al. While these units may be suitable for the particular purpose employed, they would not be as suitable, efficient, and safe for the purposes and achievements of the present invention as disclosed hereafter.

Consequently, one object of the present invention is to provide a suturing apparatus that can be used readily, even in cases of laparoscopy surgery, and which sews a suture by threading a suture material through a patient's tissue and also ties a knot or locks the suture at intervals when suturing the tissues together, both with respect to a single surgical stitch and a row of such stitches.

It therefore can be seen that a need exists for new surgical devices and methods that address the foregoing and other related and unrelated problems in the art.

A need exists for medical suturing devices that will help insert the suturing materials through tissues while alleviating or obviating the fatigue otherwise associated with manually suturing and tying knots. A need exists for new and improved medical suturing devices of comparatively simple construction and arrangement, and where the medical suturing devices are strong, durable, and efficient in its use.

As disclosed in this application, the inventor has discovered novel and unique medical devices and methods for suturing tissues and fabrics, which exhibit superlative properties without being dependent on manual, immobile, components.

The devices and methods disclosed herein avoid many of the drawbacks of existing methods and devices which rely on expensive complexities or complex tools for application of the suturing materials to tissue or fabrics.

Embodiments of the present invention provide for improved medical suturing devices and methods as described and defined in the description below and in the annexed claims which provide for improved suturing and knot tying operation characteristics with reduced fatigue in order to efficiently suture a patient's tissue or intended fabrics. Each patent application identified above is incorporated here by reference in its entirety.

SUMMARY OF THE INVENTION

It is one prospect of the present invention to provide novel medical suturing devices and methods of simple but effective construction and operation which can be applied to varying sizes of tissue lacerations and other openings to securely suture or bind tissues in an efficient and effective manner.

Further objects of the invention are to provide medical suturing devices and processes which are comparatively simple in its construction and arrangement, strong, durable, efficient in its use, readily set up in operative position with respect to tissue or fabrics, and comparatively inexpensive to manufacture. Another object is to provide for medical suturing devices that are single use. It is also an aim of the present invention to provide an improved suturing medical suturing system that provides improved ergonomic use and is of economical construction while providing nearly universal suturing operations without surgical fatigue, overcoming the complexities and limitations of conventional suturing devices and procedures.

Another object of the present invention is to provide a medical suturing device which provides knot tying of suturing material in line with the action of insertion of suturing material through a patient's tissue.

Additional objects, advantages and novel features of this invention shall be set forth in the description that follows, and in part will become apparent to those skilled in the art upon examination of the following specification. The objects and advantages of the invention may be realized and attained by means of the instrumentalities, combinations, and devices particularly pointed out in the appended claims.

The following presents a simplified summary of the present disclosure in a simplified form as a prelude to the more detailed description that is presented herein.

Therefore, to achieve the foregoing and other objects and in accordance with the purposes and embodiments of the present invention, as embodied and described herein, there is provided a handheld medical suturing device comprising a handle body having a hinge operatively connected to a distal end of a handle lever. The handle lever is adapted to be grasped by a hand of a user. The handle body has proximal end adapted to be grasped by a user and a distal end which defines an opening adapted to receive a tissue.

In a preferred embodiment, the handheld medical suturing device includes an actuating arm disposed within the handle body. The actuating arm has a proximal end and a distal end, and the proximal end of the actuating arm is fixed to the distal end of the handle lever.

In one embodiment, the handheld medical suturing device includes a bent constrained rigid body, which has a proximal end and a distal end. The proximal end of the bent constrained rigid body is operatively connected to the actuating arm. The distal end of the bent constrained rigid body is operatively connected to a pivoting radial arm.

The pivoting radial arm has a proximal end opposite a distal end. The proximal end of the pivoting radial arm is operatively connected to a fulcrum point disposed within the handle body. The distal end of the pivoting radial arm is operatively connected to the distal end of the bent constrained rigid body.

In a preferred embodiment, the handheld medical suturing device includes a curved suturing needle assembly disposed within the handle body. The curved suturing needle assembly has a proximal end and a distal end. The proximal end is operatively connected to the distal end of the pivoting radial arm. The curved suturing needle is adapted to advance a suture through the tissue by a rotation of the actuating arm and respective rotation of the bent constrained rigid body along an XY plane that is substantially perpendicular to the tissue. Such rotation rotates the curved suturing needle assembly through the tissue between a retracted position and a fully extended position upon a pivoting of the handle lever relative to the handle body from an open position to a squeezed position.

In one embodiment, the handheld medical suturing device further includes at least one spool of suture disposed within an inner cavity passageway defined by the proximal end of the handle body. Preferably, the handle body comprises an internal rectangular tube having walls that define the inner cavity passageway. The suture is threaded from the at least one spool through the inner cavity passageway of the handle body to the curved suturing needle assembly, and the suture is further threaded from the curved suturing needle assembly to a bobbin that is disposed within the distal end of the handle body of the handheld medical suturing device. The at least one spool is configured to dispense the suture to the curved suturing needle assembly upon the rotation of the curved suturing needle from the retracted position to the fully extended position.

In yet another embodiment, the handheld medical suturing device further includes a fixed bobbin channel that has a semi-annular body, which forms a bobbin channel cavity disposed within the distal end of the handle body. The semi-annular body defines an elongated slot therethrough, preferably located at the bottom of the semi-annular body of the fixed bobbin channel. The semi-annular body has a proximal end opposite a distal end, and the bobbin channel cavity has a central axis that is perpendicular to the XY plane.

In one embodiment, the handheld medical suturing device further comprises a bobbin carrier that is movably fitted within the bobbin channel cavity of the fixed bobbin channel. The bobbin carrier comprises a semi-annular body that forms a bobbin carrier cavity that is configured to receive the curved suturing needle assembly in the fully extended position. The bobbin carrier is adapted for movement of the bobbin along the central axis across the XY plane, between a rest position and an actuated position, as the bobbin is rotatably disposed within the bobbin carrier cavity of the bobbin carrier.

In a preferred embodiment, the bobbin carrier of the handheld medical suturing device comprises a rack disposed along a bottom of the bobbin carrier. The rack is operatively fitted within the elongated slot of the fixed bobbin channel.

In yet another preferred embodiment, the handheld medical suturing device further includes a mutilated spur gear that is fixed to a first drive axle disposed inside the handle body. In another embodiment, the handheld medical suturing device includes a un-mutilated spur gear, rather than a mutilated spur gear.

Preferably, the first drive axle is connected to a first thumb lever that extends outwardly of the handle body. The mutilated spur gear operatively engages the rack to translate and impart rotational motion of the mutilated spur gear into linear motion of the rack from the rest position to the actuated position, upon the rotation of the first thumb lever from a first thumb lever first position to a first thumb lever second position. The linear motion of the rack moves the bobbin carrier side to side within the bobbin channel.

In a preferred embodiment, the bobbin of the handheld medical suturing device has opposing hemispherical heads and a cylindrical body that forms an axle disposed between such opposing hemispherical heads. That axle is adapted to contain the suture between the opposing hemispherical heads. The cylindrical body is adapted to release the suture therefrom upon the movement of the bobbin carrier from the rest position to the actuated position, such that the bobbin is moved across the XY plane, preferably when the curved needle suturing assembly is in the fully extended position. The movement of the bobbin carrier across the XY plane moves the suture through a bow that is formed by the suture extending from the curved suturing assembly.

In one embodiment, the handheld medical suturing device includes at least one spring biasing member that is disposed within the inner cavity passageway of the handle body. The spring biasing member is preferably positioned between and connected to the at least one spool and an inner wall of the proximal end of the handle body. Such at least one biasing member tensions the suture between the at least one spool and the bobbin.

In another embodiment, the handheld medical suturing device further includes at least one spring biasing member that is disposed around the hinge of the handheld medical suturing device. Such at least one spring biasing member is operatively connected to the handle body and the distal end of the handle lever at the hinge, and such at least one biasing member pivotally biases the proximal end of the handle lever away from the proximal end of the handle body.

In a preferred embodiment, the handheld medical suturing device further comprises a first spur gear that is concentrically disposed around and fixed to the first drive axle. The handheld medical suturing device further comprises a second spur gear concentrically disposed around and fixed to a second drive axle. The second drive axle is connected to a second thumb lever, which extends outward of the handle body. The first spur gear operatively engages the second spur gear. Similarly, the second spur gear engages the first spur gear to impart rotational movement.

In another preferred embodiment, the handheld medical suturing device further comprises at least one locking pin fixed to the first thumb lever. Preferably, the handle lever defines a channel, wherein in the squeezed position and in the actuated position, the at least one locking pin aligns with the channel upon the rotation of the first thumb lever from the first thumb lever first position to the first thumb lever second position; an opening of the handle lever causes the locking pin to penetrate and slide into the channel of the handle lever, and such penetration of the locking pin in the channel of the handle lever obstructs a second pivoting of the handle relative to the handle body from the squeezed to the open position.

In such preferred embodiment, the at least one locking pin of the handheld medical suturing device is configured for withdrawal from the channel upon a rotation of the first thumb lever by a user from the first thumb lever second position to the first thumb lever first position.

In a preferred embodiment, the handheld medical suturing device further comprises at least one spool of the suture that is disposed within an inner cavity passageway that is defined by the proximal end of the handle body. The suture is preferably threaded from the at least one spool through the inner cavity passageway to the curved suturing needle assembly. The suture is further threaded from the curved suturing needle assembly to a bobbin that is disposed within the distal end of the handle body. The at least one spool is adapted to dispense the suture to the curved suturing needle assembly upon the rotation of the curved suturing needle by a user from the retracted position to the fully extended position.

In such preferred embodiment, the bobbin has a proximal end opposite a distal end, and the proximal end preferably comprises a first plurality of annularly disposed ridges that are configured to provide a first frictional resistance against rotation of the bobbin within the bobbin carrier upon a rotation of the curved suturing needle assembly through the tissue, between the retracted position and the fully extended position, in order to keep the suture taut, upon the pivoting of the handle lever relative to the handle body. The frictional resistance of the first plurality of annularly disposed ridges also maintains tension on the suture upon the movement of the bobbin along the central axis across the XY plane between a rest position and an actuated position.

In another preferred embodiment, the distal end of the bobbin comprises a second plurality of annually disposed ridges that provide a second frictional resistance against rotation of the bobbin relative to the bobbin carrier upon the rotation of the curved suturing needle assembly through the tissue, between the retracted position and the fully extended position, upon the pivoting of the handle lever relative to the handle body. Such second frictional resistance is also adapted to maintain tension on the suture upon a user's movement of the bobbin along the central axis across the XY plane between a rest position and an actuated position.

In yet another embodiment, the handheld medical suturing device has at least one magnet disposed within a wall of the bobbin carrier, in a spaced relation to the bobbin, and the bobbin comprises a ferrous material that is configured for a magnetic attraction, to provide a frictional resistance against rotation of the bobbin relative to the bobbin carrier, in order to keep the suture taut.

In another embodiment, the handheld medical suturing device preferably comprises at least one magnet that is disposed within a wall of the handle body, and the handheld medical suturing device further comprises at least one spool of suture that is disposed within an inner cavity passageway that defined by the proximal end of the handle body, and the at least one spool comprises a ferrous material that is adapted to provides a magnetic attraction to said at least one magnetic disc configured to provide a frictional resistance against rotation of the at least one spool relative to the wall of the handle body, in order to keep the suture taut.

In a preferred embodiment, the curved suturing needle assembly of the handheld medical suturing device comprises an outer curved needle fixed to an inner curved needle. The outer curved needle has a proximal end opposite a distal end. The inner curved needle has a proximal end opposite a distal end. The curved suturing needle assembly preferably includes a shroud that is disposed along an outer surface of the outer curved needle and of the inner curved needle. The shroud forms a passage for the suture to thread therethrough.

The shroud includes a pointed cover encapsulating the distal end of the outer curved needle.

In yet another preferred embodiment, the handheld medical suturing device includes an elbow guide disposed within the pointed cover. The elbow guide engages and guides the suture when the suture extends outwardly from the distal end of the inner curved needle. The distal end of the inner curved needle preferably defines a ramp to engagingly guide the suture.

In one embodiment, the handheld medical suturing device includes a single length of suture, where a first portion of the single length of suture is disposed around the at least one spool, where a second portion of the single length of suture is disposed along the curved suturing needle assembly, where a third portion of the single length of suture is disposed inside the bobbin carrier cavity, and where a fourth portion of the single length of suture is disposed around the bobbin.

In another one embodiment, the handheld medical suturing device includes a single length of suture, where a first portion of the single length of suture is disposed around the at least one spool, where a second portion of the single length of suture is disposed within the shroud of the curved suturing needle assembly, where a third portion of the single length of suture is disposed inside the bobbin carrier cavity, and where a fourth portion of the single length of suture is disposed around the bobbin.

In one embodiment, the curved suturing needle assembly includes a single curved needle having an inner surface which defines an annular groove. The single curved needle has a plurality of containment bridges annularly disposed along the annular groove of the inner surface. The plurality of containment bridges contain the suture within the annular groove.

In another embodiment, the curved suturing needle assembly includes a single curved needle that is a hollow needle, and suture is threaded through the hollow needle. In such embodiment, the curved suturing needle assembly includes a curved hollow needle body having a proximal end opposite a distal end. The proximal end of the curved hollow needle body defines a first orifice. The distal end of the curved hollow needle body defines a second orifice. The curved hollow needle body defines a passage therethrough between the first orifice and the second orifice, and the suture is threaded through the first orifice, through the passage, and through the second orifice.

As further embodied and described herein, there is provided a curved suturing needle assembly having an outer curved needle fixed to an inner curved needle. The outer curved needle has a proximal end opposite a distal end. The inner curved needle has a proximal end opposite a distal end.

In a preferred embodiment, the curved suturing needle assembly includes a shroud disposed along an outer surface of the outer curved needle and the inner curved needle. The shroud forms a passage for the suture. Preferably, the shroud comprises a pointed cover encapsulating the distal end of the outer curved needle.

In yet another preferred embodiment, the curved suturing needle assembly includes an elbow guide disposed within the pointed cover of the shroud. The elbow guide is configured to engage and guide the suture when the suture extends outward from the distal end of the inner curved needle. The distal of the inner curved needle preferably defines a ramp adapted to engagingly guide the suture.

These and other features, aspects, and advantages of the present invention will become better understood with reference to the following description and appended claims.

BRIEF DESCRIPTION OF THE DRAWINGS

Illustrative embodiments of the present invention are described herein with reference to the accompanying drawings, in which.

DETAILED DESCRIPTION

Figure 1:
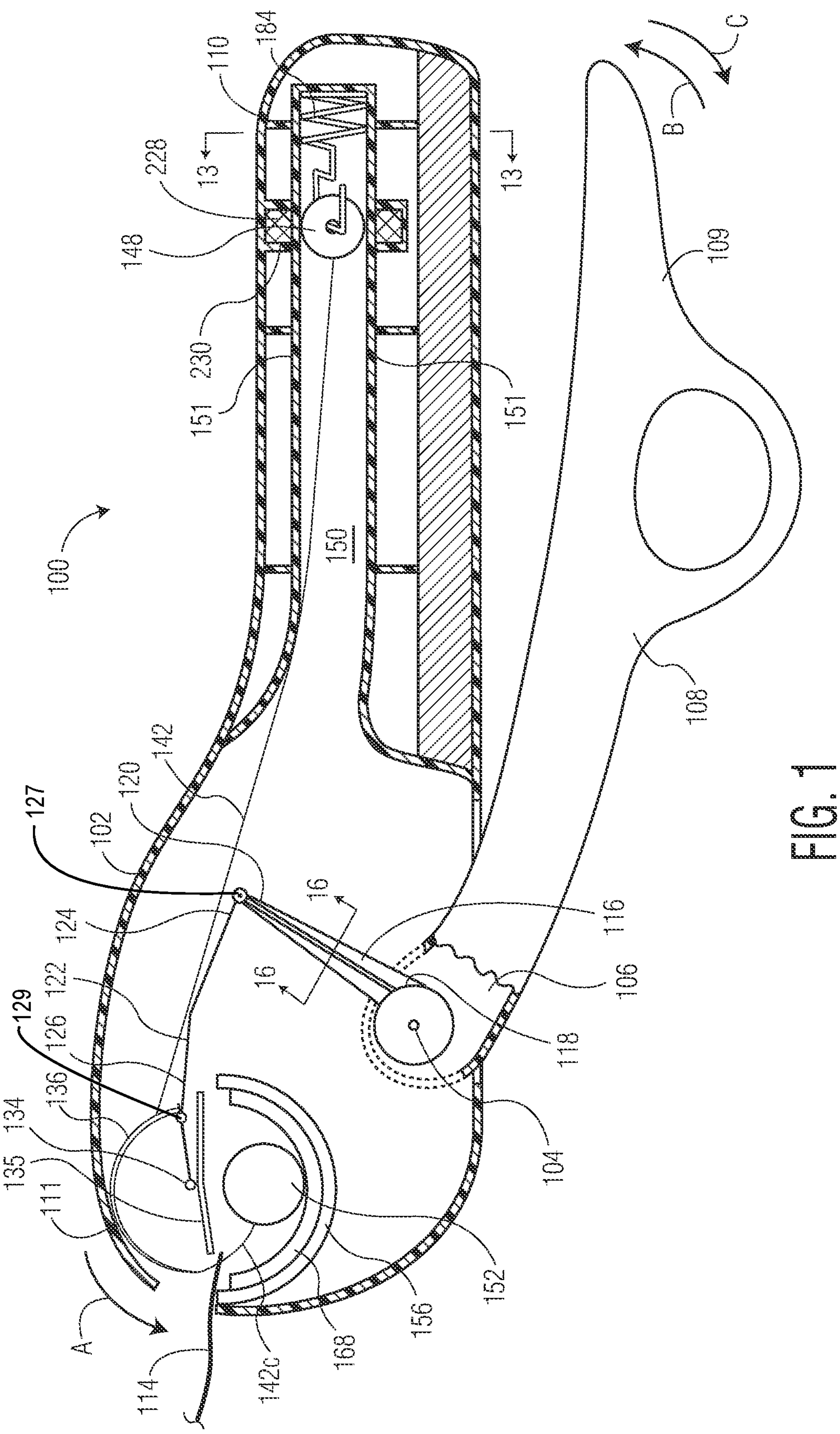
FIG. 1 is a partial cutaway cross-sectional view of an exemplary handheld medical suturing device in a rest position and showing an exemplary tissue, in accordance with embodiments of the invention.

For a further understanding of the nature and function of the embodiments, reference should be made to the following detailed description. Detailed descriptions of the embodiments are provided herein, as well as, the best mode of carrying out and employing the present invention. It will be readily appreciated that the embodiments are well adapted to carry out and obtain the ends and features mentioned as well as those inherent herein. It is to be understood, however, that the present invention may be embodied in various forms. Therefore, persons of ordinary skill in the art will realize that the following disclosure is illustrative only and not in any way limiting, as the specific details disclosed herein provide a basis for the claims and a representative basis for teaching to employ the present invention in virtually any appropriately detailed system, structure or manner. It should be understood that the devices, materials, methods, procedures, and techniques described herein are presently representative of various embodiments. Other embodiments of the disclosure will readily suggest themselves to such skilled persons having the benefit of this disclosure.

For purposes of clarity and orientation with respect to a person, referred to herein as a user, it is noted that a transverse (also known as axial or horizontal) plane is an XZ plane, parallel to the ground. A frontal (also known as coronal) plane is a YX plane, perpendicular to the ground, which (in humans) separates the anterior from the posterior, the front from the back, the ventral from the dorsal. A sagittal (also known as lateral) plane is an XY plane, perpendicular to the ground, which separates left from right. Objects are coplanar if they all lie in the same plane. For example, one axis is coplanar with another axis when the two axes lie in the same plane.

As used herein, "axis" means a real or imaginary straight line about which a three-dimensional body is symmetrical. A "vertical axis" means an axis perpendicular to the ground (or put another way, an axis extending upwardly and downwardly). A "horizontal axis" means an axis parallel to the ground.

As used herein, homogeneous is defined as the same in all locations, and a homogeneous material is a material of uniform composition throughout that cannot be mechanically separated into different materials. Examples of "homogeneous materials" are certain types of plastics, ceramics, glass, metals, alloys, paper, board, resins, and coatings.

Reference will now be made in detail to the present preferred embodiments of the invention, examples of which are illustrated in the accompanying drawings. Wherever possible, the same reference numerals are used in the drawings and the description to refer to the same or like parts.

Figure 2:
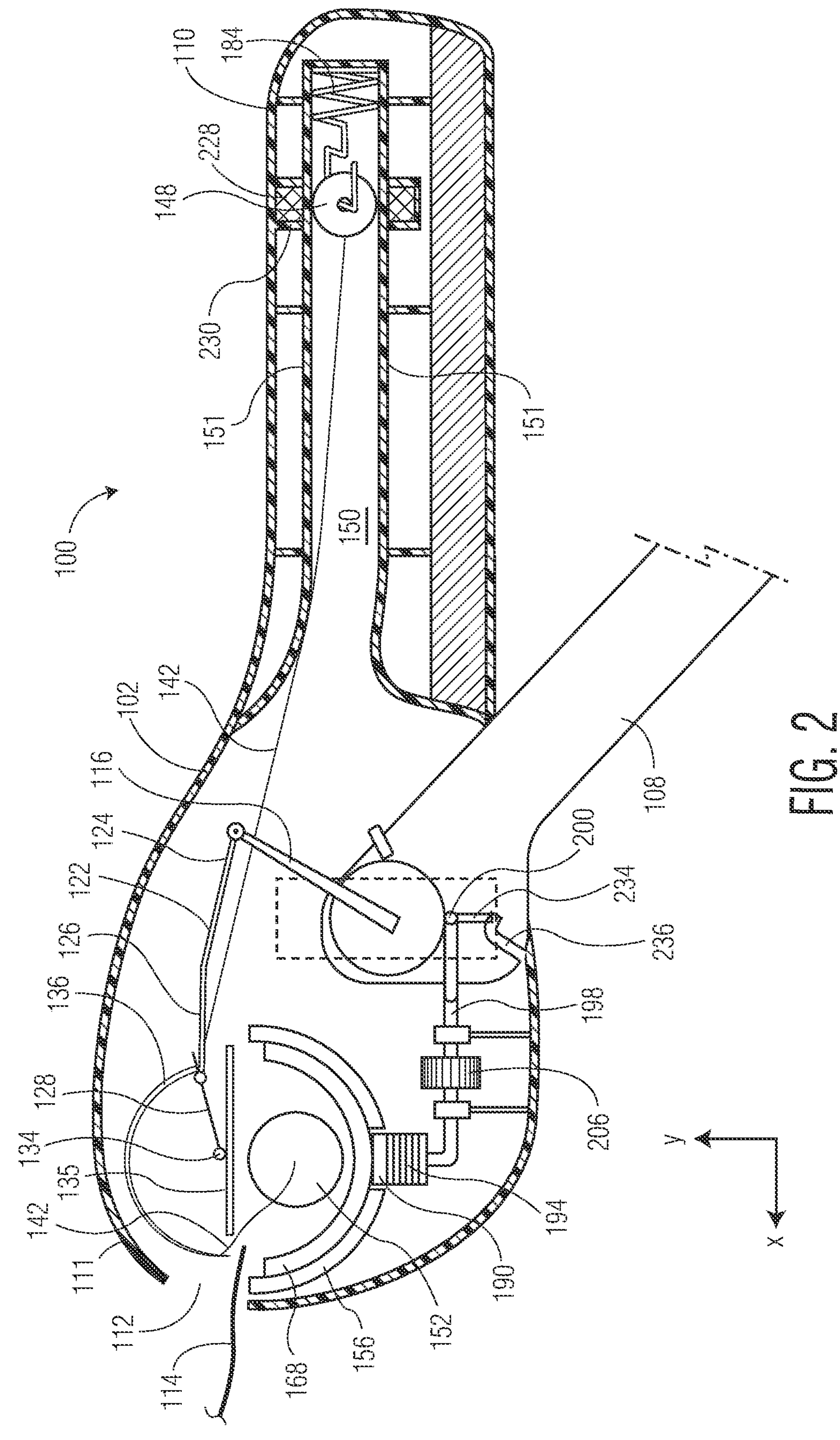
FIG. 2 is another partial cutaway cross-sectional view of the exemplary handheld medical suturing device showing additional embodiments in a rest position and showing an exemplary tissue, in accordance with embodiments of the invention.
Figure 3:
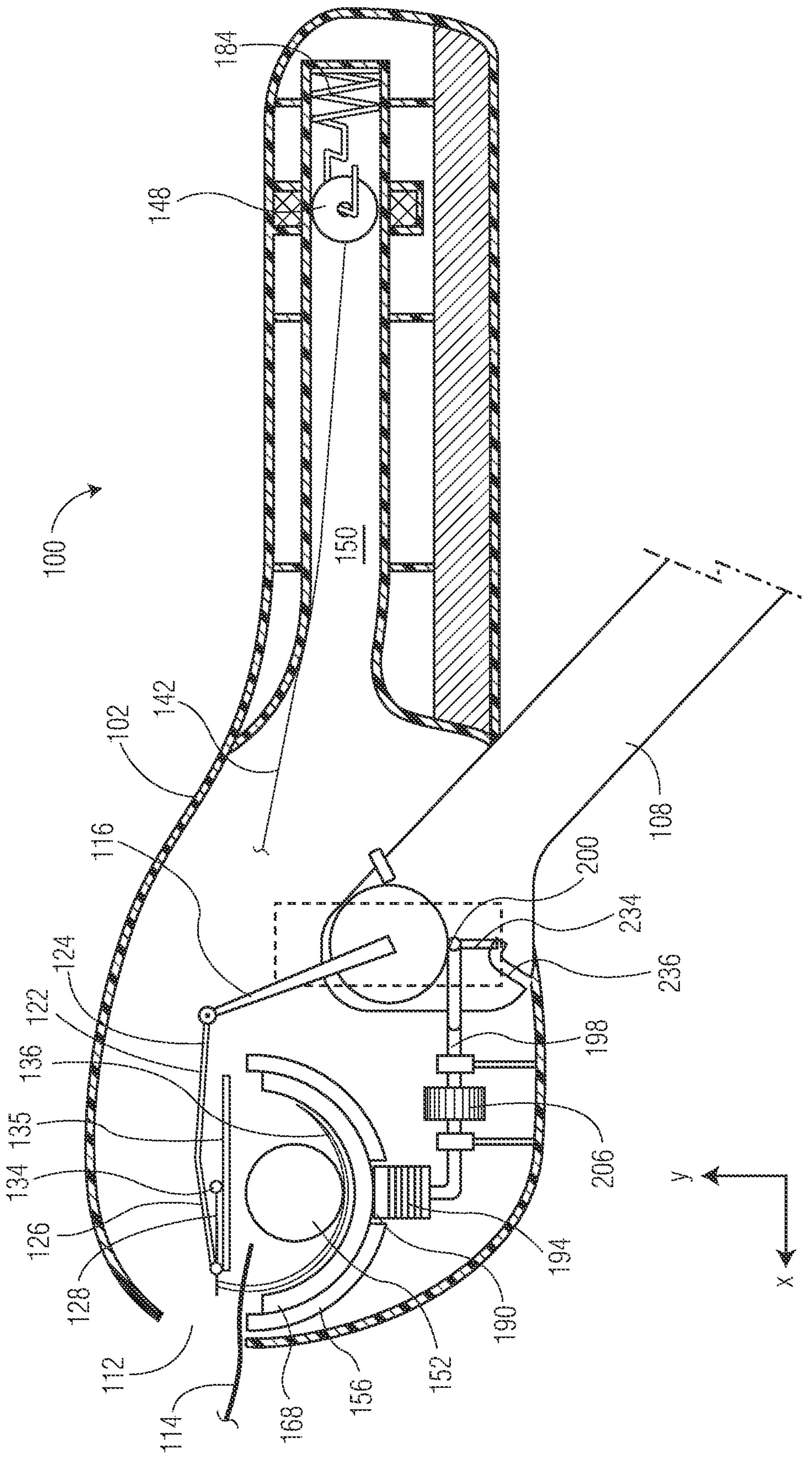
FIG. 3 is another partial cutaway cross-sectional view of the exemplary handheld medical suturing device in a fully extended position and showing an exemplary tissue, in accordance with embodiments of the invention.

Referring initially to FIGS. 1-3, the basic constructional details and principles of operation of one embodiment of a handheld medical suturing device 100 according to a preferred embodiment of the present invention will be discussed. The handheld medical suturing device 100 preferably has a handle body 102 having a hinge 104 operatively connected to a distal end 106 of a handle lever 108. The handle lever is adapted to be grasped by a hand of a user. The handle body 102 has proximal end 110 adapted to be grasped by a user and a distal end 111 which defines an opening 112 adapted to receive a tissue 114, as exemplified in FIGS. 1-3 and 19.

In a preferred embodiment, the handheld medical suturing device 100 includes an actuating arm 116 disposed within the handle body 102. The actuating arm 116 has a proximal end 118 and a distal end 120, and the proximal end 118 of the actuating arm 116 is fixed to the distal end 106 of the handle lever 108, as illustrated in FIG. 1.

Figure 38:
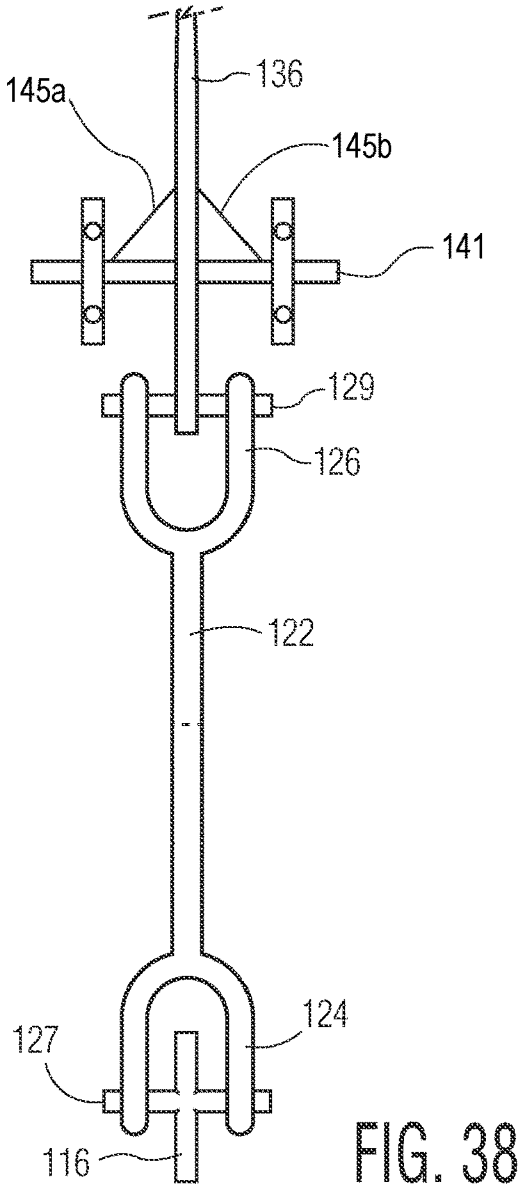
FIG. 38 is a view of a partial cutaway cross-sectional view of an exemplary bent constrained rigid body of a handheld medical suturing device, in accordance with embodiments of the invention.

As seen in FIGS. 1-3, in one embodiment, the handheld medical suturing device includes a bent constrained rigid body 122, which has a proximal end 124 and a distal end 126. The proximal end 124 of the bent constrained rigid body 122 is operatively connected to the actuating arm 126 at a moveable joint 127 (FIG. 38). The distal end 126 of the bent constrained rigid body 122 is operatively connected to a pivoting radial arm 128 (not shown), preferably at a moveable joint 129 (FIG. 38). For purposes of clarity, in the the partial cutaway top view of FIG. 38, the curved suturing needle assembly 136 obstructs the view of the pivoting radial arm 128 in FIG. 38.

Figure 15:
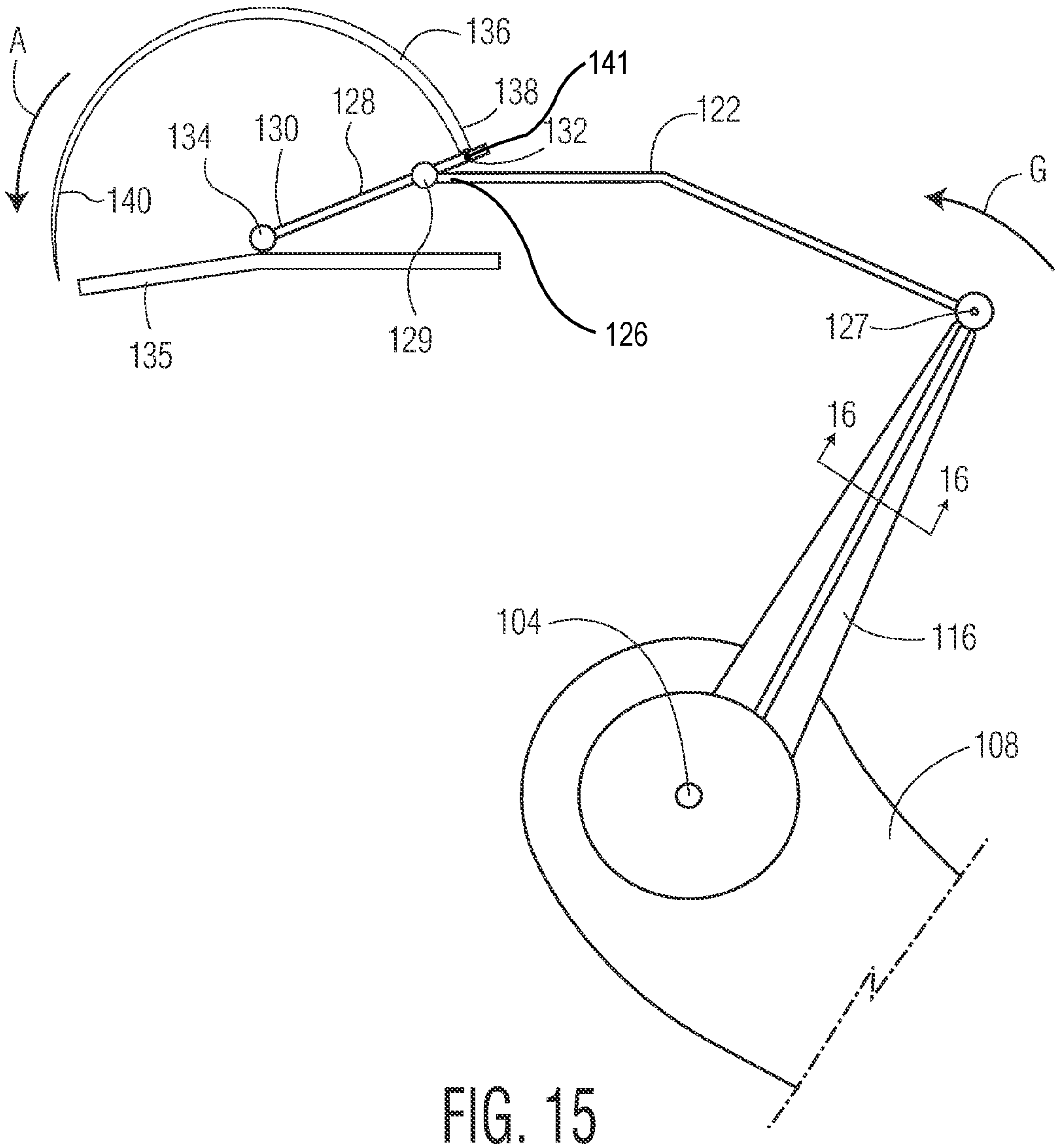
FIG. 15 is a partial cutaway cross-sectional view of a handheld medical suturing device, showing a curved needle suturing assembly in a retracted position, in accordance with embodiments of the invention.
Figure 16:
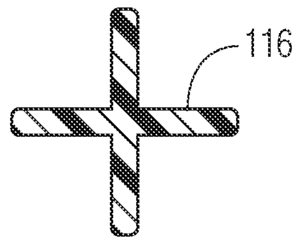
FIG. 16 is a cross sectional view along the cutting view 16-16 of FIG. 15 of an actuating arm of a handheld medical suturing device, in accordance with embodiments of the invention.
Figure 17:
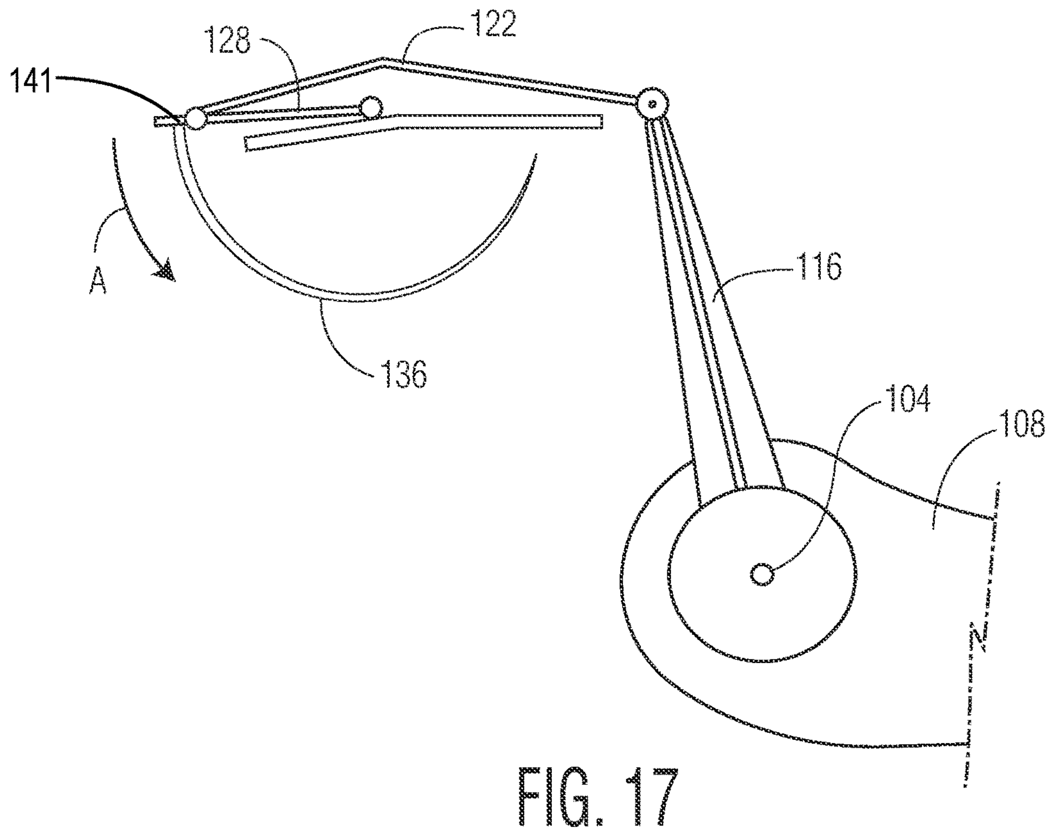
FIG. 17 is a partial cutaway cross-sectional view of embodiments of a handheld medical suturing device, showing a curved needle suturing assembly in a fully extended position, in accordance with embodiments of the invention.
Figure 39:
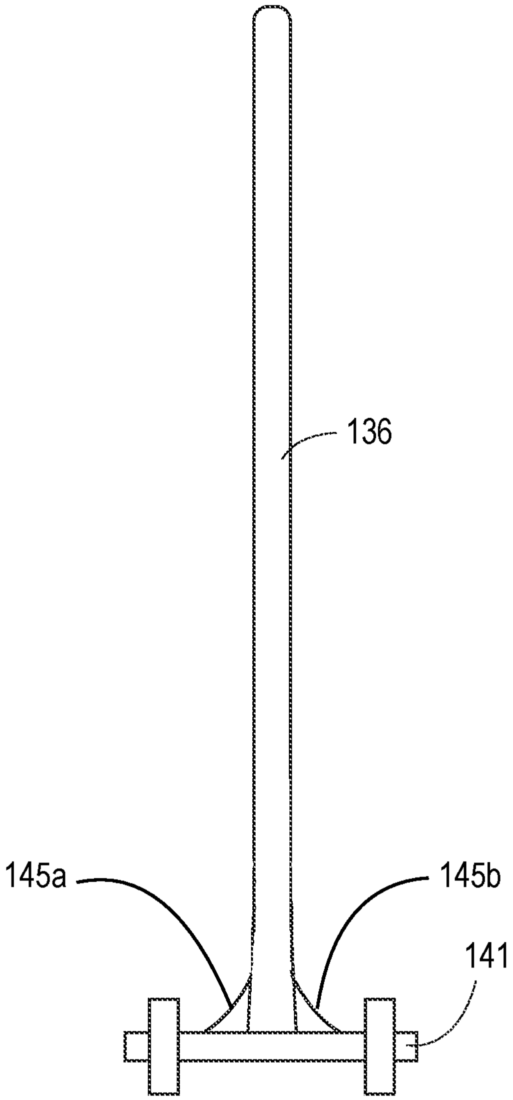
FIG. 39 is a top partial cutaway cross-sectional view of a curved needle suturing assembly, in accordance with embodiments of the invention.

FIGS. 15-17 illustrate enlarged views of the actuating arm 116 operatively connected to the bent constrained rigid body 122, which is operatively connected to the pivoting radial arm 128, and FIGS. 38-39 illustrate enlarged views of the preferred moveable joints 127, 129. However, the pivoting radial arm 128 is clearly illustrated in at least FIGS. 1-3, 15, 17, and 33.

The pivoting radial arm 128 has a proximal end 130 opposite a distal end 132, as exemplified in FIGS. 1 and 15. Referring to FIG. 15, the proximal end 130 of the pivoting radial arm 128 is operatively connected to a fulcrum point 134 that is disposed within the handle body 102, preferably at a position just above a transverse separator wall 135 that is fixed within the handle body 102, preferably as illustrated in at least FIGS. 1-3. The distal end 132 of the pivoting radial arm 128 is operatively connected to the distal end 126 of the bent constrained rigid body 122.

Referring initially to FIGS. 1-5 and 15-17, the handheld medical suturing device 100 includes a curved suturing needle assembly 136 disposed within the handle body 102. The curved suturing needle assembly 136 has a proximal end 138 and a distal end 140. The proximal end 138 is operatively connected to the distal end 132 of the pivoting radial arm 130, as exemplified in FIG. 15.

Preferably, the proximal end 138 of the curved suturing needle assembly 136 is operatively connected to the distal end 132 of the pivoting radial arm 128 at a needle fulcrum point 141, as illustrated in FIGS. 15, 17, and 39, for example. The fulcrum point 141 preferably has an axis that is both transverse to the pivoting radial arm 128 and to the curved suturing needle assembly 136. As illustrated in FIG. 39, in a preferred embodiment, the curved suturing needle assembly 136 includes lateral supports 145*a*, 145*b* each fixed to the proximal end 138 of the curved suturing needle assembly 136 and the needle fulcrum point 141, to provide additional rigidity.

Figure 18:
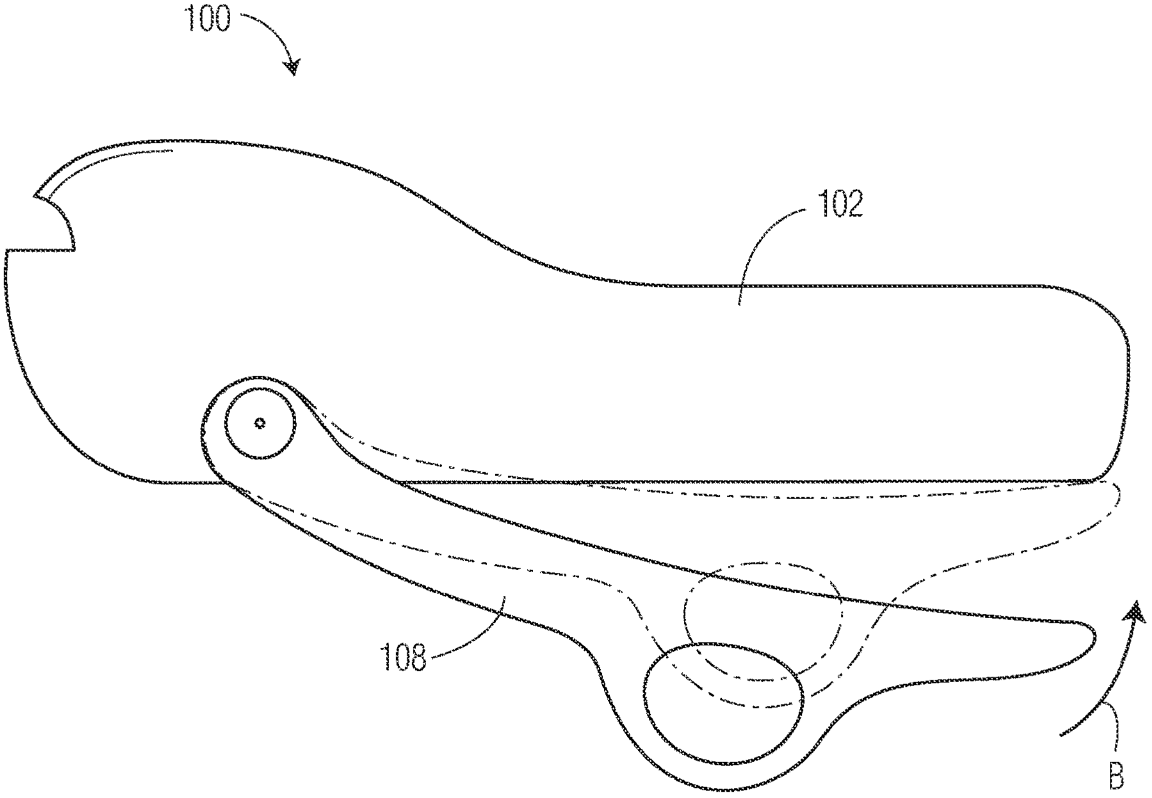
FIG. 18 is a side elevation, partial cutaway, view of a handheld medical suturing device, in accordance with embodiments of the invention.

The curved suturing needle assembly 136 is adapted to advance a suture 142 through the tissue 144, in the direction of Arrow A in FIG. 1, by a rotation of the actuating arm 116 and respective rotation of the bent constrained rigid body 122, in the direction of Arrow G in FIG. 15, along an XY plane (FIG. 2) that is substantially perpendicular to the tissue 114, which is substantially on an transverse plane, which is an XZ plane. Such rotation of the actuating arm 116 and respective rotation of the bent constrained rigid body 122 (in the direction of Arrow G) rotates the curved suturing needle assembly 136 through the tissue 114 between a retracted position (as illustrated in FIGS. 1 and 15) and a fully extended position (as illustrated in FIGS. 3 and 17), because the pivoting radial arm 128 pivots around the fulcrum point 134, upon a pivoting of the handle lever 108 (in the direction of Arrow B in FIG. 18) relative to the handle body 102 from an open position (as illustrated in FIGS. 1, 2, and 15) to a squeezed position (as illustrated in FIGS. 3 and 17).

As illustrated in FIGS. 1-4 and 19, after the tissue 114 is inserted into the opening 112, the curved suturing needle assembly 136 can be rotated, and thus actuated and advanced, through the tissue 114, in the direction of Arrow A in FIG. 1, while the curved suturing needle assembly 136 remains fully disposed within and concealed by the handle body 102, thus overcoming the limitations of conventional medical devices, where the suturing needle is exposed, as such exposure gives rise to risk to the surgeon. As can be appreciated from the present disclosure, the embodiment of the disclosed invention provide a much safer handheld medical suturing device 100, because the curved suturing needle assembly 136 is guarded by the by the handle body 102, even when the curved suturing needle assembly 136 is actuated and advanced through the tissue 114 and/or tissues 114*a*, 114*b*. In other words, by the handle body 102 and its respective opening 112 mitigate risk of exposure of, and accidental contact between, the suturing needle and unintended objects such as a surgeon's hand. As such, it can be appreciated that, since the curved needle suturing assembly 136 is fully contained within the handle body 102 of the handheld medical suturing device 100, the handheld medical suturing device 100 greatly diminishes the chance for accidental puncture wounds to the surgeon and/or assistant, and thus, the disclosed invention reduces the chance for transmission of disease, such as hepatitis.

Figure 43:
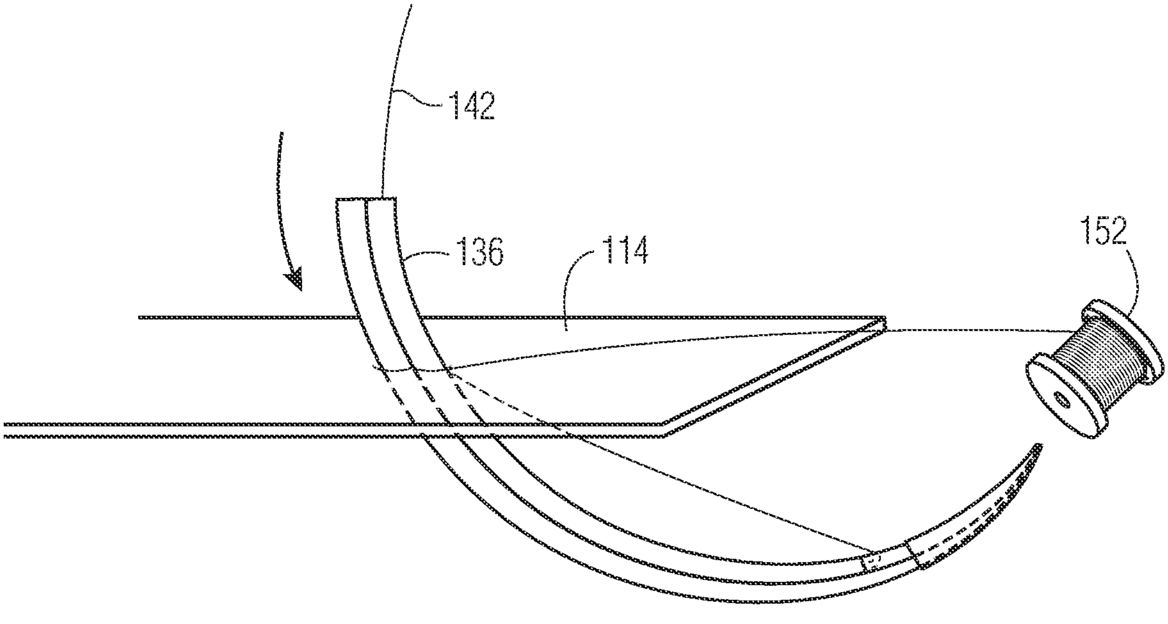
FIG. 43 is a partial cutaway view of a curved suturing needle assembly, a suture, and a bobbin of a handheld medical suturing device, with the bobbin in a rest position and with the curved suturing needle assembly in a fully extended position as penetrated through exemplary tissue, in accordance with embodiments of the invention.
Figure 44:
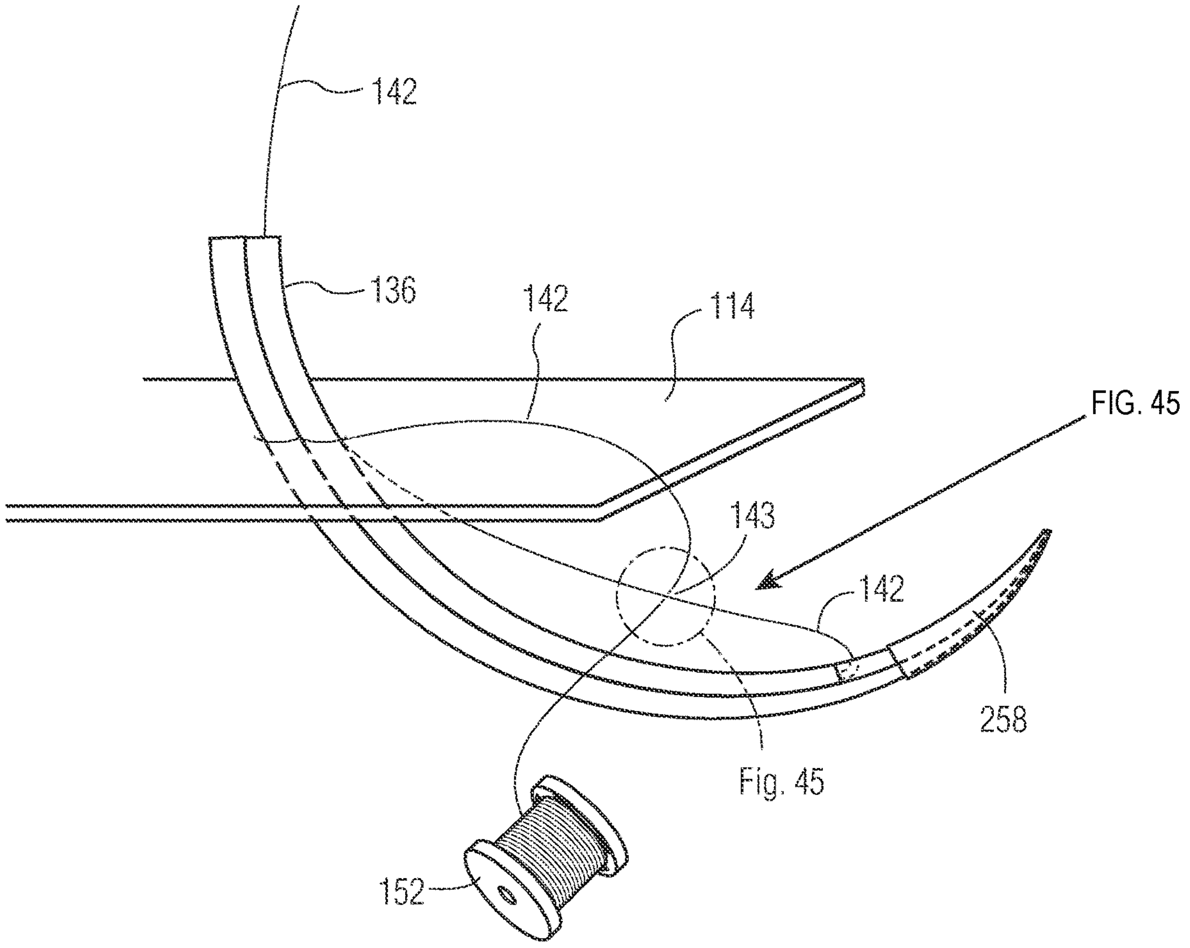
FIG. 44 is a partial cutaway view of a curved suturing needle assembly, a suture, and a bobbin of a handheld medical suturing device, with the bobbin in a n actuated position and with the curved suturing needle assembly in a fully extended position as penetrated through exemplary tissue, in accordance with embodiments of the invention.
Figure 45:
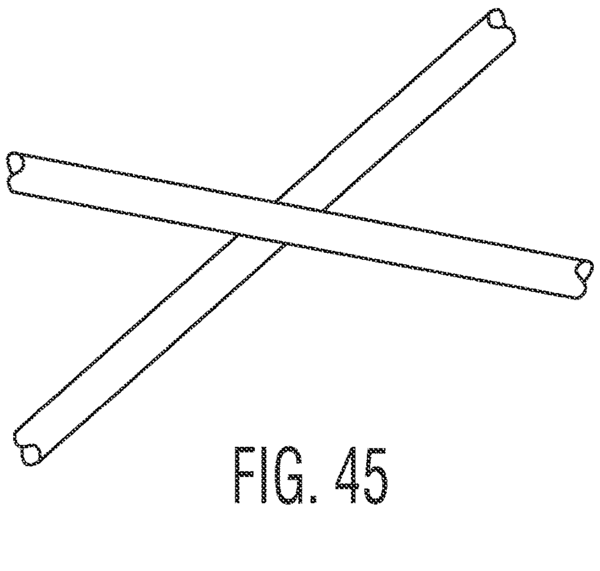
FIG. 45 is an enlarged view of a portion the suture of FIG. 44, illustrating a crossing of the suture to form a locking of the suture, in accordance with embodiments of the invention.
Figure 46:
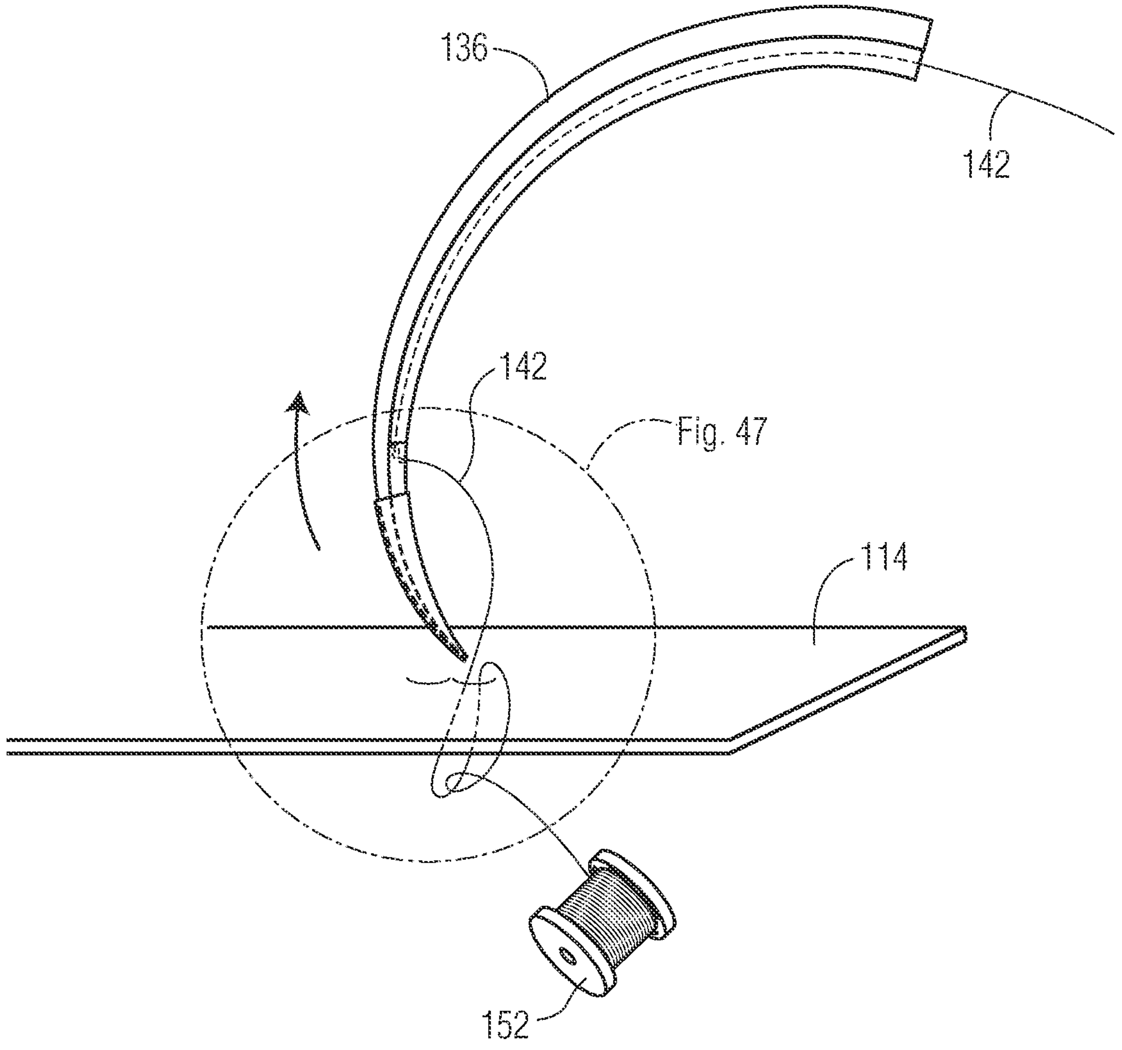
FIG. 46 is a partial cutaway view of a curved suturing needle assembly, a suture, and a bobbin of a handheld medical suturing device, illustrating a locking of the suture, in accordance with embodiments of the invention.
Figure 47:
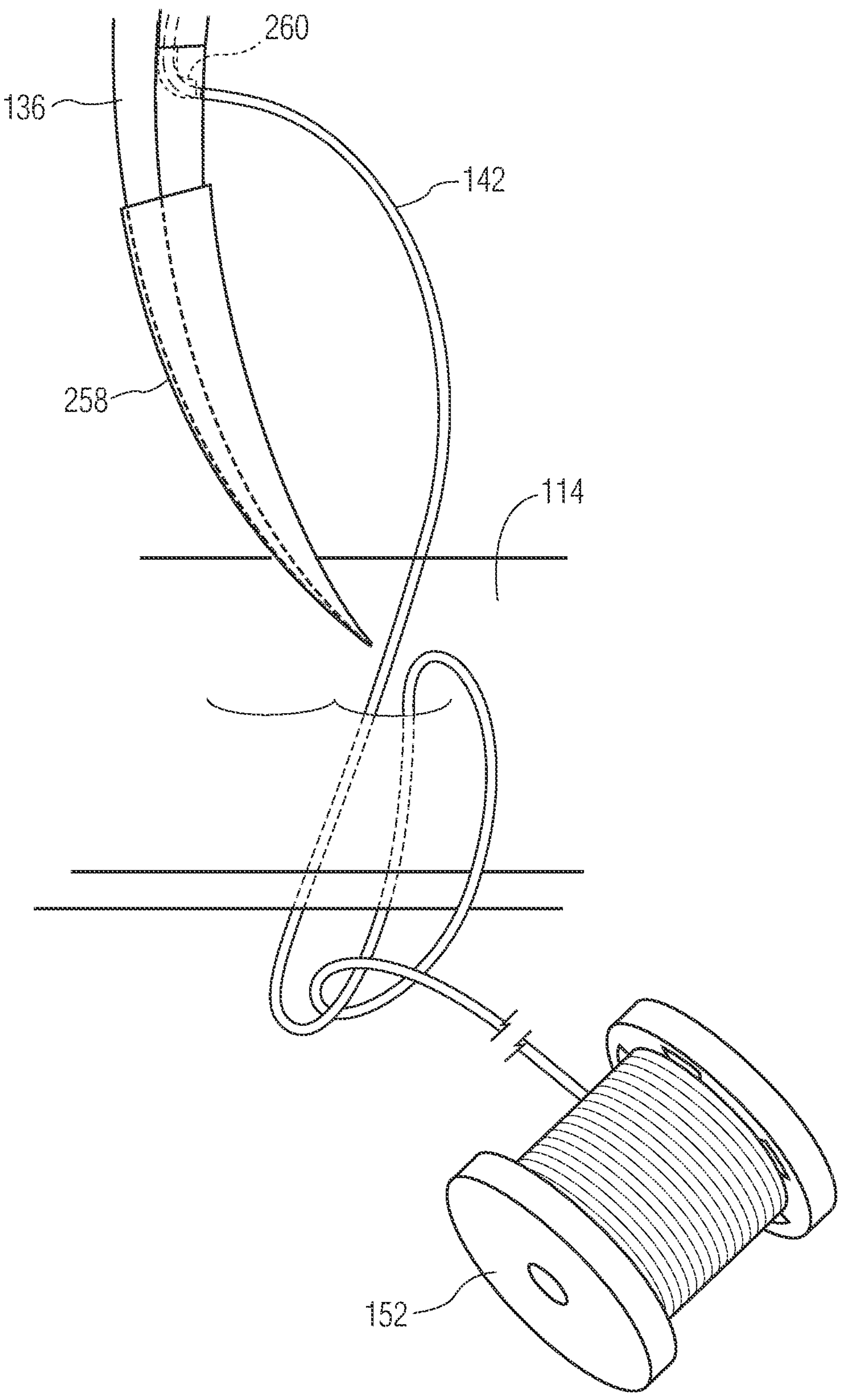
FIG. 47 is an enlarged partial cutaway view of a curved suturing needle assembly, a suture, and a bobbin of a handheld medical suturing device, illustrating a locking of the suture, in accordance with embodiments of the invention.
Figure 48:
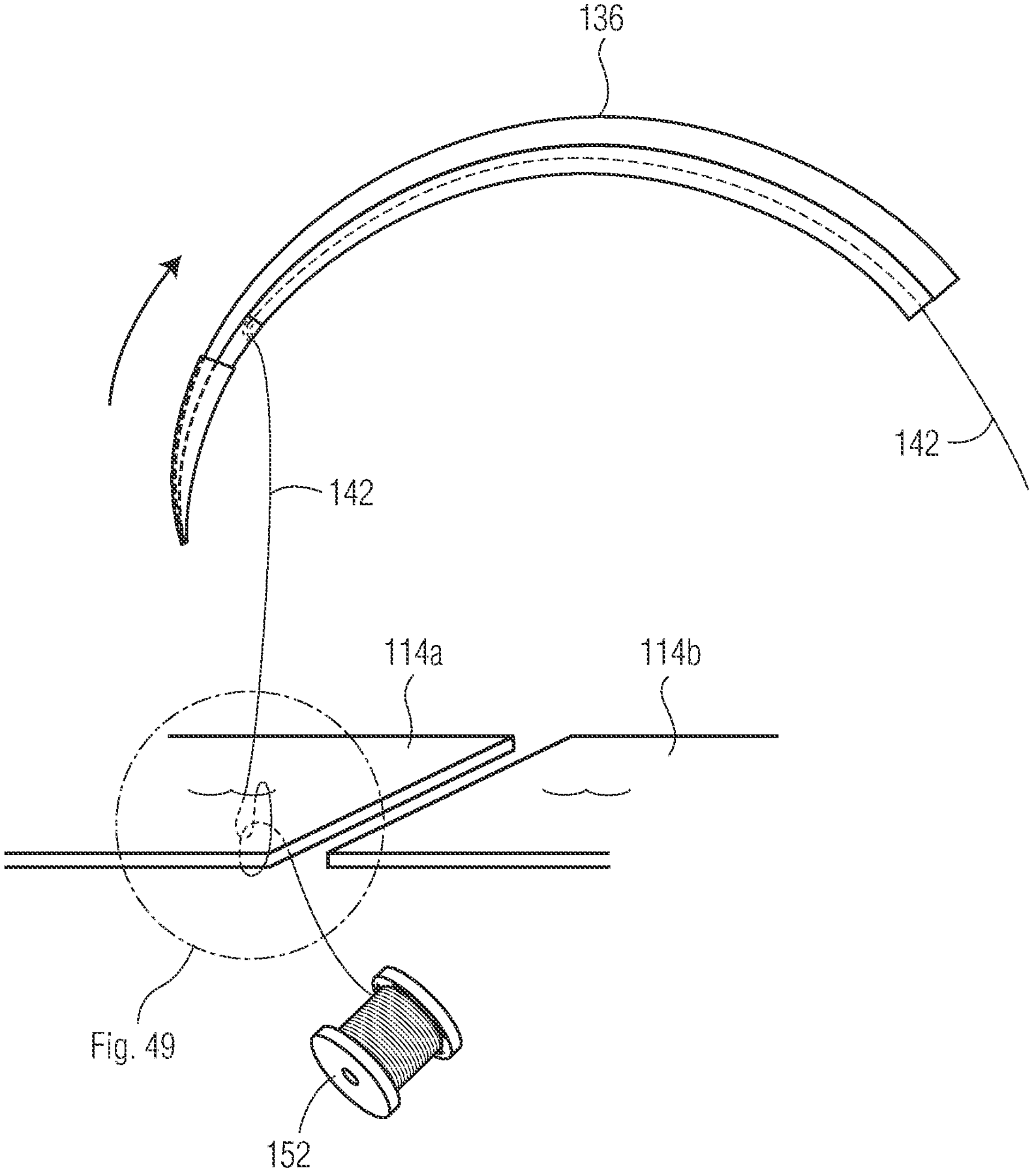
FIG. 48 is a partial cutaway view of a curved suturing needle assembly, a suture, and a bobbin of a handheld medical suturing device, illustrating a locking of the suture, with two pieces of exemplary tissue, in accordance with embodiments of the invention.
Figure 49:
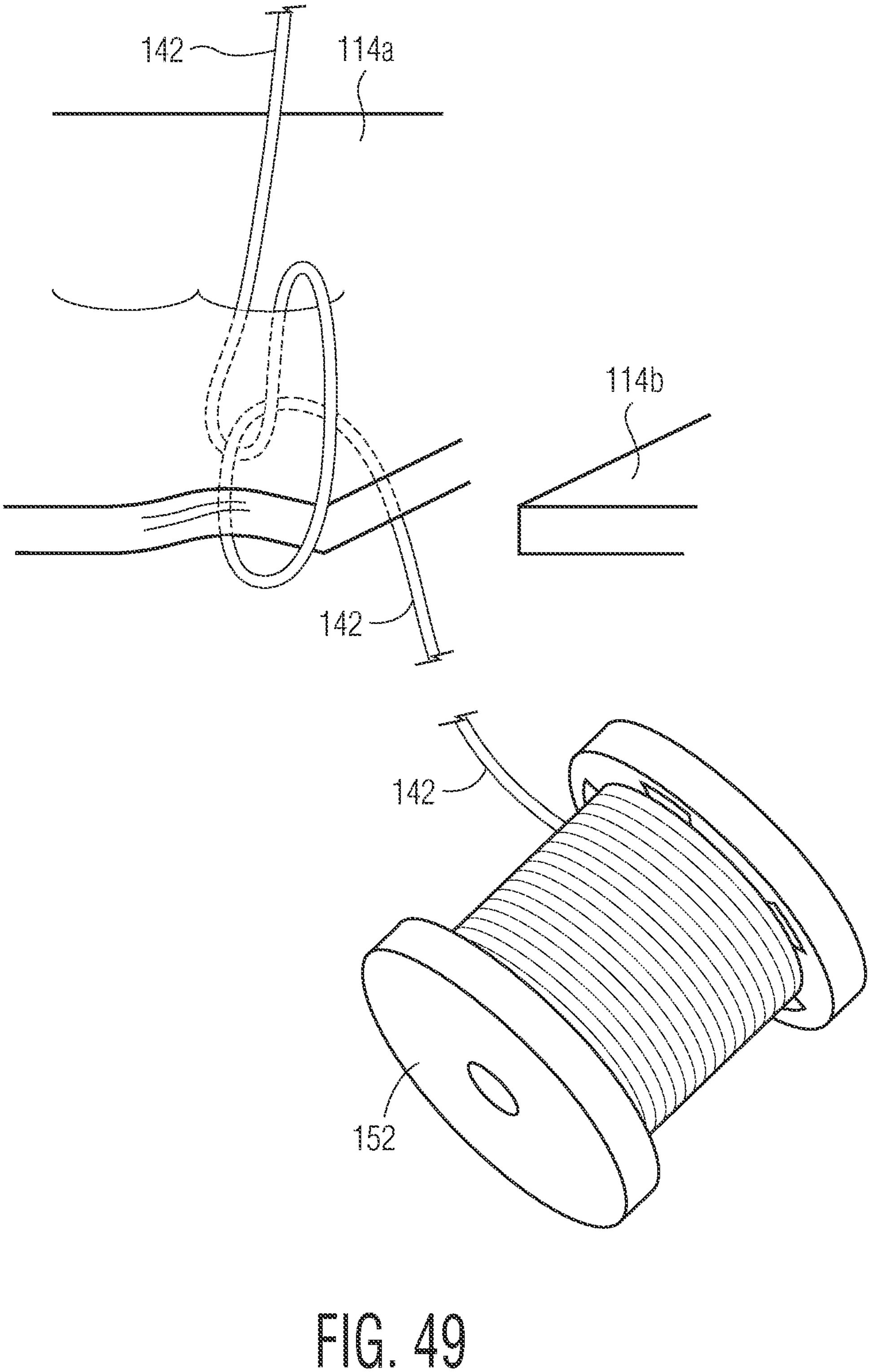
FIG. 49 is an enlarged partial cutaway view of a curved suturing needle assembly, a suture, and a bobbin of a handheld medical suturing device, illustrating a locking of the suture, with two pieces of exemplary tissue, in accordance with embodiments of the invention.
Figure 50:
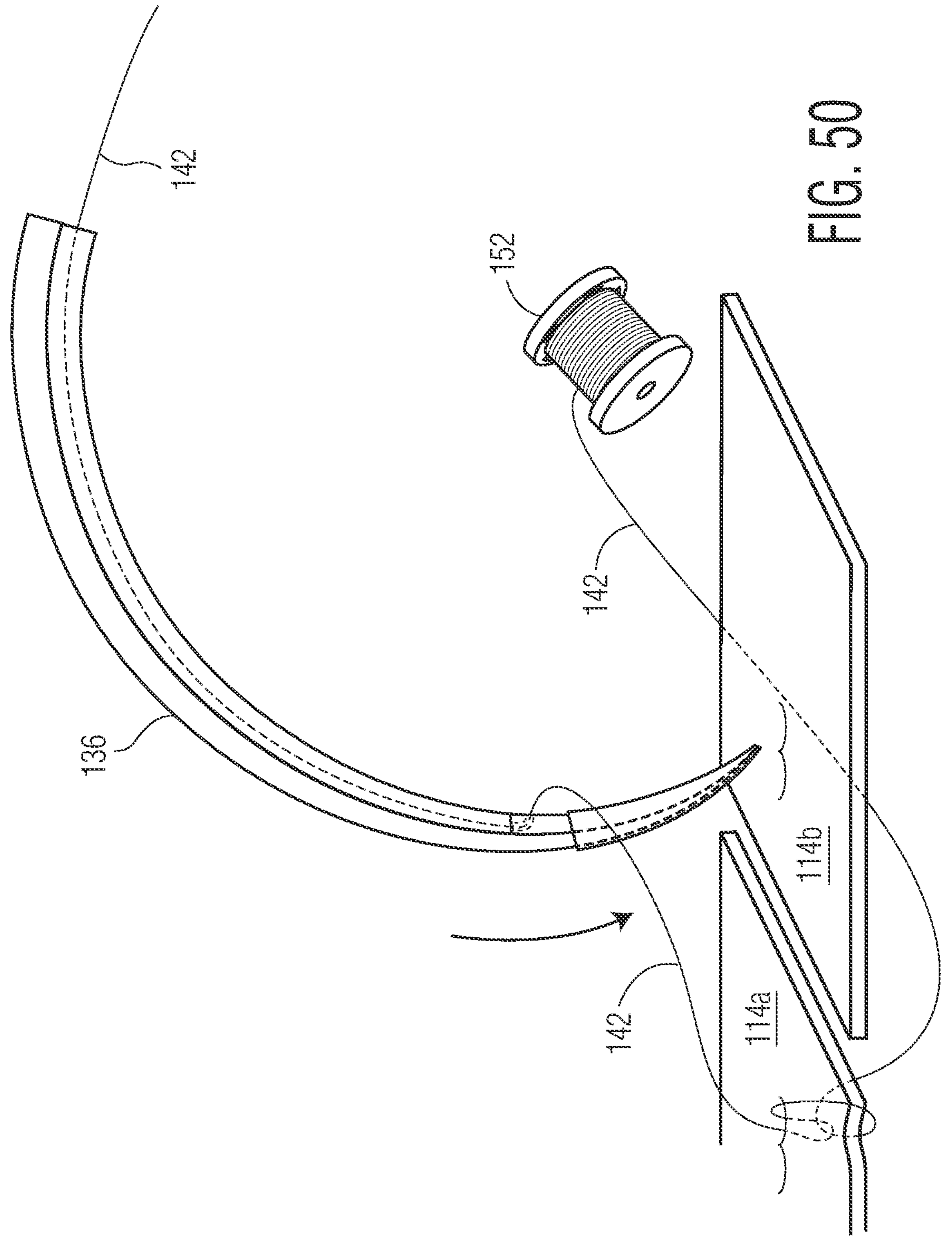
FIG. 50 is a partial cutaway view of a curved suturing needle assembly, a suture, and a bobbin of a handheld medical suturing device, with the bobbin in a rest position, illustrating a locking of the suture, illustrating a first piece and a second piece of exemplary tissue, and with the curved suturing needle assembly positioned to penetrate the second exemplary tissue, in accordance with embodiments of the invention.

In a preferred embodiment, referring to FIGS. 1-5, the handheld medical suturing device 100 further includes at least one spool 148 of suture 142 disposed within an inner cavity passageway 150 defined by the proximal end 110 of the handle body 102. The handle body 102 preferably comprises an internal rectangular tube 151 of walls that define the inner cavity passageway 150. The suture 142 is threaded from the at least one spool 148 through the inner cavity passageway 150 of the handle body 102 to the curved suturing needle assembly 136. The suture 142 is further threaded from the curved suturing needle assembly 136 to a bobbin 152 that is disposed within the distal end 111 of the handle body 102 of the handheld medical suturing device 100. The at least one spool 148 is configured to dispense the suture to the curved suturing needle assembly 136 upon the rotation of the curved suturing needle assembly from the retracted position (illustrated in FIGS. 1 and 15) to the fully extended position (illustrated in FIGS. 3, 17 and 43).

Figure 4:
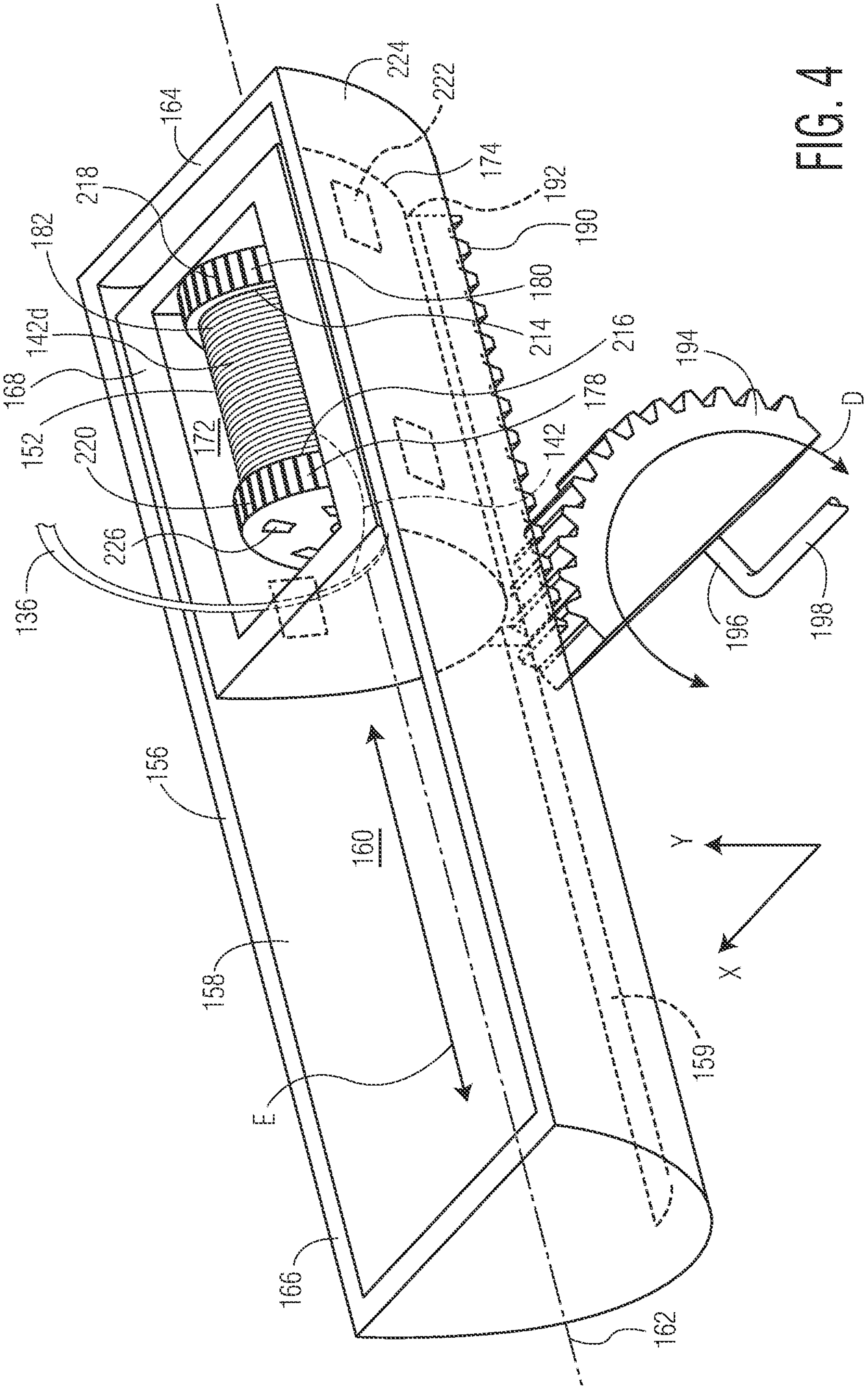
FIG. 4 is a partial cutaway perspective view of embodiments of a fixed bobbin channel, a bobbin carrier and a bobbin in a rest position, and a curved suturing needle assembly, of the handheld medical suturing device, in accordance with embodiments of the invention.

In yet another embodiment, the handheld medical suturing device 100 further includes a fixed bobbin channel 156 that preferably has a semi-annular body 158 as exemplified in FIG. 4, which forms a bobbin channel cavity 160 disposed within the distal end 111 of the handle body 102. The semi-annular body 158 defines an elongated slot 159 therethrough, preferably located at the bottom of the semi-annular body 158 of the fixed bobbin channel 156. The semi-annular body 158 has a proximal end 164 opposite a distal end 166, and the bobbin channel cavity 160 has a central axis 162 that is perpendicular to the XY plane (FIGS. 2-4).

The handheld medical suturing device 100 preferably includes a bobbin carrier 168 that is movably fitted within the bobbin channel cavity 160 of the fixed bobbin channel 156. The bobbin carrier 168 preferably has a semi-annular body 170 that forms a bobbin carrier cavity 172 that is sized and configured to closely receive the curved suturing needle assembly 136 in the fully extended position (illustrated in FIGS. 3 and 17). The curved suturing needle assembly 136 is illustrated in a partially extended position in FIG. 4.

Figure 5:
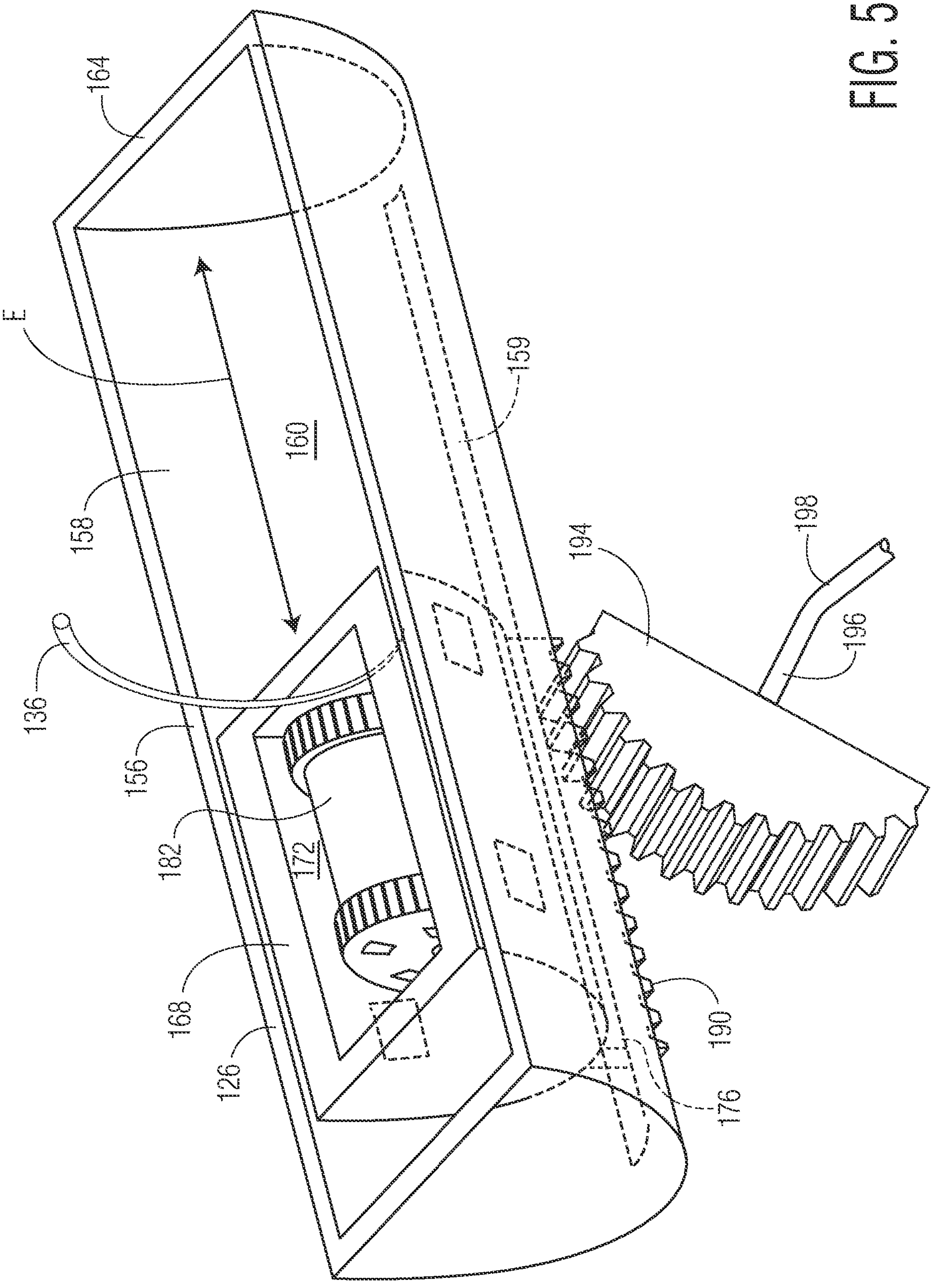
FIG. 5 is a partial cutaway perspective view of embodiments of a fixed bobbin channel, a bobbin carrier and a bobbin in an actuated position, and a curved suturing needle assembly, of the handheld medical suturing device, in accordance with embodiments of the invention.

As illustrated in FIGS. 4-5, the semi-annular body of the bobbin carrier 170 closely aligns with the semi-annular body 158 of the fixed bobbin channel 156.

The bobbin carrier 168 is adapted for movement of the bobbin 152 along the central axis 162 across the XY plane. The bobbin carrier 168 moves between a rest position 174 (FIG. 4) and an actuated position 176 (FIG. 5), as the bobbin 152 is rotatably disposed within the bobbin carrier cavity 172 of the bobbin carrier 168.

As exemplified in FIGS. 4-5, the bobbin carrier 168 of the handheld medical suturing device 100 comprises a rack 190 fixed to and disposed along a bottom of the bobbin carrier 168. Preferably, the rack 190 is preferably molded as part of the bobbin carrier 168. The rack 190 is operatively fitted within the elongated slot 159 of the bottom 192 of the fixed bobbin channel 156. As such, the rack 190 can slide back and forth along the elongated slot 159, in the direction of Arrow E.

Figure 6:
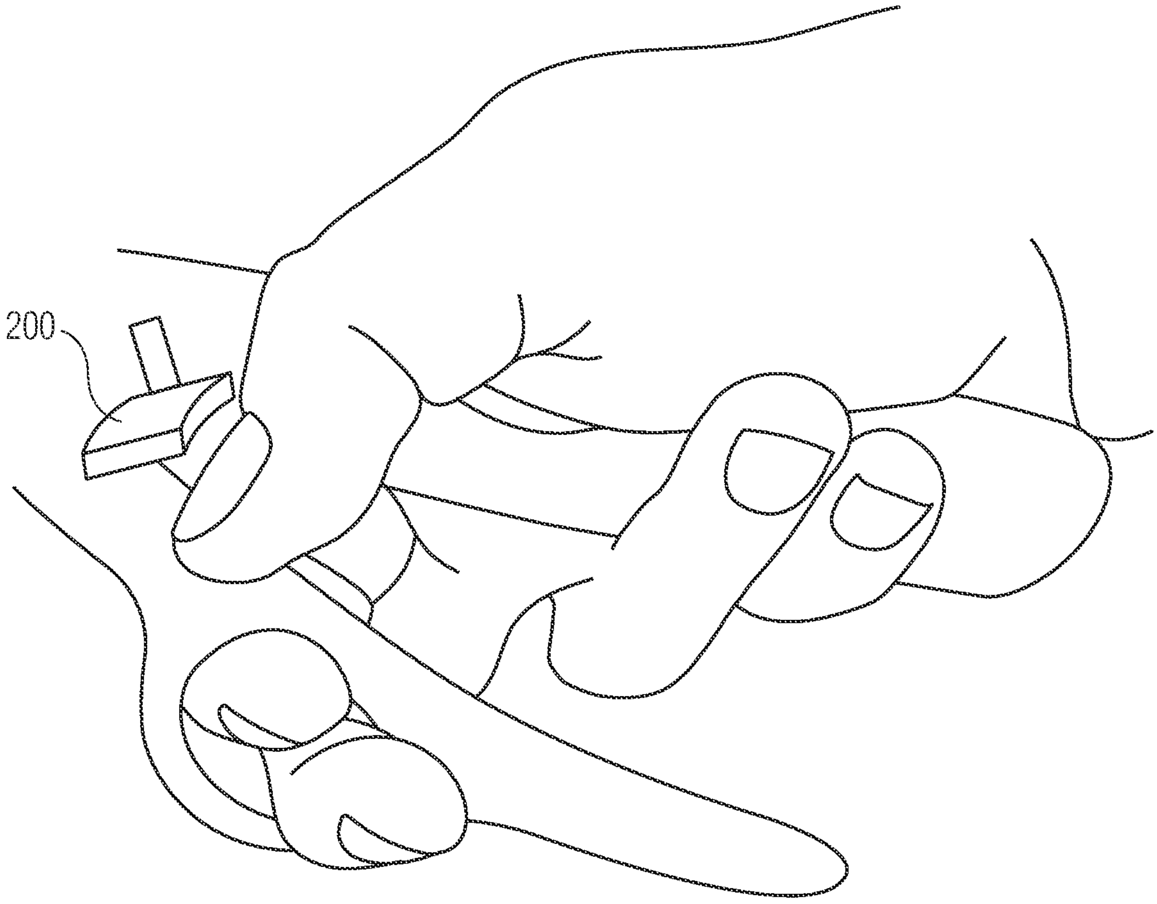
FIG. 6 is a partial cutaway perspective view of a curved suturing needle assembly showing an exemplary user's hand grasping the curved suturing needle assembly, in accordance with embodiments of the invention.
Figure 7:
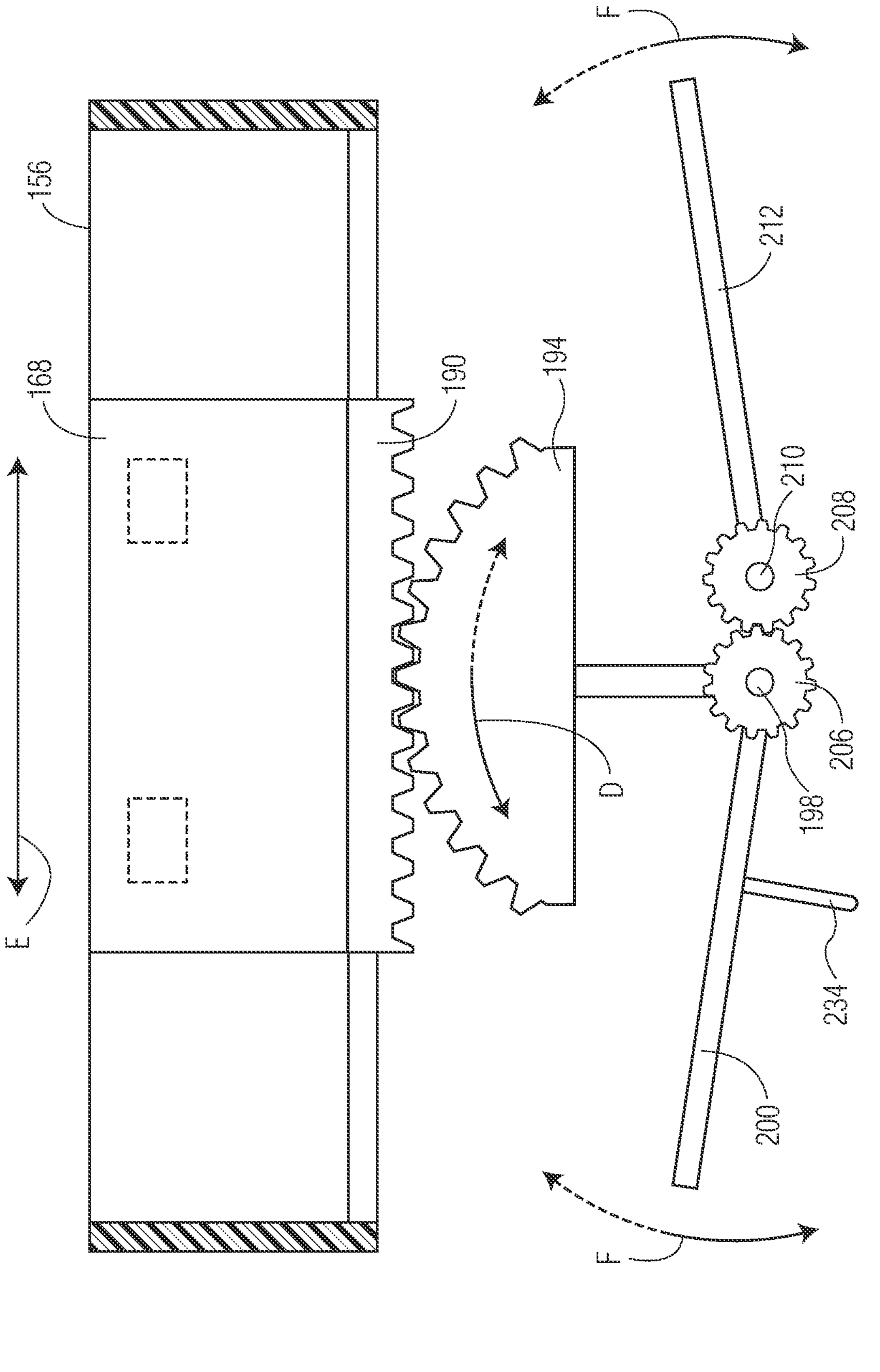
FIG. 7 is a rear partial cutaway cross-sectional view of embodiments of a fixed bobbin channel, a bobbin carrier, a mutilated spur gear engaging a rack, a first thumb lever, a second thumb lever and a respective first drive gear and a respective second drive gear, of the handheld medical suturing device, in accordance with embodiments of the invention.
Figure 8:
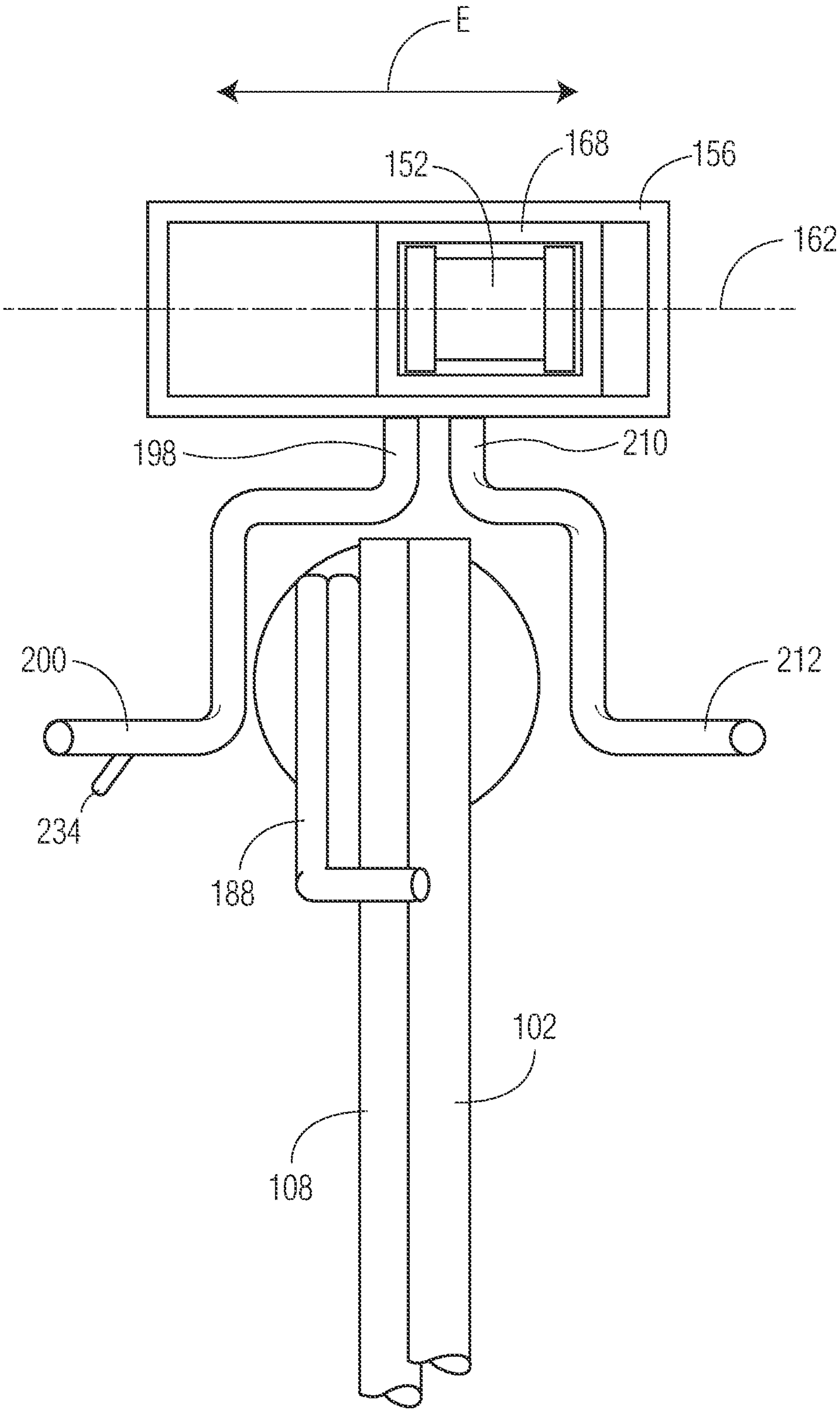
FIG. 8 is a top partial cutaway cross-sectional view of a handheld medical suturing device showing a first thumb lever in a first thumb lever first position, in accordance with embodiments of the invention.
Figure 9:
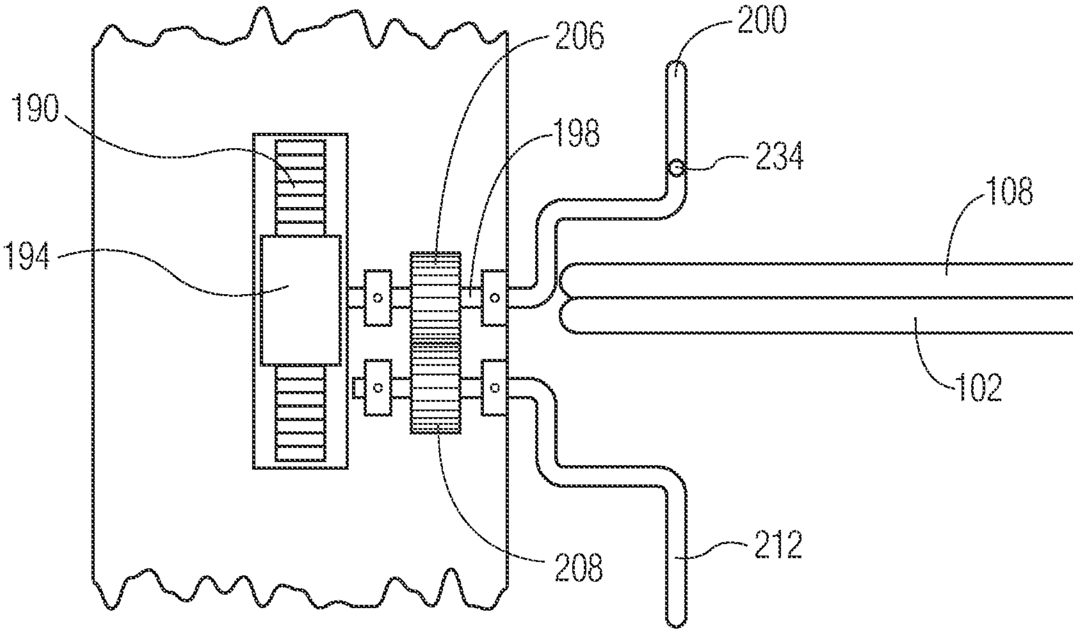
FIG. 9 is a bottom partial cutaway cross-sectional view of a handheld medical suturing device showing a first thumb lever in a first thumb lever first position, in accordance with embodiments of the invention.
Figure 10:
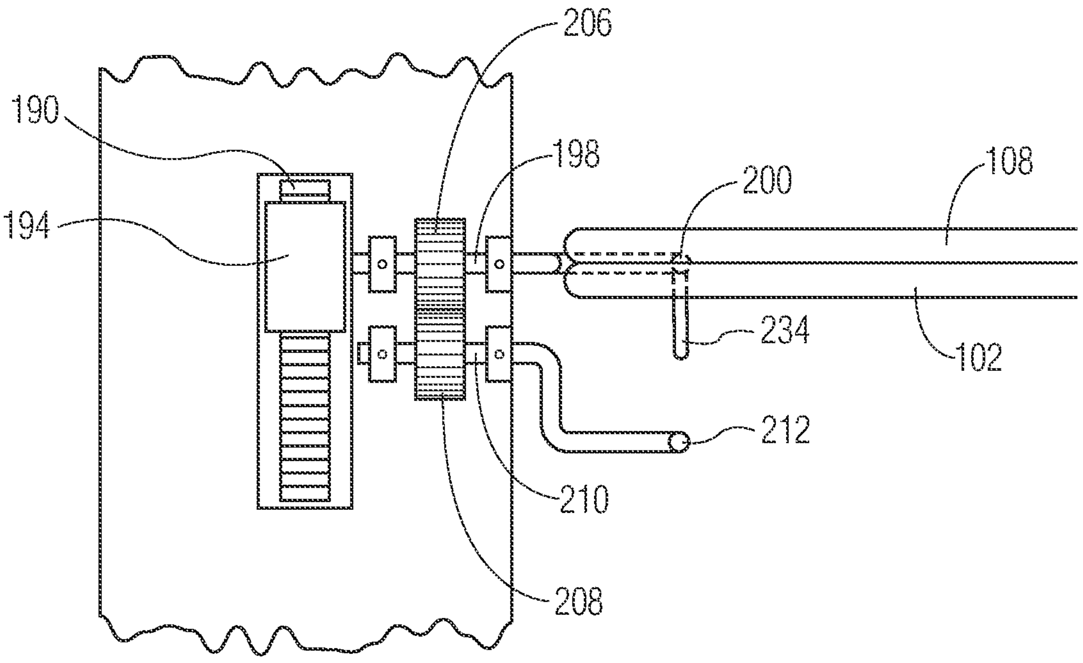
FIG. 10 is a bottom partial cutaway cross-sectional view of a handheld medical suturing device showing a first thumb lever in a first thumb lever second position, in accordance with embodiments of the invention.
Figure 11:
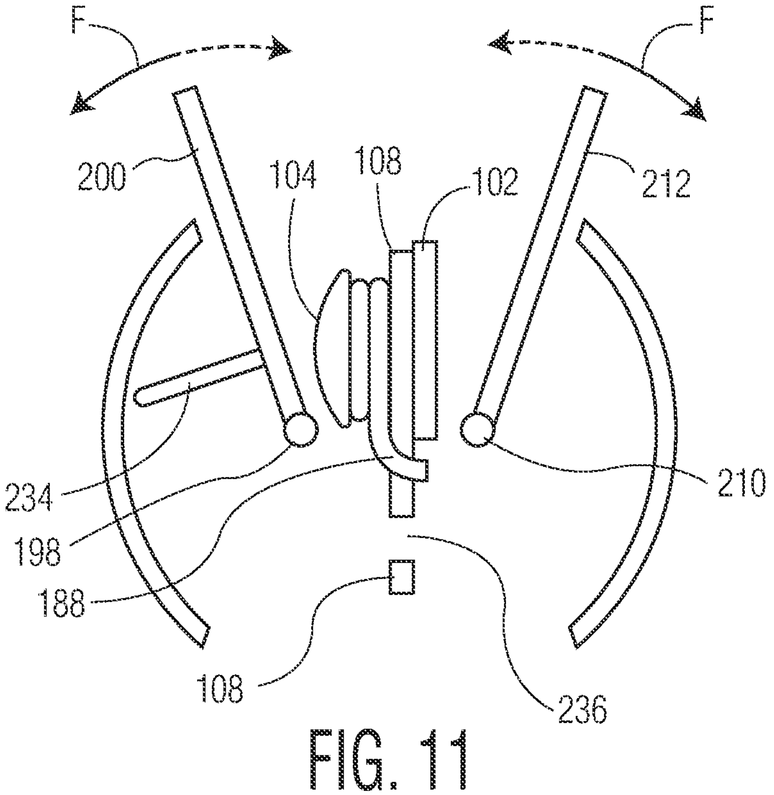
FIG. 11 is rear partial cutaway cross-sectional view of embodiments of a handheld medical suturing device, showing the first thumb lever in a first thumb lever first position, and showing a second thumb lever in a second thumb lever first position, in accordance with embodiments of the invention.
Figure 12:
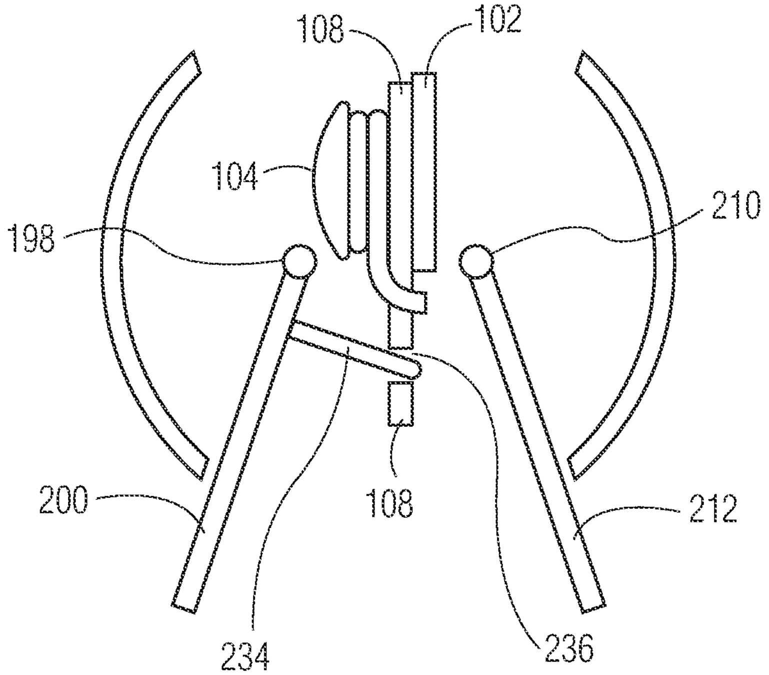
FIG. 12 is rear partial cutaway cross-sectional view of embodiments of a handheld medical suturing device, showing the first thumb lever in a first thumb lever second position, and showing the second thumb lever in a second thumb lever second position, in accordance with embodiments of the invention.

Referring to FIGS. 4-12, in a preferred embodiment, the handheld medical suturing device 100 preferably includes a mutilated spur gear 194 that is fixed to a first drive axle 198 by an arm 196. The first drive axle 198 is connected to a first thumb lever 200 that extends outwardly of the handle body 102, as shown in FIG. 6, for example. A rotation of the first thumb lever 200 (in the direction of Arrow F in FIG. 11) causes the first drive axle to rotate the mutilated spur gear 194, as exemplified in FIG. 7, from a first thumb lever first position, as illustrated in FIGS. 2, 7, 8, 9, and 11, to a first thumb lever second position, as illustrated in FIGS. 10 and 12.

Upon such rotation of the first thumb lever 200, the mutilated spur gear 194 operatively engages the rack 190 to translate and impart rotational motion, in the direction of Arrow D, of the mutilated spur gear 194 into linear motion, in the direction of Arrow E (FIGS. 4-5 and 7-8), of the rack 190 from the rest position 174 to the actuated position 176, upon the rotation, in the direction of Arrow F, of the first thumb lever 200 from a first thumb lever first position (as illustrated in FIGS. 2, 7, 8, 9, and 11) to a first thumb lever second position (as illustrated in FIGS. 10 and 12). The linear motion (Arrow E) of the rack 190 moves the bobbin carrier 168 and the bobbin 152 side to side in the direction of Arrow E within the fixed bobbin channel 156.

As exemplified in FIGS. 4-5, in a preferred embodiment, the bobbin 152 of the handheld medical suturing device 100 has opposing hemispherical heads 214, 216 and a cylindrical body 182, which is preferably at least substantially cylindrical in shape, that serves as an axle disposed between such opposing hemispherical heads 214, 216. That axle contains the suture between the opposing hemispherical heads 214, 216.

In another embodiment, the head of the bobbin 152 is in the form of a hemispherical head, and a side wall of the hemispherical head of the bobbin 152 defines an orifice that is disposed at a central tip of the hemispherical head, where suture is dispensed from within the bobbin 152 through the orifice.

The substantially cylindrical body 182 releases the suture 142 therefrom upon the movement of the bobbin carrier 168 from the rest position 174 to the actuated position 176, in the direction of Arrow E, such that the bobbin 152 is moved across the XY plane, preferably when the curved needle suturing assembly 136 is in the fully extended position (FIGS. 3 and 17). The movement of the bobbin carrier 168 across the XY plane (FIGS. 2-4) moves the suture 142 through a bow 143 that is formed by the suture extending from the curved suturing assembly 136, as illustrated in FIGS. 42-45 and 52.

Figure 40:
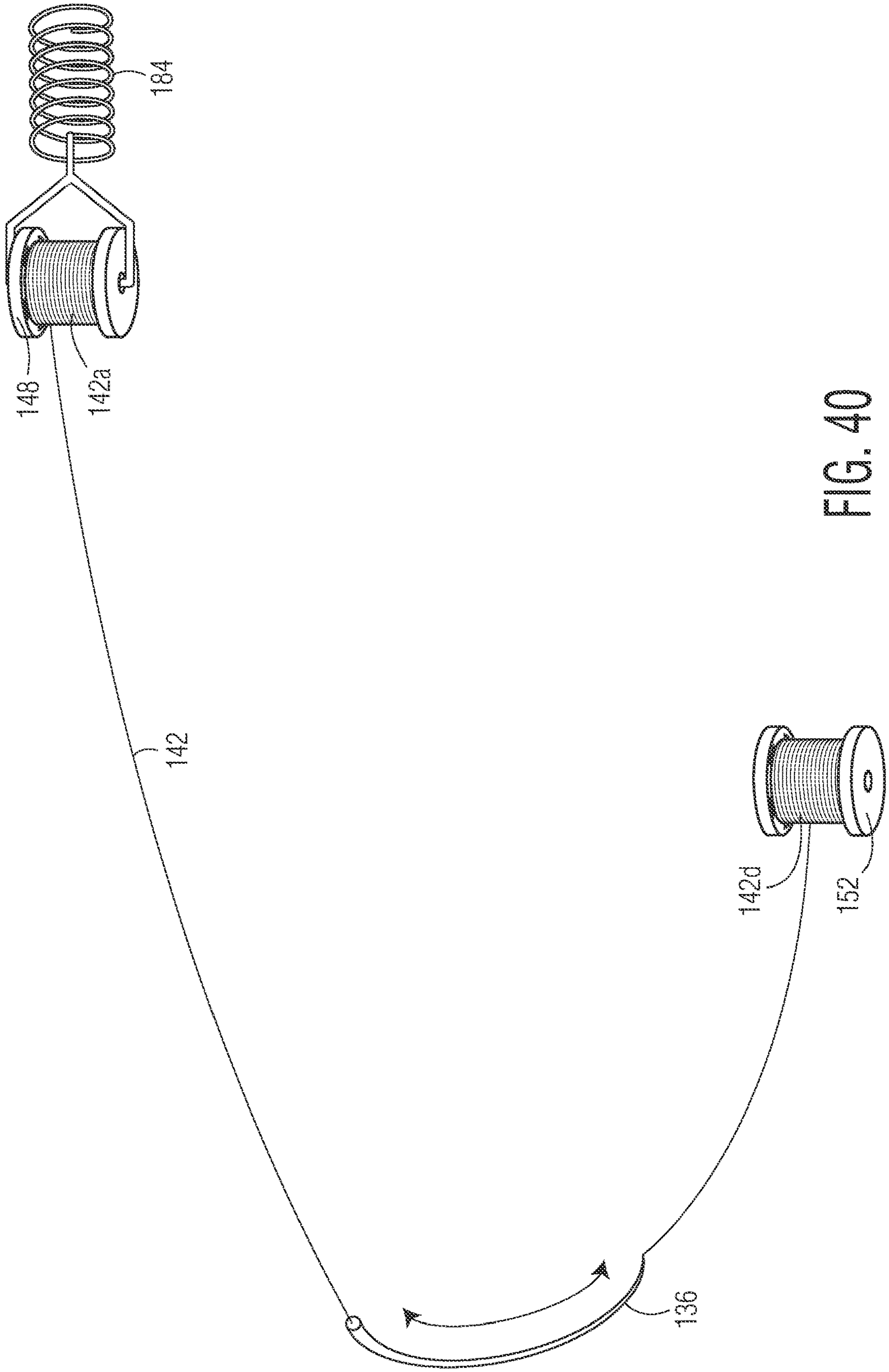
FIG. 40 is a partial cutaway view of a spool, a spring biasing member, a curved suturing needle assembly, and a bobbin of a handheld medical suturing device, in accordance with embodiments of the invention.
Figure 41:
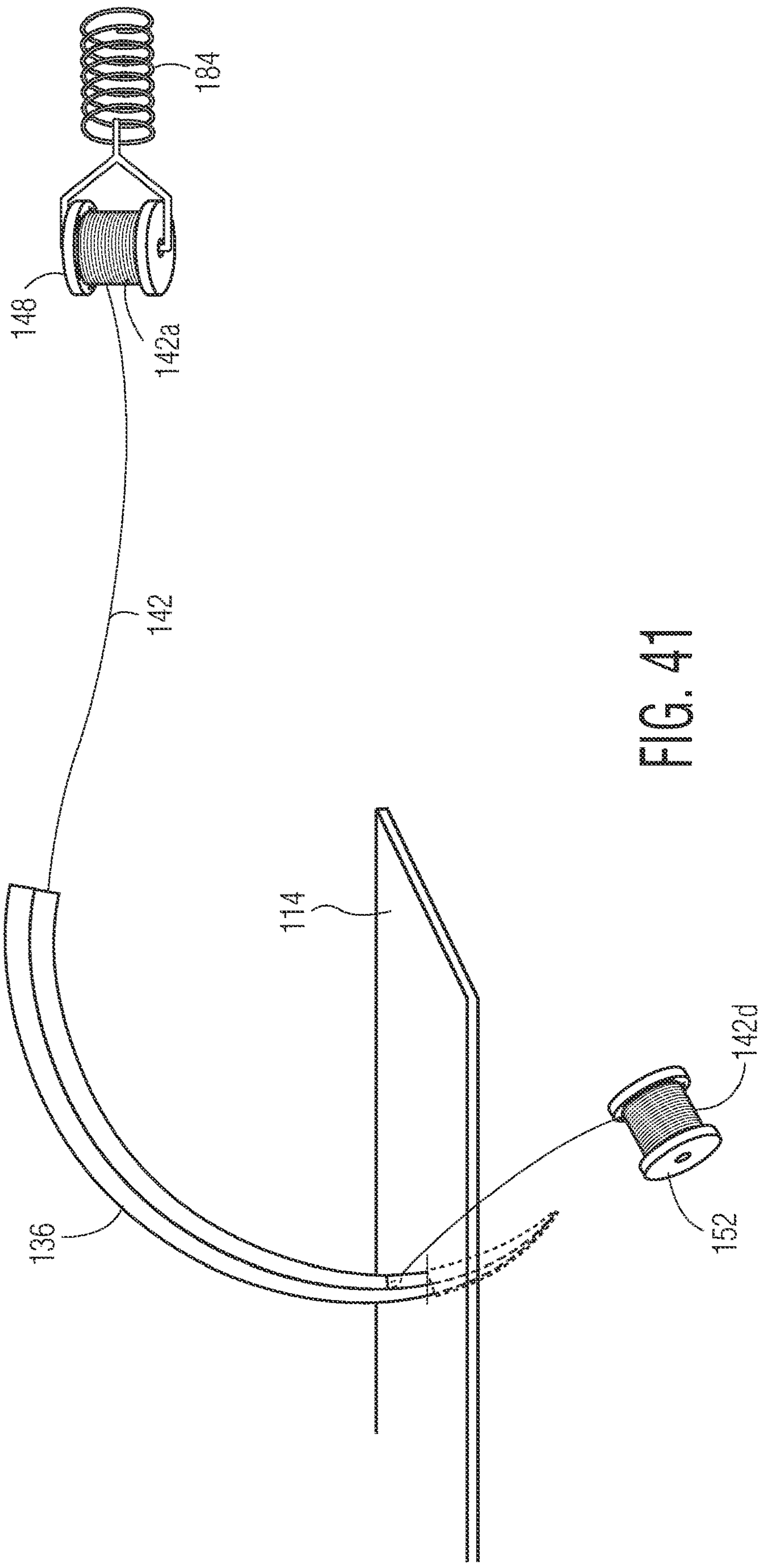
FIG. 41 is a partial cutaway view of a spool, a spring biasing member, a curved suturing needle assembly, a bobbin of a handheld medical suturing device, with an exemplary tissue, in accordance with embodiments of the invention.
Figure 42:
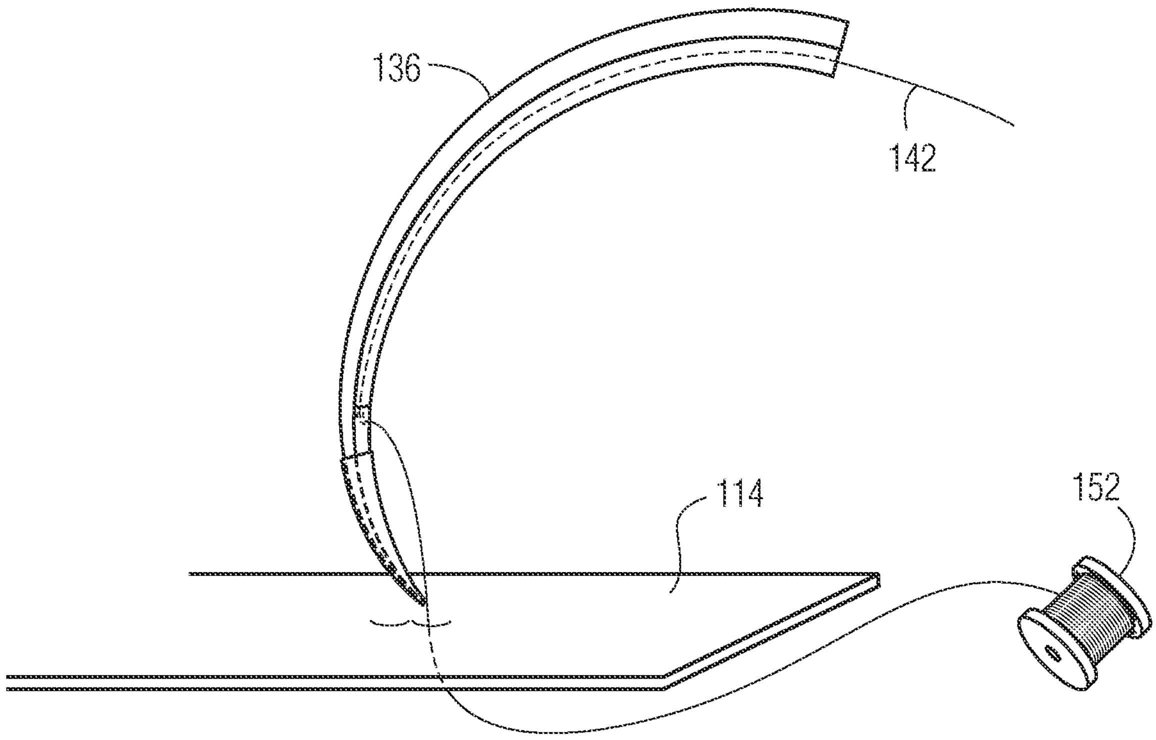
FIG. 42 is partial cutaway view of a curved suturing needle assembly, a suture, and a bobbin of a handheld medical suturing device, with the curved suturing needle assembly positioned to penetrate an exemplary tissue, in accordance with embodiments of the invention.

As illustrated in FIGS. 1-3, the handheld medical suturing device 100 preferably includes at least one spring biasing member 184 that is disposed within the inner cavity passageway 150 of the handle body 102. The spring biasing member 184 is preferably positioned between and connected to the at least one spool 148 and an inner wall 186 of the proximal end 110 of the handle body 102. The at least one biasing member 184 tensions the suture 142 between the at least one spool 148 and the bobbin 152, as exemplified in FIGS. 40-41.

Referring to FIGS. 1 and 11, the handheld medical suturing device 100 further includes at least one spring biasing member 188 that is disposed around the hinge 104 of the handheld medical suturing device 100. The at least one spring biasing member 188 is operatively connected to the handle body 102 and to the distal end 106 of the handle lever 108 at the hinge 104. The at least one biasing member 188 pivotally biases (the proximal end 109) of the handle lever 108 away from the proximal end 110 of the handle body 102 in the direction of Arrow C, illustrated in FIG. 1.

Referring to FIGS. 7-10, in a preferred embodiment, the handheld medical suturing device 100 further comprises a first spur gear 206 that is concentrically disposed around and fixed to the first drive axle 198. The handheld medical suturing device 100 further comprises a second spur gear 208 concentrically disposed around and fixed to a second drive axle 210. The second drive axle 210 is connected to a second thumb lever 212, which extends outward of the handle body 102. The first spur gear 206 operatively engages the second spur gear 208. Similarly, the second spur gear 208 engages the first spur gear 206 to impart rotational movement, in the direction of Arrow F in FIG. 7.

The handheld medical suturing device 100 preferably includes at least one locking pin 234 fixed to the first thumb lever 200. Preferably, the handle lever 108 defines a channel 236 (exemplified in FIGS. 2, 54 and 55), and when the handheld medical suturing device 100 is in the squeezed position (Arrow B of FIGS. 1 and 54) and in the actuated position (FIGS. 5 and 10), a downward rotation of the first thumb lever 200 (in the direction of solid Arrow F in FIG. 11) causes the at least one locking pin 234 to align with that channel 236, as exemplified in FIG. 54, upon such downward rotation of the first thumb lever 200 from the first thumb lever first position, as illustrated in FIGS. 2, 7, 8, 9, and 11, to the first thumb lever second position, as illustrated in FIGS. 10 and 12. When the handle lever 108 is pivoted (re-opened) in the direction of Arrow Cin FIGS. 1 and 55, the locking pin 234 penetrates and slides into the channel 236 of the handle body 108 into a locked position, as exemplified in FIG. 55.

Figure 54:
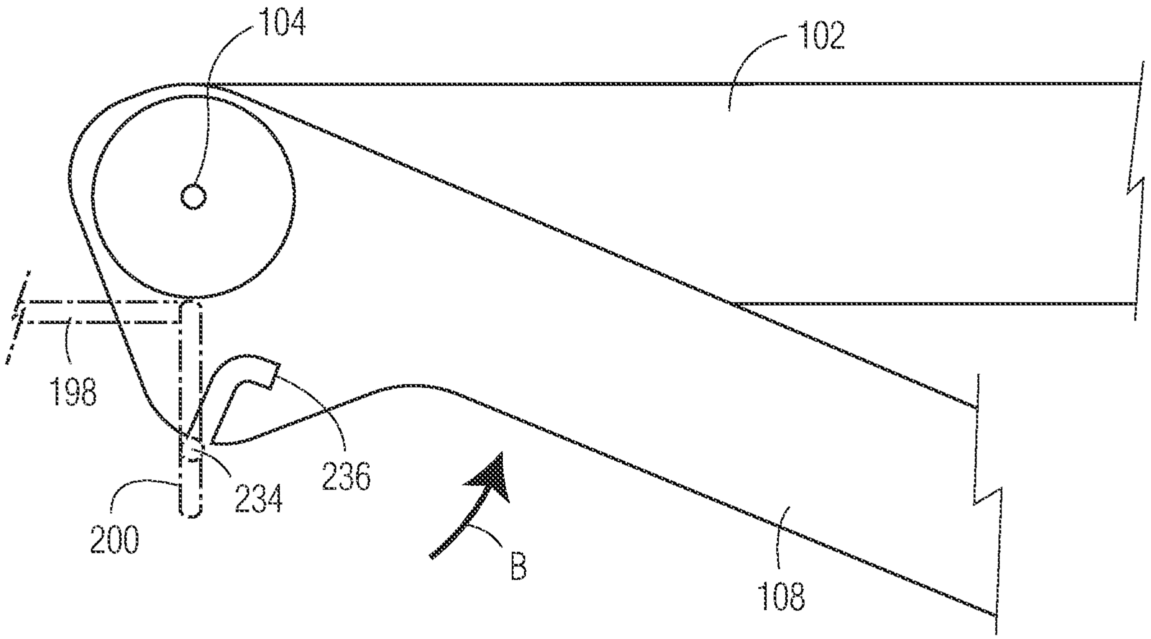
FIG. 54 is a partial cutaway view of a view of a handle body and a handle lever of a handheld medical suturing device, illustrating at least one locking pin aligned with a channel defined by the handle lever, in accordance with embodiments of the invention.
Figure 55:
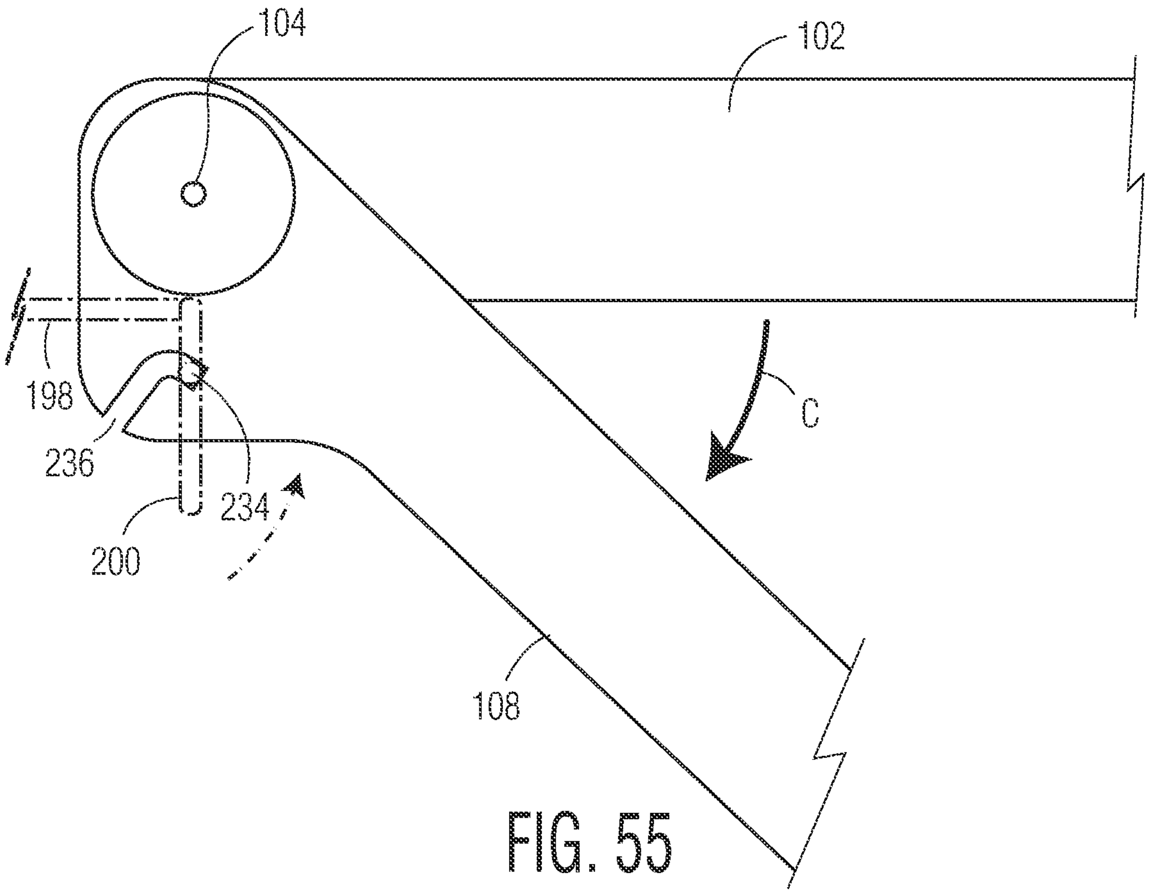
FIG. 55 is a partial cutaway view of a view of a handle body and a handle lever of a handheld medical suturing device, illustrating at least one locking pin penetrated within a channel defined by the handle lever, in accordance with embodiments of the invention.
Figure 56:
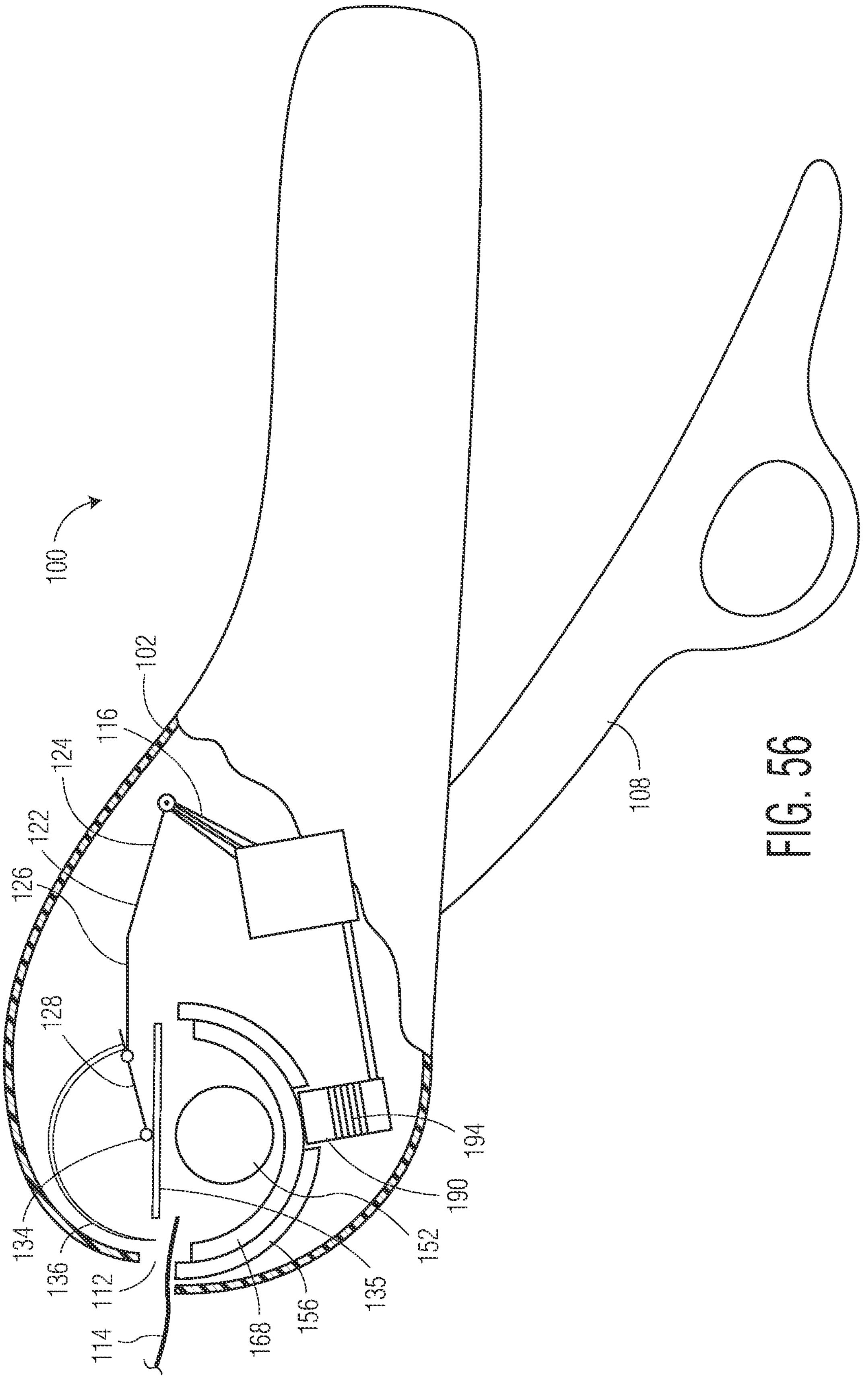
FIG. 56 is a side partial cutaway view of another exemplary handheld medical suturing device in a rest position and showing an exemplary tissue, in accordance with embodiments of the invention.
Figure 57:
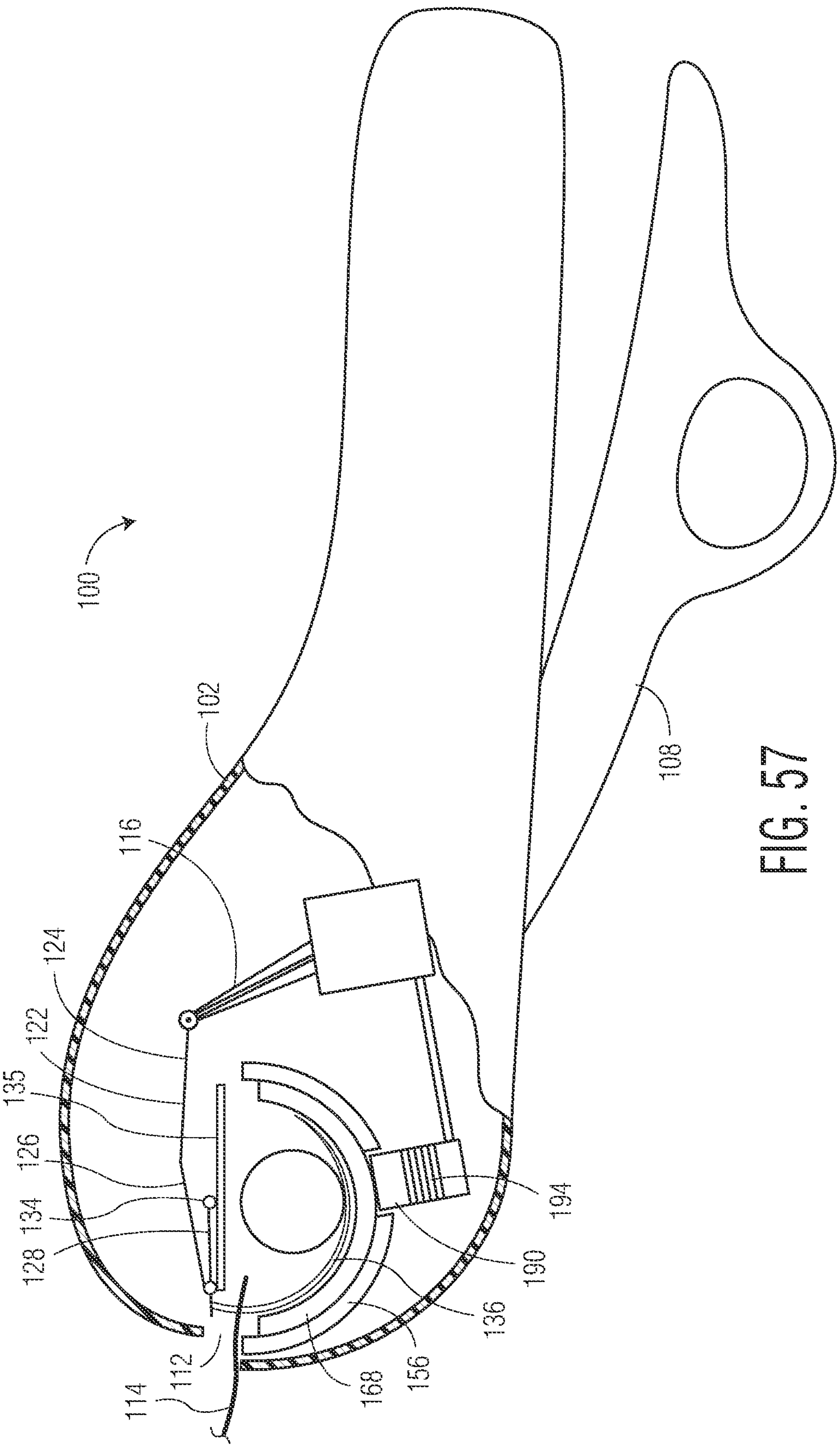
FIG. 57 is a side view, partly cutaway, of the exemplary handheld medical suturing device of FIG. 56 in a fully extended position and showing the exemplary tissue of FIG. 56, in accordance with embodiments of the invention.

Referring to FIGS. 12 and 54-55, such penetration of the locking pin 234 in the channel 236 of the handle body 108 obstructs and prevents a second pivoting (in the direction of Arrow B of FIGS. 1 and 54) of the handle lever 108 relative to the handle body 102 from the open position to the squeezed position, until after the thumb lever 200 has been rotated (dotted Arrow F of FIG. 11) upwardly so as to remove the locking pin 234 from the channel 236 of the handle body 108.

The main purpose of the penetration of the locking pin 234 in the channel 236 is to prevent the handle lever 108 from re-closing (Arrow B) and thus to prevent the curved needle assembly 136 from actuating and penetrating the tissue 114 (FIG. 43) a second time until after the user has rotated the first thumb lever 200 upwardly (dotted Arrow F of FIG. 11), which drives the first drive axle 198 and respective mutilated spur gear 194 to engage the rack 190 and bobbin carrier 168 and impart linear motion, in the direction of Arrow E (FIGS. 4, 5, and 7), of the bobbin carrier 168 from the actuated position 176 (as illustrated in FIG. 5) to the rest position 174 (as illustrated in FIG. 4). An upward rotation (dotted Arrow F of FIG. 11) of the first thumb lever 200 moves the first thumb lever from the first thumb lever second position (as illustrated in FIGS. 10 and 12) to the first thumb lever first position (as illustrated in FIGS. 2, 7, 8, 9, and 11). In other words, the penetration of the locking pin 234 in the channel 236 prevents the handle lever 108 from accidentally or un-intentionally re-closing (Arrow B) (which would cause the curved needle assembly 136 to re-penetrate the tissue 114 (FIG. 43) a second time) until after the user (e.g. the surgeon) has rotated the first thumb lever 200 upwardly (dotted Arrow F of FIG. 11) to move the bobbin 152 across the XY plane to reset and ready the handheld medical suturing device 100 for an intended, second penetration of the tissue 114, as exemplified in FIG. 53.

In such preferred embodiment, the at least one locking pin of the handheld medical suturing device 100 is configured for withdrawal from the channel upon a rotation of the first thumb lever by a user from the first thumb lever second position (as illustrated in FIGS. 2, 7, 8, 9, and 11) to the first thumb lever first position.

The first thumb lever 200 is typically used by a right-handed user grasping the handheld medical suturing device 100. The second thumb lever 212 is typically used by a left-handed user grasping the handheld medical suturing device 100.

As noted above, referring to FIGS. 7-12, there is preferably a second thumb lever 212, which extends outwardly of the handle body 102, and the second thumb lever 212 is connected to the second drive axle 210 which has a second spur gear 208 that operatively engages the first spur gear 206, to impart rotational movement, in the direction of Arrow F in FIG. 7. A rotation of the second thumb lever 212 causes the second spur gear 208 to rotate the first spur gear

206. Accordingly, a downward rotation of the second thumb lever 212 (in the direction of solid Arrow F in FIG. 11) causes the at least one locking pin 234 to align with the channel 236, as exemplified in FIG. 54, upon such downward rotation of the second thumb lever 212 from the second thumb lever first position, as illustrated in FIGS. 2, 7, 8, 9, and 11, to the second thumb lever second position, as illustrated in FIGS. 10 and 12. When the handle lever 108 is pivoted (re-opened) in the direction of Arrow C in FIGS. 1 and 55, the locking pin 234 penetrates and slides into the channel 236 of the handle body 108 into a locked position, as exemplified in FIG. 55.

Moreover, since the second spur gear 208 engages the first spur gear 206, then a rotation of the second thumb lever 212 causes the mutilated spur gear 194 to operatively engages the rack 190 to translate and impart rotational motion, in the direction of Arrow D, of the mutilated spur gear 194 into linear motion, in the direction of Arrow E, of the rack 190 from the rest position 174 to the actuated position 176, upon the rotation, in the direction of Arrow F, of the second thumb lever 212 from a second thumb lever first position (as illustrated in FIGS. 2, 7, 8, 9, and 11) to a second thumb lever second position (as illustrated in FIGS. 10 and 12). The linear motion (Arrow E) of the rack 190 moves the bobbin carrier 168 and a bobbin 152 side to side in the direction of Arrow E within the fixed bobbin channel 156.

As can be appreciated from this description, the mutilated spur gear 194 operatively engages the rack to translate its rotational motion into linear motion of the rack upon rotation of either the first thumb lever 206 or the second thumb lever 212. The linear motion of the rack 190 moves the bobbin carrier 168 and the bobbin 152 side to side within the bobbin channel.

In a preferred embodiment, the handheld medical suturing device 100 further comprises at least one spool 148 of suture 142 that is disposed within an inner cavity passageway 150 that is defined by the proximal end 110 of the handle body 102. The suture 142 is preferably threaded from the at least one spool 148 through the inner cavity passageway 150 to the curved suturing needle assembly 136. The suture 142 is further threaded from the curved suturing needle assembly 136 to the bobbin 152 that is disposed within the distal end 111 of the handle body 102. The at least one spool 148 is adapted to dispense the suture 142 to the curved suturing needle assembly 136 upon the rotation of the curved suturing needle 136 by a user from the retracted position (as illustrated in FIGS. 1 and 15) to the fully extended position (as illustrated in FIGS. 3 and 17), upon the pivoting of the handle lever 108 (in the direction of Arrow B in FIG. 18) relative to the handle body 102 from the open position (as illustrated in FIGS. 1, 2, and 15) to the squeezed position (as illustrated in FIGS. 3 and 17).

As illustrated in FIGS. 4-5, the bobbin 152 has a proximal end 214 opposite a distal end 216, and the proximal end 214 preferably includes a first plurality of annularly disposed ridges 218 that provide a first frictional resistance against rotation of the bobbin 152 within the bobbin carrier 168 in order to keep the suture 142 taut, as the curved suturing needle assembly 136 is actuated and penetrates through the tissue 114, between the retracted position and the fully extended position, upon the pivoting of the handle lever 108 (Arrow B) relative to the handle body 102. Such frictional resistance of the first plurality of annularly disposed ridges 218 also maintains tension 142 on the suture upon the movement of the bobbin 152 along the central axis across the XY plane between a rest position 174 and an actuated position 176.

In another preferred embodiment, the distal end 216 of the bobbin 152 preferably includes a second plurality of annually disposed ridges 220 that provide a second frictional resistance against rotation of the bobbin 152 within and relative to the bobbin carrier 168, upon the rotation of the curved suturing needle assembly 136 through the tissue between the retracted position and the fully extended position, upon the pivoting of the handle lever (Arrow B) relative to the handle body 102. Such second frictional resistance is also maintains tension on the suture 152 upon a user's movement of the bobbin 152 along the central axis across the XY plane (FIG. 4) between the rest position 174 and the actuated position 176.

Referring to FIG. 4, in yet another embodiment, the handheld medical suturing device 100 has at least one magnet 222 disposed within a wall 224 of the bobbin carrier 168, in a spaced relation to the bobbin 152, and the bobbin 152 comprises a ferrous material 226 that provides a magnetic attraction which provides a magnetic resistance against rotation of the bobbin 152 relative to the bobbin carrier 168, in order to keep the suture taut. Such magnetic resistance imparts tension on the suture 142.

Figure 13:
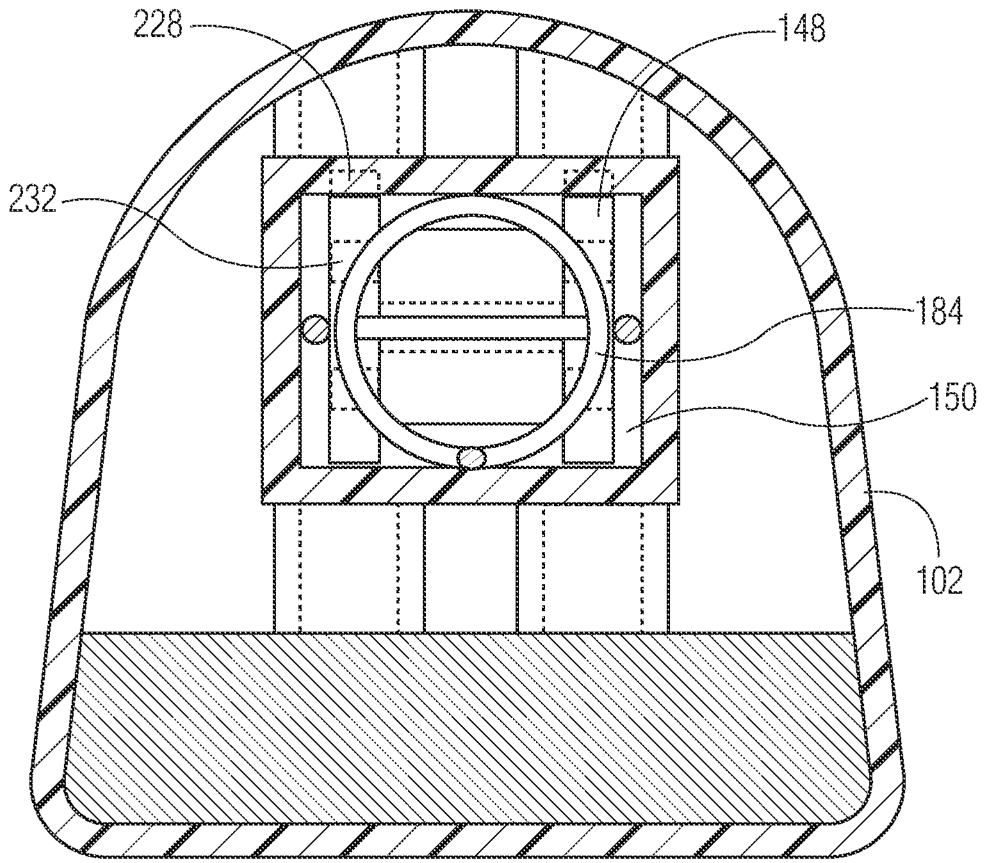
FIG. 13 is a cross sectional view along the cutting view 13-13 of FIG. 1, of embodiments of a handheld medical suturing device, in accordance with embodiments of the invention.
Figure 14:
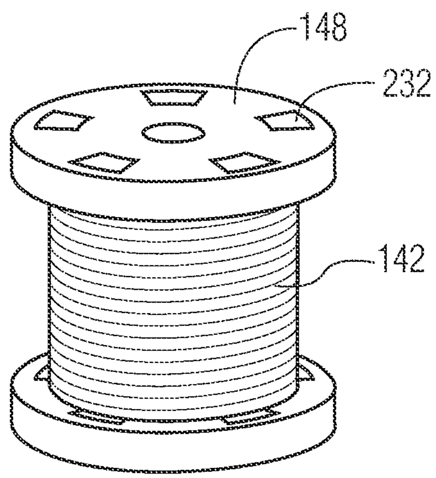
FIG. 14 is a perspective view of a spool of a handheld medical suturing device, in accordance with embodiments of the invention.

Referring to FIGS. 13-14, in another embodiment, the handheld medical suturing device 100 preferably includes at least one magnet 228 that is disposed within a wall 230 of the handle body 102, and the handheld medical suturing device 100 further comprises at least one spool 148 of suture that is disposed within the inner cavity passageway 150 that is defined by the proximal end 110 of the handle body 102. The at least one spool 148 preferably includes a ferrous material 232 that is adapted to provides a magnetic attraction to said at least one magnetic disc 228 which provides magnetic resistance against rotation of the at least one spool 148 relative to the wall of the handle body 102, in order to keep the suture 142 taut.

In another embodiment, the handheld medical suturing device includes at least one frictional compression disc disposed in the handle body between the at least one spool 148 and an adjacent wall of the handle body. The at least one frictional compression disc provides frictional resistance against rotation of the at least one spool 148 to provide tension on the suture 142, to help keep the suture 142 taut.

In a preferred embodiment, the handheld medical suturing device 100 includes at least one spool 148 of suture 142 disposed within the inner cavity passageway 150 defined by the proximal end 110 of the handle body 102, where suture 142 is threaded from that at least one spool 148 through the inner cavity passageway 150 to the curved suturing needle assembly 136, and the suture 142 is further threaded from the curved suturing needle assembly 136 to the bobbin 152 that is disposed within the distal end 110 of the handle body 102, as illustrated in FIG. 2. The at least one spool 148 is adapted to dispense the suture 142 to the curved suturing needle assembly 136 upon the rotation (Arrow A) of the curved suturing needle assembly 136 from the retracted position (as illustrated in FIGS. 1 and 15) to the fully extended position (as illustrated in FIGS. 3 and 17).

Referring to FIGS. 20-28, in a preferred embodiment, the curved suturing needle assembly 136 of the handheld medical suturing device 100 comprises an outer curved needle 238 fixed to an inner curved needle 240. The outer curved needle 238 has a proximal end 242 opposite a distal end 244. The inner curved needle 240 has a proximal end 246 opposite a distal end 248. The curved suturing needle assembly 136 preferably includes a shroud 250 that is disposed along an outer surface 252, 254 of the outer curved needle 238 and of the inner curved needle 240, as illustrated in FIGS. 20-22 and 28. The shroud forms a passage 256 for the suture 142 to thread therethrough.

Figure 31:
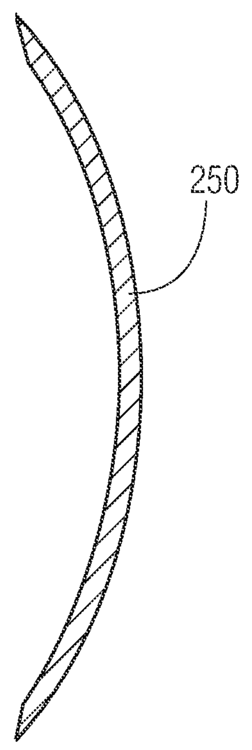
FIG. 31 is a cross sectional view along the cutting view 31-31 of FIG. 20, in accordance with embodiments of the invention.
Figure 32:
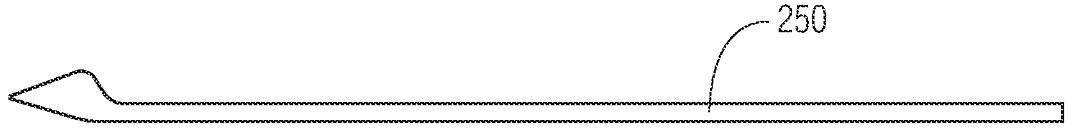
FIG. 32 is a top partial cutaway view of a shroud of a curved needle suturing assembly, in accordance with embodiments of the invention.

The shroud 250 includes a pointed cover 258 encapsulating the distal end 244 of the outer curved needle 238, as seen in FIGS. 20, 25, and 27-30. Apart from the pointed cover 258 encapsulating the distal end 244 of the outer curved needle 238, the shroud primarily comprises a body having a curved cross-section, as illustrated in FIGS. 31-32.

Figure 22:
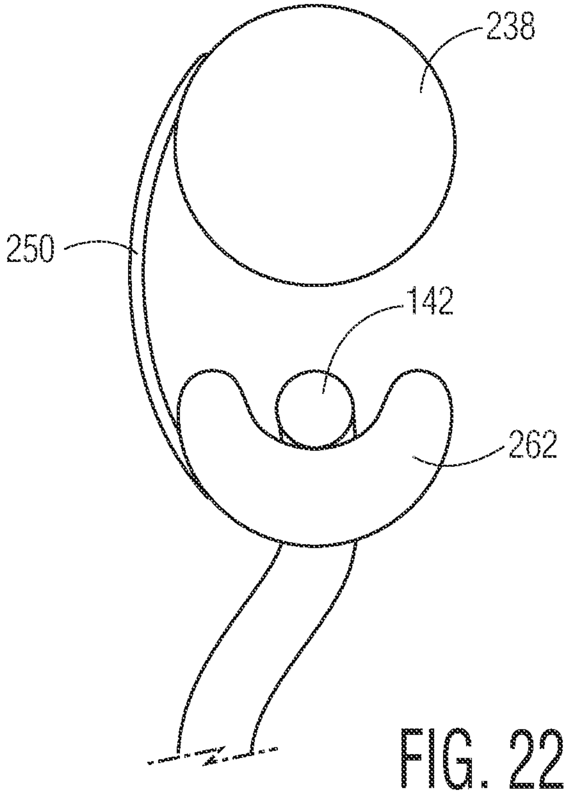
FIG. 22 is a cross sectional view along the cutting view 22-22 of FIG. 20, in accordance with embodiments of the invention.
Figure 23:
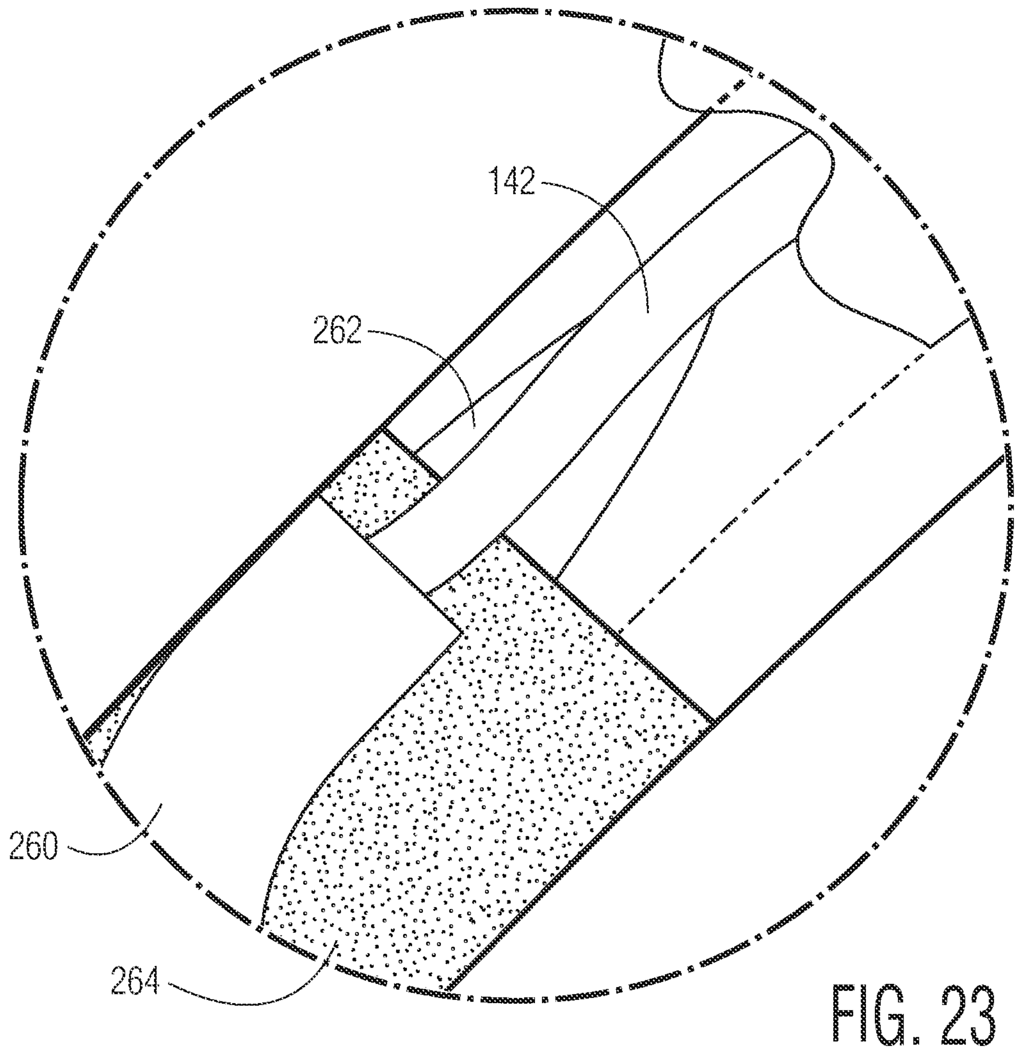
FIG. 23 is a partial cutaway cross-sectional view of a curved needle suturing assembly, in accordance with embodiments of the invention.
Figure 24:
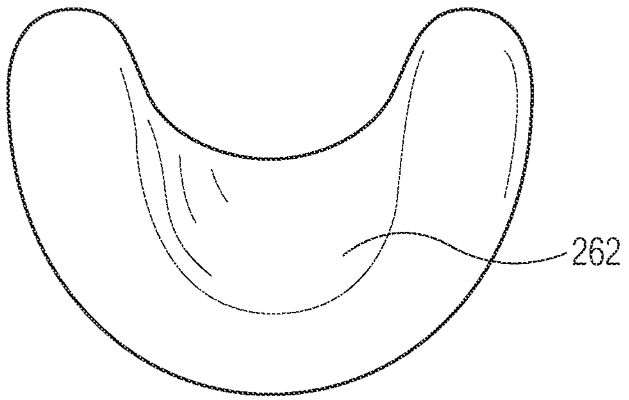
FIG. 24 is a perspective partial cutaway view of a curved needle suturing assembly, in accordance with embodiments of the invention.
Figure 25:
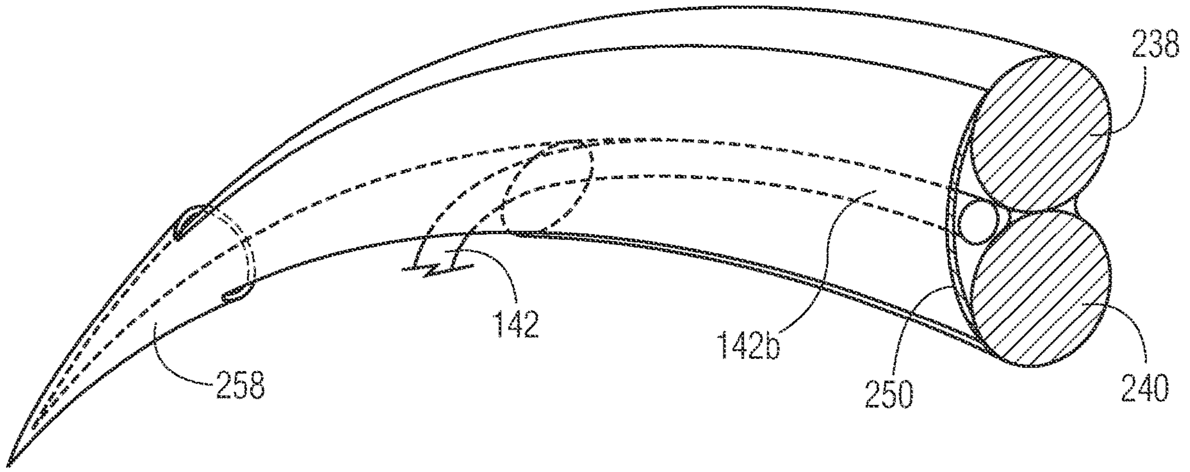
FIG. 25 is a perspective partial cutaway view of embodiments of a curved needle suturing assembly, in accordance with embodiments of the invention.
Figure 26:
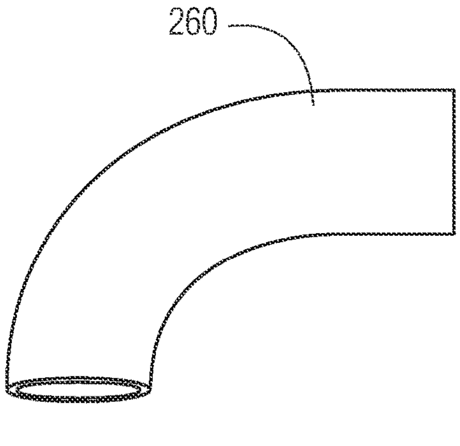
FIG. 26 is a perspective partial cutaway view of an elbow of a curved needle suturing assembly, in accordance with embodiments of the invention.
Figure 27:
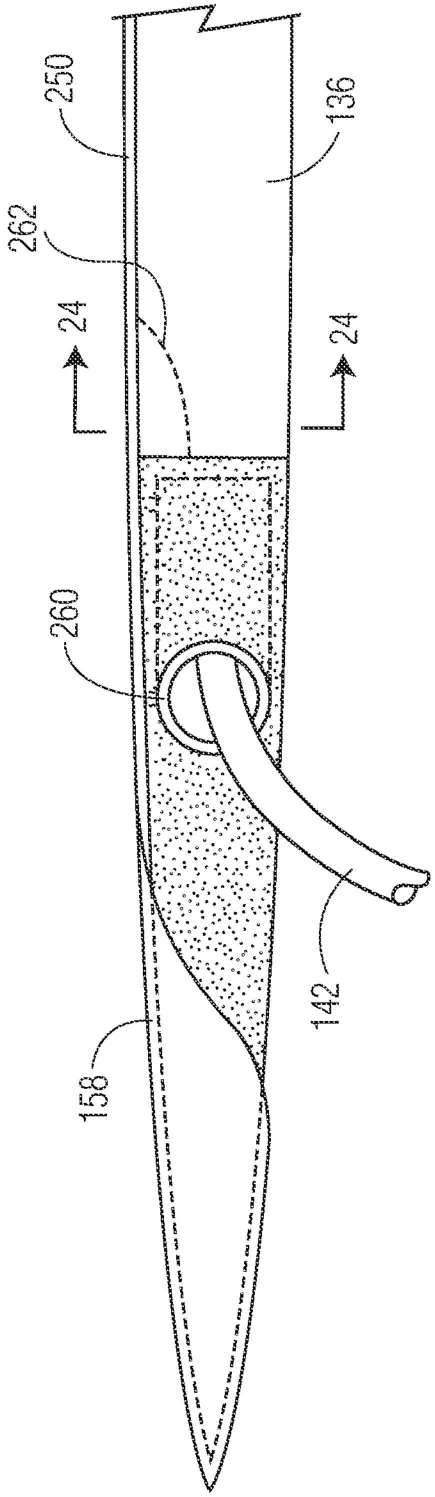
FIG. 27 is a bottom partial cutaway cross-sectional view of a curved needle suturing assembly, in accordance with embodiments of the invention.
Figure 28:
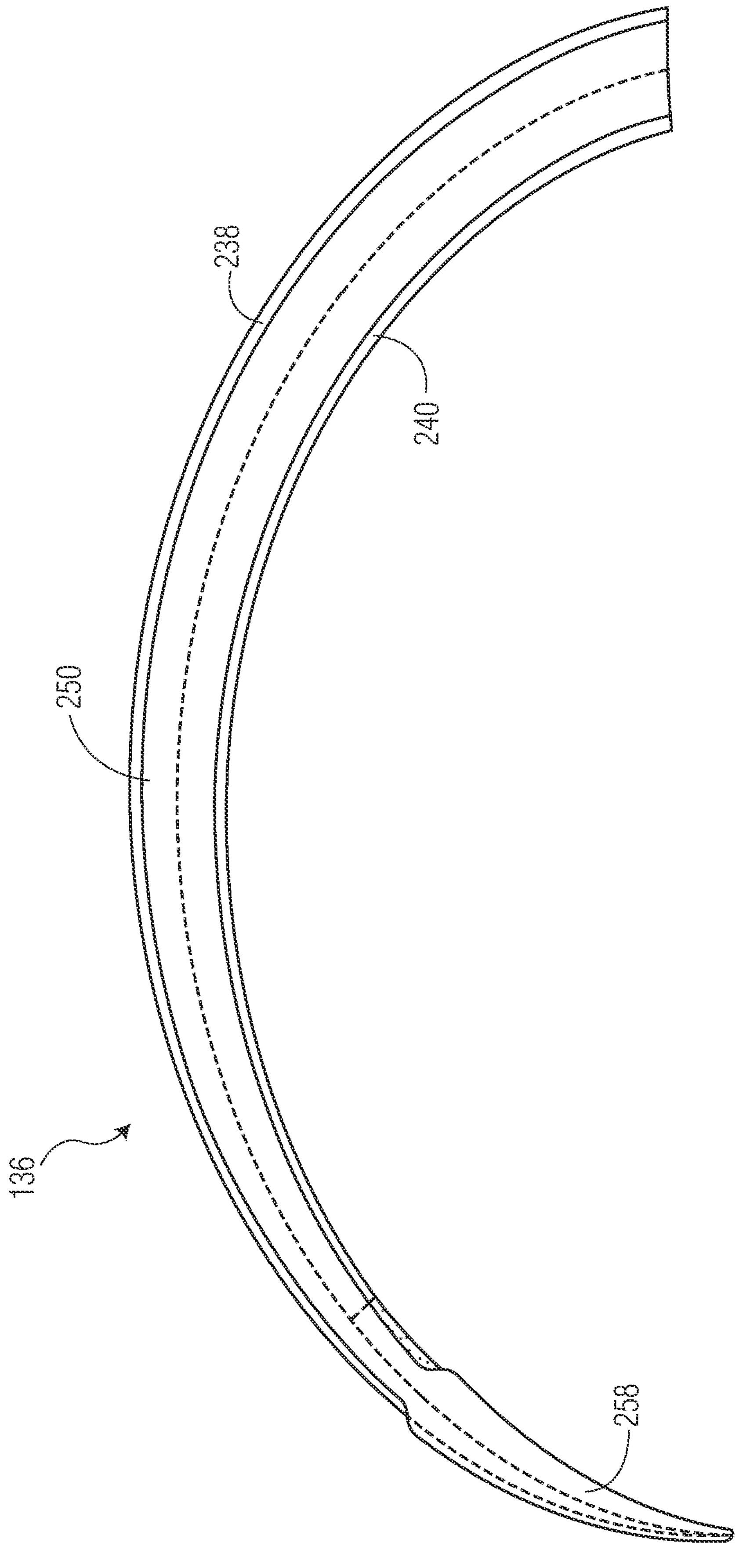
FIG. 28 is a partial cutaway cross-sectional view a curved needle suturing assembly, in accordance with embodiments of the invention.
Figure 29:
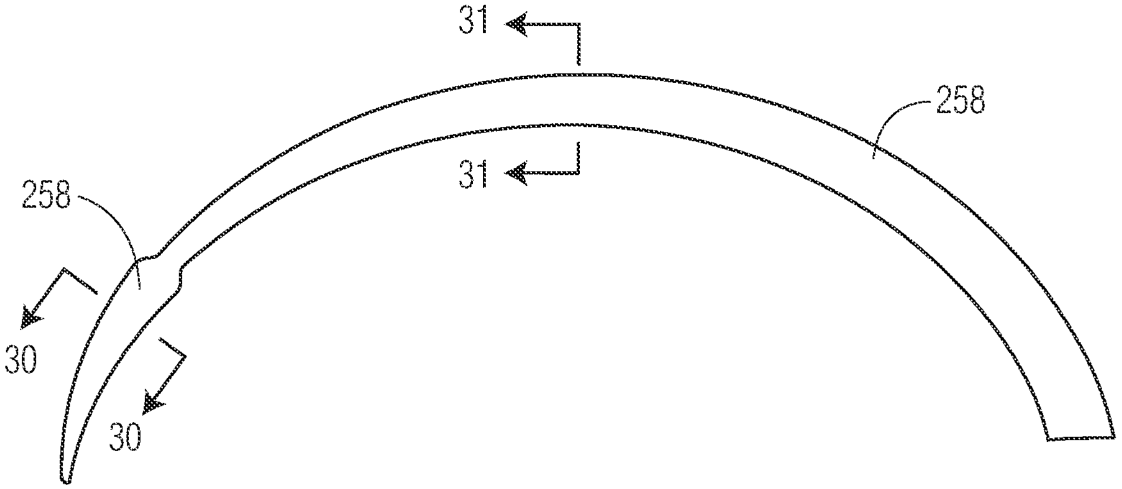
FIG. 29 is a side elevation partial cutaway view of a shroud of a curved needle suturing assembly, in accordance with embodiments of the invention.
Figure 30:
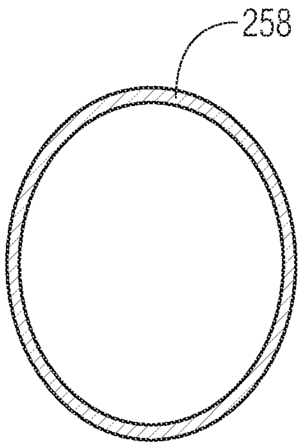
FIG. 30 is a cross sectional view along the cutting view 30-30 of FIG. 29, in accordance with embodiments of the invention.

In yet another preferred embodiment, the handheld medical suturing device 100 includes an elbow guide 260 disposed within the pointed cover 258, as illustrated in FIGS. 20, 23, and 26-27. The elbow guide 260 engages and guides the suture 142 as the suture 142 extends outwardly from and exits the distal end 248 of the inner curved needle 240. Preferably, a filling 264 is provided within the pointed cover 258 of the shroud 250, around the elbow guide 260. As illustrated in FIGS. 22-24, the distal end 248 of the inner curved needle 240 preferably defines a ramp 262 to engagingly guide the suture 142, so as to provide a smooth exit for the suture 142 as it threads out of the inner curved needle 240, as illustrated in FIG. 27.

In a preferred embodiment, the handheld medical suturing device 100 includes a single length of suture 142, where a first portion **142*a* of the single length of suture is disposed around the at least one spool (as illustrated in FIGS. 14), where a second portion 142*b* of the single length of suture is disposed along the curved suturing needle assembly 136 (FIGS. 21 and 25), where a third portion 142*c* of the single length of suture is disposed inside the bobbin carrier cavity (FIG. 1), and where a fourth portion 142*d* of the single length of suture is disposed around the bobbin 152 (FIG. 4). The single length of suture 142 is also exemplified in FIGS. 40-41**.

In another one embodiment, the single length of suture 142 includes a first portion **142*a* of the single length of suture disposed around the at least one spool 148 (FIG. 14), a second portion 142*b* of the single length of suture 142 is disposed within the shroud 250 (FIGS. 21 and 25) of the curved suturing needle assembly 136, a third portion 142*c* of the single length of suture 142 is disposed inside the bobbin carrier cavity 172 (FIG. 4), and a fourth portion 142*d* of the single length of suture 142 is disposed around the bobbin 152 (FIG. 4**).

Figure 33:
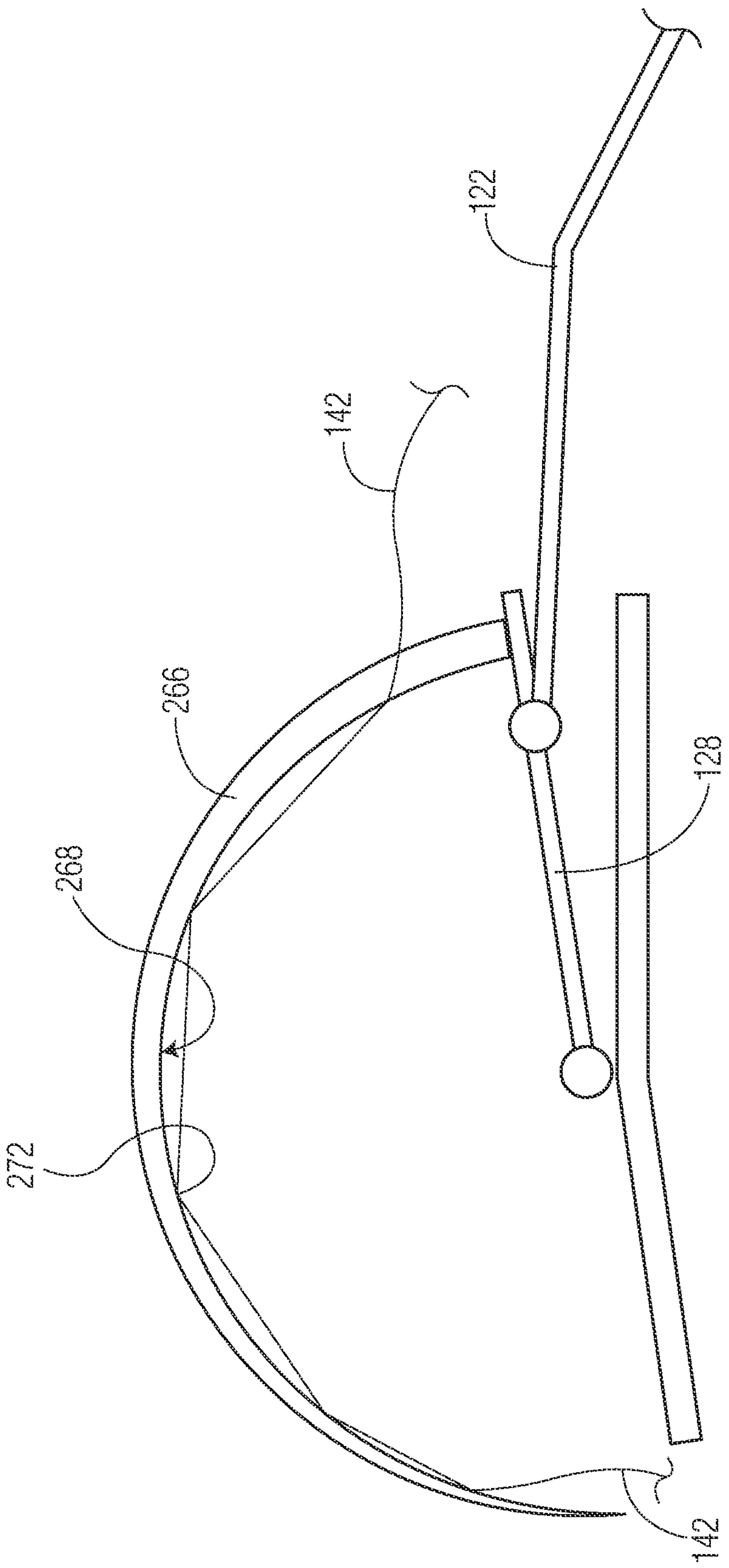
FIG. 33 is partial cutaway cross-sectional view of a handheld medical suturing device, showing a curved needle suturing assembly in a retracted position, in accordance with embodiments of the invention.
Figure 34:
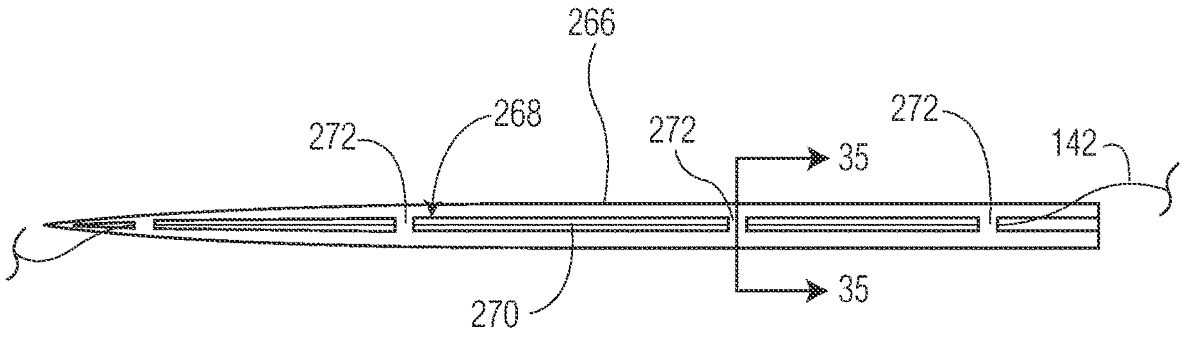
FIG. 34 is a bottom partial cutaway cross-sectional view of a curved needle suturing assembly, in accordance with embodiments of the invention.
Figure 35:
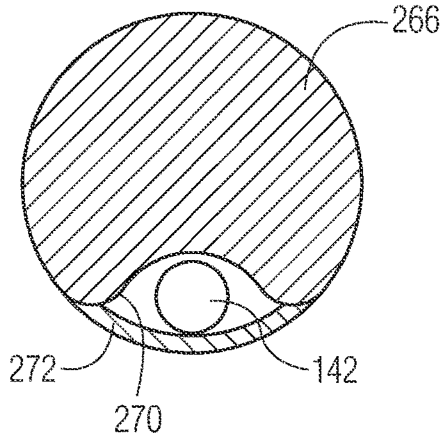
FIG. 35 is a cross sectional view along the cutting view 35-35 of FIG. 34, in accordance with embodiments of the invention.

Referring to FIGS. 33-35, in another embodiment, the curved suturing needle assembly 136 comprises a single curved needle 266 having an inner surface 268 which defines an annular groove 270. The single curved needle 266 preferably has a plurality of containment bridges 272 annularly disposed along the annular groove 270 of the inner surface 268. The plurality of containment bridges 272 maintain the suture 242 within the annular groove 270 of the single curved needle 266, as illustrated in FIGS. 33 and 35.

Figure 36:
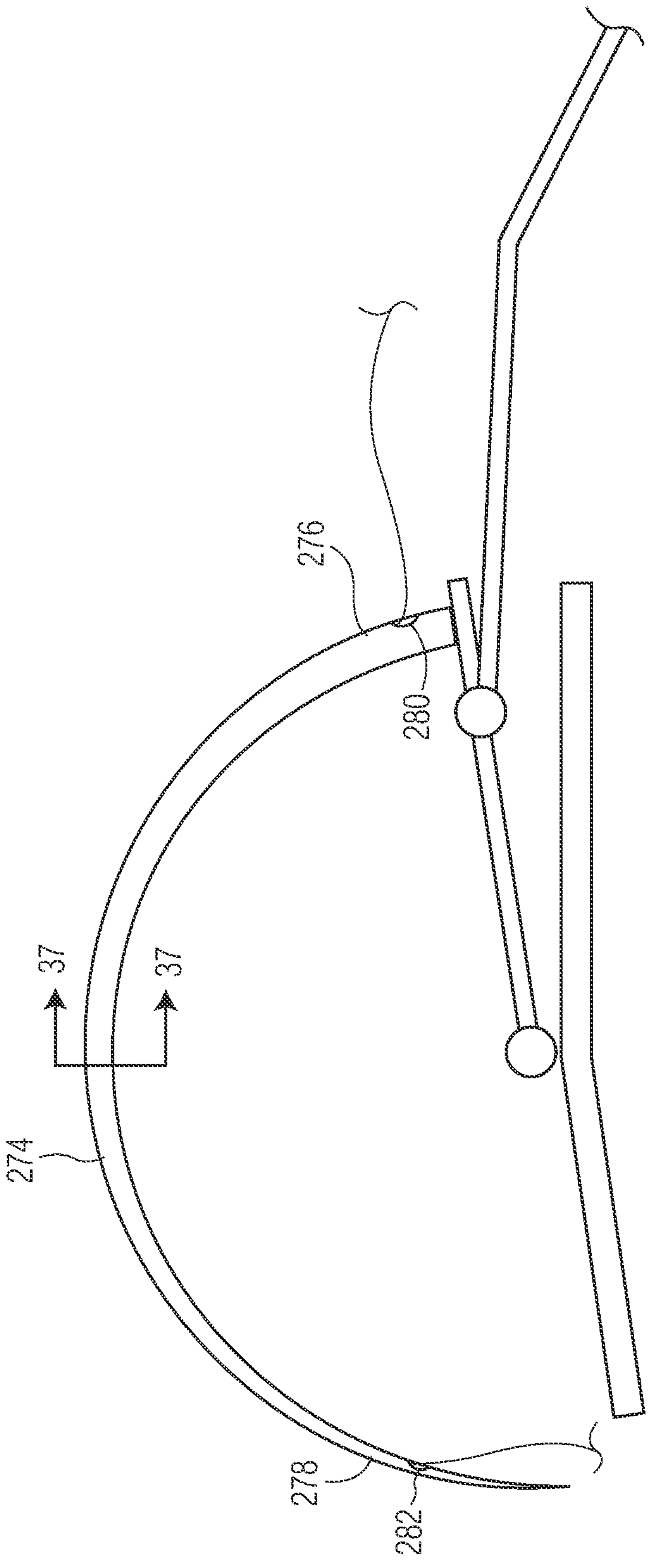
FIG. 36 is a partial cutaway cross-sectional view of a handheld medical suturing device, showing a curved needle suturing assembly in a retracted position, in accordance with embodiments of the invention.
Figure 37:
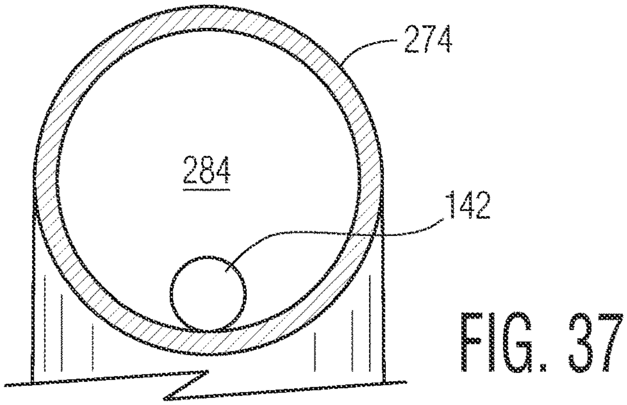
FIG. 37 is a cross sectional view along the cutting view 37-37 of FIG. 36, in accordance with embodiments of the invention.

Referring to FIGS. 36-37, in another embodiment, the curved suturing needle assembly 136 includes a single curved needle that is a hollow needle, and suture is threaded through the hollow needle. In such embodiment, the curved suturing needle assembly 136 includes a curved hollow needle body 274 having a proximal end 276 opposite a (pointed) distal end 278. The proximal end 276 of the curved hollow needle body defines a first orifice 280, for suture 142 to enter, as illustrated in FIG. 36. The distal end 278 of the curved hollow needle body 274 defines a second orifice 282, for the exit of the suture 142. As seen in FIG. 27, the curved hollow needle body 274 defines a passage 284 therethrough between the first orifice 280 and the second orifice 282, and the suture 142 is threaded through the first orifice 280, through the passage 284, and through the second orifice 282.

Figure 21:
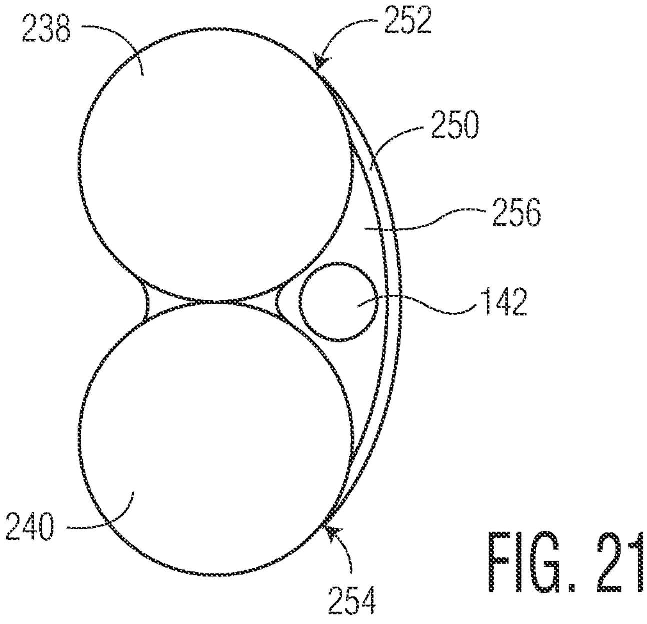
FIG. 21 is a cross sectional view along the cutting view 21-21 of FIG. 20, in accordance with embodiments of the invention.

As further embodied and described herein, there is provided a curved suturing needle assembly 136 having an outer curved needle 238 fixed to an inner curved needle 240. In one embodiment, the outer curved needle 238 is soldered to the inner curved needle 240, as illustrated in FIG. 21. In another embodiment, the outer curved needle 238 and the inner curved needle 240 are jointly fabricated by being cast in a single mold.

The outer curved needle 238 needle has a proximal end 242 opposite a distal end 244. The inner curved needle 240 has a proximal end 246 opposite a distal end 248. In a preferred embodiment, the disclosed curved suturing needle assembly 136 includes a shroud 250 disposed along an outer respective surface 252, 254 of the outer curved needle 238 and of the inner curved needle 240. The shroud forms a passage 256 for the suture 142. Preferably, the shroud 250 comprises a pointed cover 258 encapsulating the distal end 244 of the outer curved needle 238.

In yet another preferred embodiment, the disclosed curved suturing needle assembly 136 includes an elbow guide 260 disposed within the pointed cover 258 of the shroud 250. The elbow guide 260 is configured to engage and guide the suture 142 when the suture 142 extends outward from the distal end 248 of the inner curved needle. A filling 264 is preferably disposed within the pointed cover 258 of the shroud 250. The distal end 248 of the inner curved needle 240 preferably defines a ramp 262 adapted to engagingly guide the suture 142, to provide for a smooth exit for the suture 142 exiting the distal end 248 of the inner curved needle 240 of the curved suturing needle assembly 136.

Figure 51:
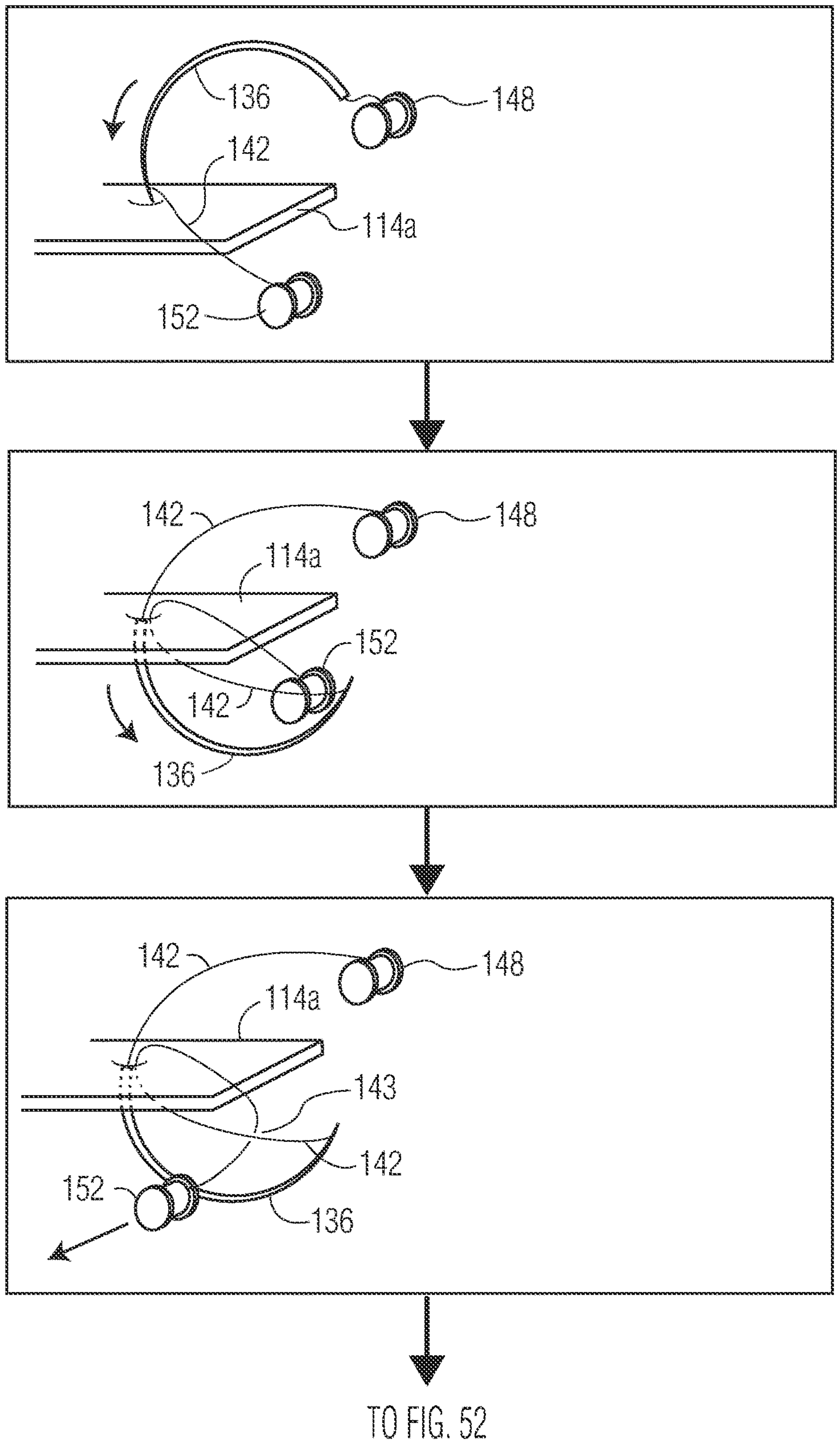
FIG. 51 is a partial cutaway view of a view of a curved suturing needle assembly of a handheld medical suturing device forming a bow with a suture, in accordance with embodiments of the invention.
Figure 52:
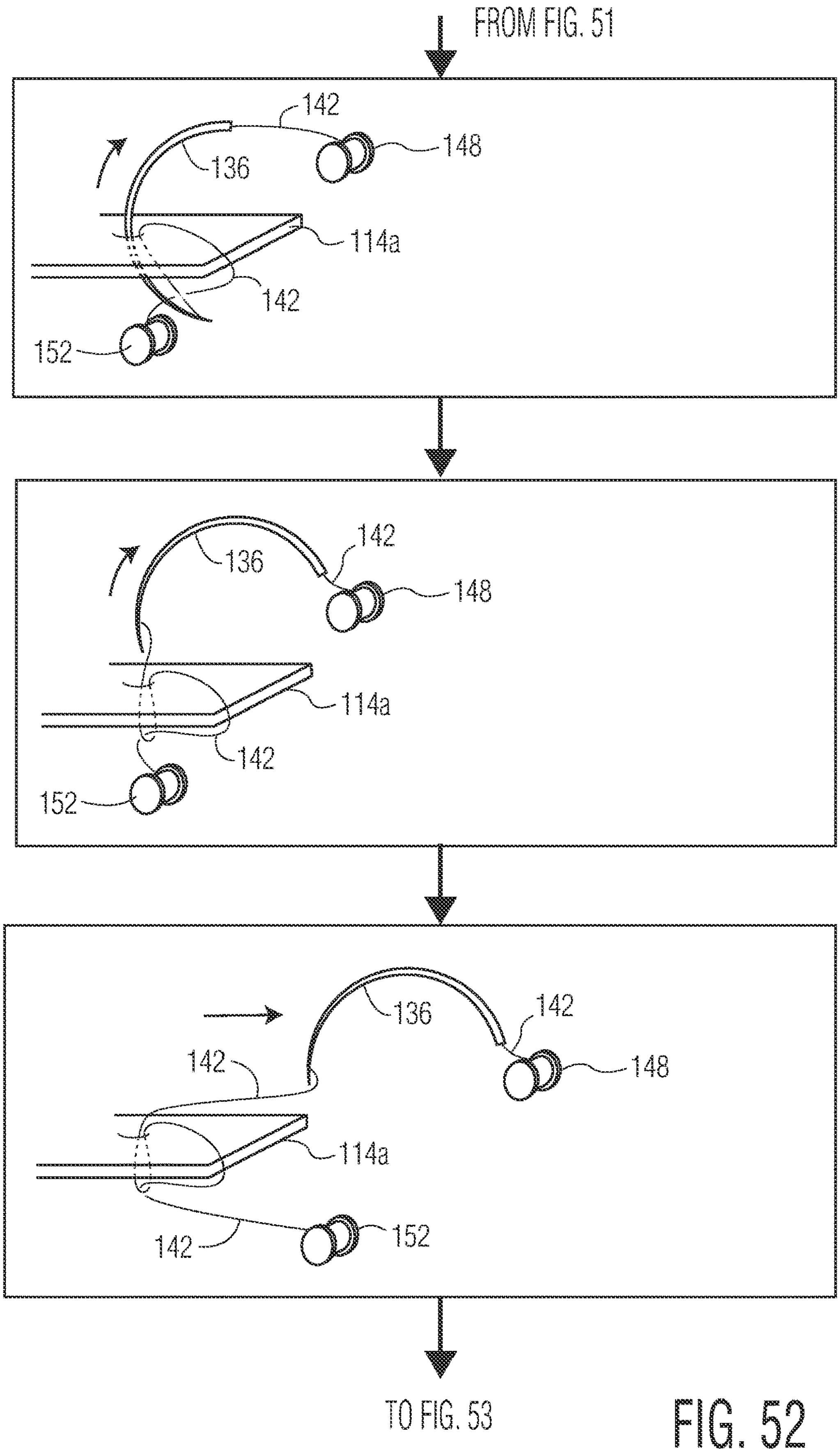
FIG. 52 is a partial cutaway view of a view of a curved suturing needle assembly of a handheld medical suturing device after forming a bow with a suture, with the curved suturing needle assembly in a retracted position, in accordance with embodiments of the invention.

FIGS. 41-55 illustrate the path of the suture and bobbin as the bobbin 152 moves side to side in the fixed bobbin channel 156. FIG. 51 illustrates the bobbin 152 forming a bow by crossing the XY plane and further illustrates the tying of a knot around the tissue 114. FIG. 52 illustrates the curved suturing needle assembly 136 of the handheld medical suturing device 100 completing the first knot around the first tissue **114*a* and moving to a second tissue 114*b*, as illustrated in FIG. 53**.

Figure 53:
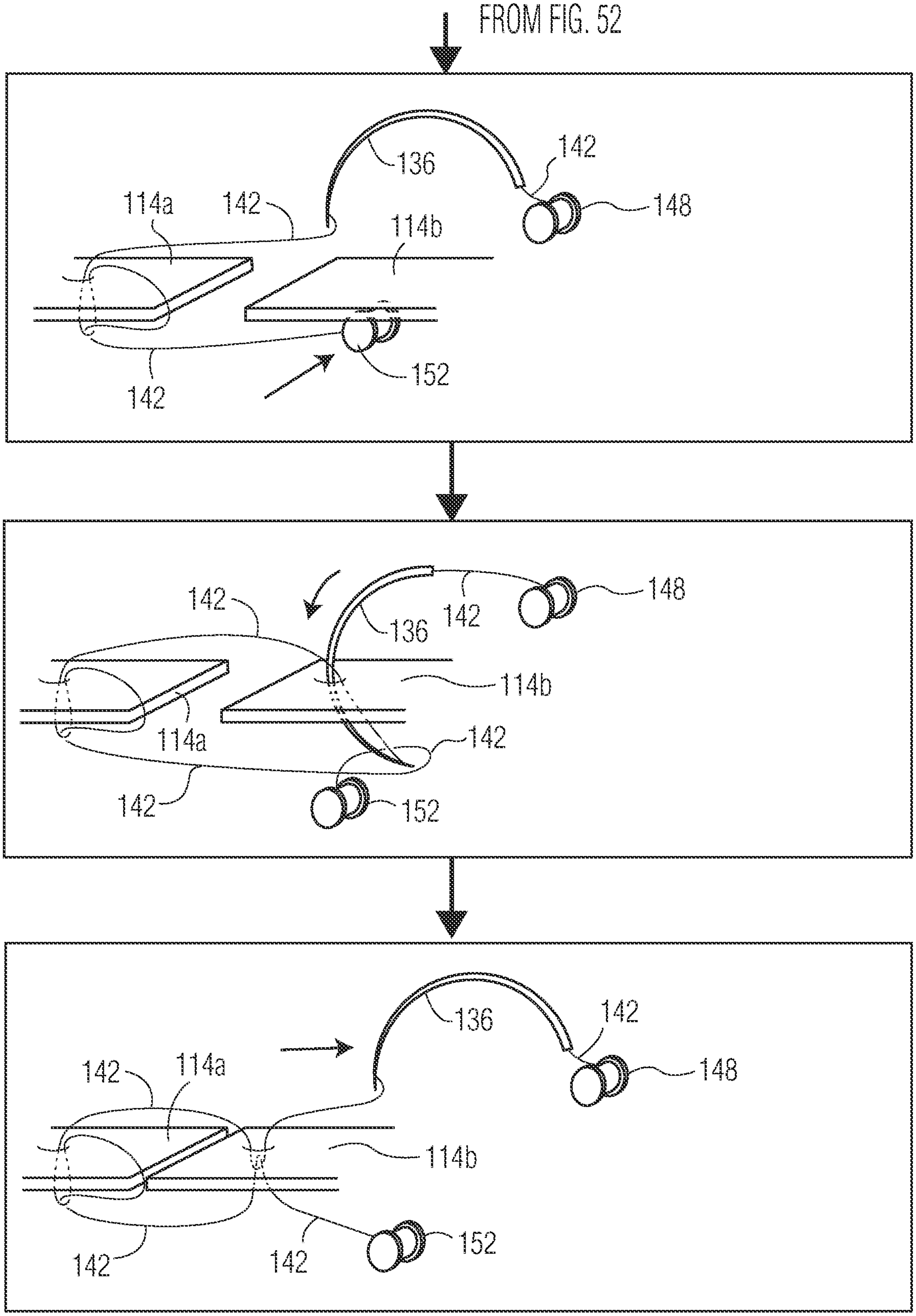
FIG. 53 is a partial cutaway view of a view of a curved suturing needle assembly of a handheld medical suturing device after forming a bow with a suture, with the curved suturing needle assembly in a retracted position, in a penetrated position through a second piece of tissue, and in a another rest position, in accordance with embodiments of the invention.

As illustrated in FIG. 53, embodiments of the handheld medical suturing device 100 of the disclosed invention locks the suture 142 at each interval, thereby providing an efficient manner of implementing continuous interlocking sutures, which lock at each interval, which provides for a stronger suture or stich between adjoining tissues (e.g., **114*a* and 114*b***), overcoming the problems associated with conventional running or continuous suturing techniques.

One or ordinary skill in the art can appreciate from this disclosure that embodiments of the disclosed invention can be fabricated at a small size such that such embodiments can also be used endoscopically and/or laparoscopically.

Non-robotic minimally invasive surgery is also known as endoscopic surgery, which is a minimally invasive procedure that utilizes an endoscope to reach internal organs through very small incisions. In other words, embodiments of the present disclosure can be used for endoscopic suturing or stitching through an access tube or the like, preferably at the end of an elongated shaft.

Laparoscopic surgery involves making several small incisions in the abdomen. Gas is then used to distend the abdomen, to create space for the operation. A surgeon uses a laparoscope, which has a video camera attached, to examine the area with visual references on a monitor. Specialized keyhole instruments are inserted to perform the operation. Embodiments of the present disclosure can be used for laparoscopic suturing or stitching with a laparoscope.

It is well known that a suture closure of the abdominal wound typically takes place at the end of a surgical procedure, and such procedure often takes several hours, depleting the surgeon of energy, which often causes the surgeon to be less precise with the closure technique utilized by the surgeon. As previously noted above, when smaller sutures (6 mm to 8 mm from the fascial wound edge) are placed more closely together to yield a suture-to-wound length ratio of 4:1 or greater, that cuts the incidence of incisional hernias by half. One reason why the recommendations for closely placed sutures are rarely followed is because that requires a substantial increase in the number of suture points. In other words, the recommended modifications of smaller, more numerous, and more closely placed suture points are rarely followed when a surgeon utilizes conventional suturing devices, because they demand more effort and time at a moment at the end of the surgery when the surgeon is tired from several hours of surgery.

As can been seen from the summary, description of the drawing figures, detailed description, and the figures herein, embodiments of the invention greatly facilitate the performance of the recommended improved technique of placing more closely spaced sutures by making the suturing process mostly automatic, as described in detail above, as the disclosed invention makes suturing much less labor intensive and makes the process much faster than conventional techniques, and thus the embodiments disclosed herein make the recommendations more likely to be adhered to.

Figure 19:
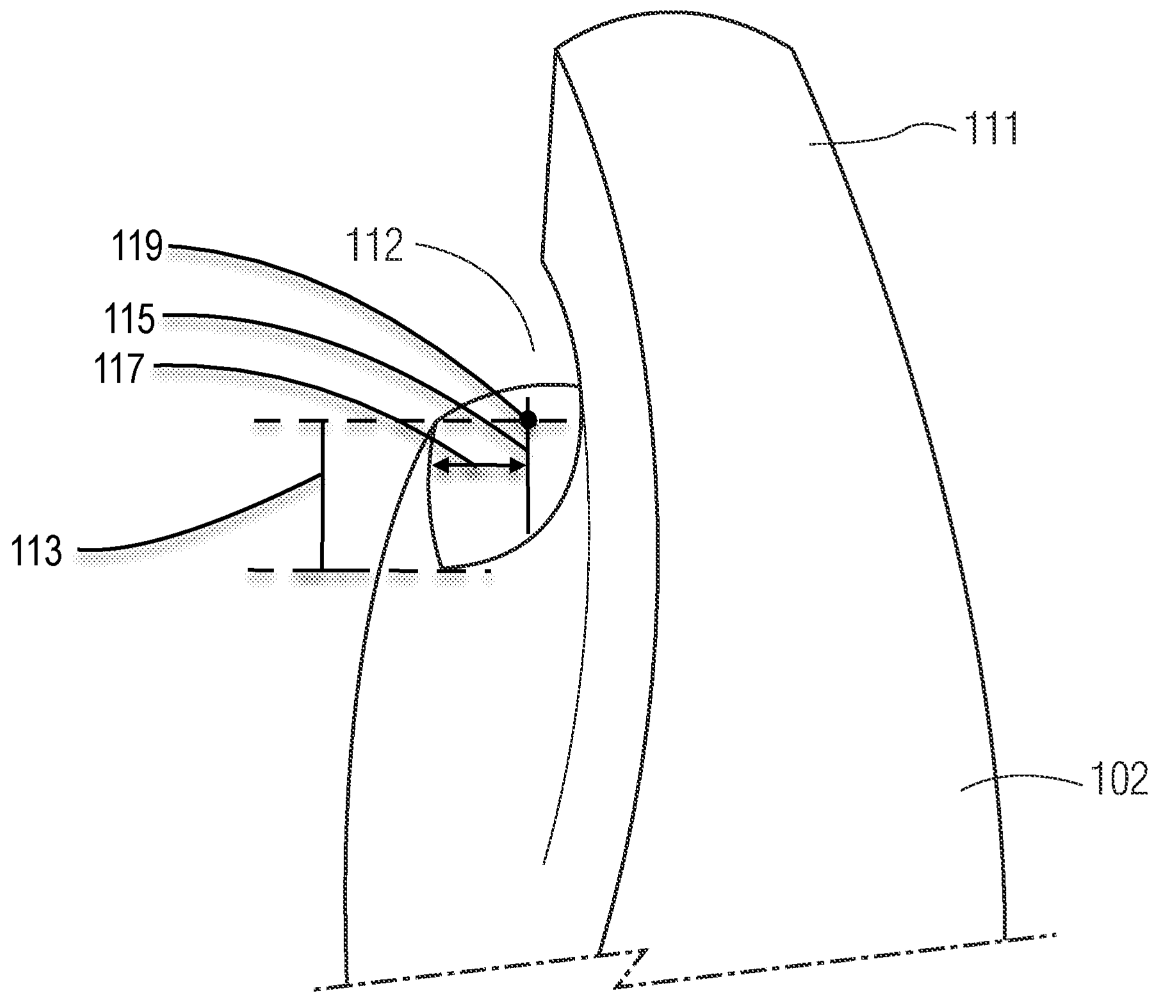
FIG. 19 is a top left perspective partial cutaway view of a handheld medical suturing device, in accordance with embodiments of the invention.
Figure 20:
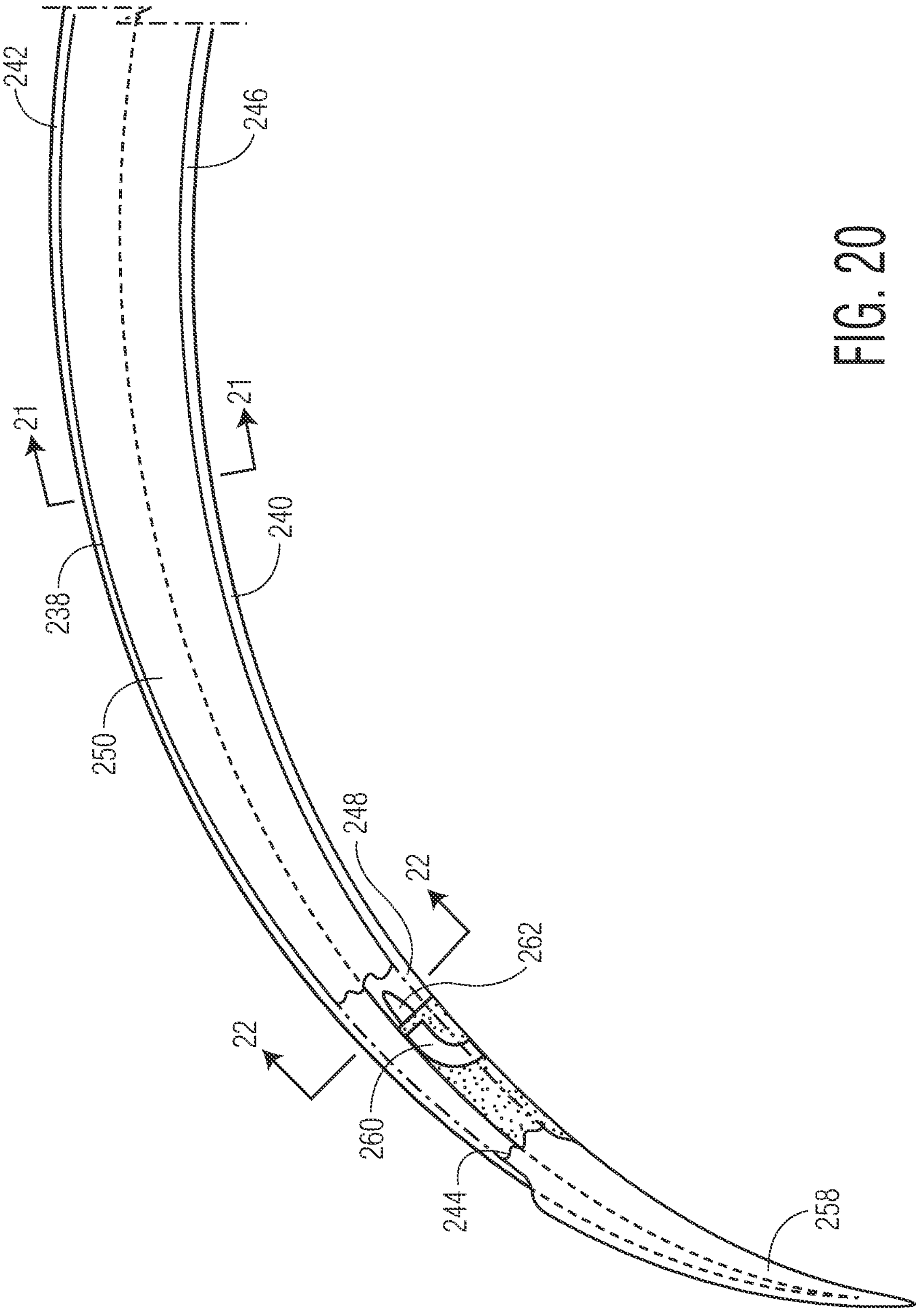
FIG. 20 is a partial cutaway cross-sectional view a curved needle suturing assembly, in accordance with embodiments of the invention.

Referring to FIGS. 1-3 and 19, the handheld medical suturing device 100 has a short opening 112 for a tissue bite 113, which as illustrated in FIG. 19, is preferably 6-8 mm between the back of the opening 112 of the handle body 102 and the puncture point 119, (where the curved needle suturing assembly 136 will penetrate the tissue). Such leads to the sutures (114, 114*a*, 114*b*) being automatically placed approximately 6 mm to 8 mm inside the wound edge, as is a preferred technique, as exemplified in FIG. 19, where the tissue bite distance 113 is preferably 6-8 mm.

The handheld medical suturing device 100 also preferably includes a simple visual aid 115 (preferably in the form of a line 115 in the opening 112) to measure the distance 117 between adjacent suture points, and such distance 117 preferably aligns with the centerline of the opening 112, as measured from the sidewall of the handle body 102, as illustrated in FIG. 19. The preferred distance 117 is 6-8 mm, and the distance 117 is most preferably 7 mm. In another preferred embodiment, additional measurements points (such as those inscribed or illustrated on a tape measure) are inscribed or illustrated within the opening 112 of the handheld medical suturing device 100 to assist the surgeon in measuring the distance between suture points. Thus, the handheld medical suturing device 100 better facilitates compliance with the recommendation for closeness between suture points in the tissue.

As can be appreciated from the disclosure herein, the handheld medical suturing device 100 provides a means to achieve the goal of preventing many incisional hernias by making the suturing process compliant with the recommendations in a faster, easier, more precise, and more repeatable manner, which is much more likely to be performed by the surgeon in light of the ease of use and semi-automatic nature of the handheld medical suturing device 100.

The handheld medical suturing device 100 uniquely adds stability to the wound (114*a*, 114*b*) by running an outer length of suture (one suture outside the wound) and contemporaneously running an inner length of suture (a suture inside the wound) simultaneously, as illustrated in FIGS. 50-53, along parallel axes. As such, it can be appreciated that the disclosed handheld medical suturing device 100 uniquely distributes the tension between these outer and inner lengths of suture, rather than just over a single suture as done conventionally.

A person's use of the handheld medical suturing device 100 is much more efficient than the current conventional method of continuous suturing, which requires numerous steps for each suture point, including, at least: (1) presentation of the needle, (2) clasping of the needle by the driver in the dominant hand, (3) stabilizing of the tissue by the non-dominant hand with a forceps, (4) perforation of the tissue by the clasped needle, (5) releasing the clasp on the needle, (6) rotating the user's hand to prepare for a re-clasping of the needle, (7) re-clasping the needle on the opposite surface of the tissue, (8) withdrawing the needle from such opposite surface of the tissue, and (9) repositioning the clasp on the needle, and (10) re-clasping the needle with the driver in preparation for perforation of the tissue again.

As disclosed in the preferred embodiments herein, the preferred handheld medical suturing device 100 requires provides for better and more efficient suturing, requiring less steps than conventional device methods, including: (1) stabilizing of the tissue 114 with a surgeon's non-dominant hand with a forceps, (2) squeezing the handle lever 108 of the handheld medical suturing device 100 to perforate the tissue 114, and (3) rotating the first thumb lever 200 (in the direction of Arrow F in FIG. 11) from the lever first position, as illustrated in FIGS. 2, 7, 8, 9, and 11, to the first thumb lever second position, as illustrated in FIGS. 10 and 12, and (4) releasing the handle lever 108 to withdraw the needle from the tissue 114 to lock the suture onto itself (i.e., tie a knot), as exemplified in FIGS. 44-52, and thereby form a locked suture. As can be appreciated from this disclosure, the preferred handheld medical suturing device 100 is comparatively simple in its construction and arrangement, strong, durable, efficient in its use, readily set up in operative position with respect to tissue or fabrics, and comparatively inexpensive to manufacture. The preferred handheld medical suturing device 100 is single use, meaning, it is preferably disposable of after being utilized to suture the tissue of a single patient.

Except as may be expressly otherwise indicated, the article "a" or "an" if and as used herein is not intended to limit, and should not be construed as limiting, the description or a claim to a single element to which the article refers. Rather, the article "a" or "an" if and as used herein is intended to cover one or more such elements, unless the text expressly indicates otherwise.

This invention is susceptible to considerable variation within the spirit and scope of the appended claims.

All U.S. patents and all publications identified herein are incorporated in their entirety by reference thereto.

The claimed invention is:

1. A handheld medical suturing device comprising:

a handle body having a hinge operatively connected to a distal end of a handle lever, the handle lever adapted to be grasped by a hand of a user, the handle body having a distal end which defines an opening adapted to receive tissue therein;

an actuating arm disposed within the handle body, the actuating arm having a proximal end and a distal end, the proximal end fixed to the distal end of the handle lever;

a constrained body disposed within the handle body, the constrained body having a proximal operatively connected to the actuating arm, and a distal end operatively connected to a pivoting radial arm;

the pivoting radial arm disposed within the handle body, the pivoting radial arm having a proximal end operatively connected to a fulcrum point disposed within the handle body, and a distal end operatively connected to the distal end of the constrained body;

a curved suturing needle assembly disposed within the handle body, the curved suturing needle assembly having a proximal end and a distal end, the proximal end operatively connected to the distal end of the pivoting radial arm, wherein the curved suturing needle assembly is adapted to advance a suture at least partially through the tissue along a suture path by a rotation of the actuating arm and the constrained body, thereby rotating the curved suturing needle assembly through the tissue between a retracted position and an extended position upon a pivoting of the handle lever relative to the handle body, wherein the curved suturing needle assembly is adapted to retract the suture along the suture path through the tissue from the extended position to the retracted position;

a bobbin channel having a semi-annular shaped body forming a bobbin channel cavity disposed within the distal end of the handle body, the semi-annular shaped body defining an elongated slot therethrough.

2. The handheld medical suturing device of claim 1, further comprising at least one spool of the suture disposed within an inner cavity passageway defined by the proximal end of the handle body, the suture threaded from the at least one spool through the inner cavity passageway to the curved suturing needle assembly, the suture threaded from the curved suturing needle assembly to a bobbin disposed within the distal end of the handle body, the at least one spool adapted to dispense the suture to the curved suturing needle assembly upon rotation of the curved suturing needle assembly from the retracted position to the extended position.

3. The handheld medical suturing device of claim 2, wherein the bobbin channel cavity has a central axis that is perpendicular to an XY plane and the semi-annular shaped body has a proximal end opposite a distal end.

4. The handheld medical suturing device of claim 3, further comprising a bobbin carrier movably fitted within the bobbin channel cavity of the bobbin channel, the bobbin carrier comprising a semi-annular shaped body forming a bobbin carrier cavity adapted to receive the curved suturing needle assembly in the extended position, the bobbin carrier adapted for movement of the bobbin along the central axis across the XY plane between a rest position and an actuated position, wherein the bobbin is rotatably disposed within the bobbin carrier cavity of the bobbin carrier.

5. The handheld medical suturing device of claim 4, wherein the bobbin carrier comprises a rack disposed along a bottom thereof, the rack operatively fitted within the elongated slot of the bobbin channel, wherein the handheld medical suturing device further comprises a spur gear fixed to a first drive axle, the first drive axle connected to a first thumb lever, wherein the spur gear operatively engages the rack to impart rotational motion of the-spur gear into linear motion of the rack from the rest position to the actuated position upon rotation of the first thumb lever from a first position to a second position.

6. The handheld medical suturing device of claim 5, wherein the bobbin has opposing hemispherical heads and a cylindrical body forming an axle disposed between the opposing hemispherical heads, the axle adapted to contain the suture between the opposing hemispherical heads, the cylindrical body adapted to release the suture therefrom upon movement of the bobbin carrier from the rest position to the actuated position, wherein movement of the bobbin carrier across the XY plane moves the suture through a bow formed by the suture extending from the curved suturing needle assembly.

7. The handheld medical suturing device of claim 5, further comprising at least one biasing member disposed within the inner cavity passageway of the handle body, the at least one biasing member positioned between and connected to the at least one spool and an inner wall of the proximal end of the handle body, the at least one biasing member tensioning the suture between the at least one spool and the bobbin.

8. The handheld medical suturing device of claim 5, further comprising a first spur gear concentrically disposed around and fixed to the first drive axle; and a second spur gear concentrically disposed around and fixed to a second drive axle, the second drive axle connected to a second thumb lever, wherein the first spur gear operatively engages the second spur gear.

9. The handheld medical suturing device of claim 5, further comprising at least one locking pin fixed to the first thumb lever, wherein the handle lever defines a channel, wherein with the handle lever in a squeezed position or in an open position, the at least one locking pin penetrates the channel upon rotation of the first thumb lever from the first position to the second position, wherein penetration of the channel is adapted to obstruct a second pivoting of the handle lever relative to the handle body from the squeezed position to the open position.

10. The handheld medical suturing device of claim 9, wherein the at least one locking pin is adapted for withdrawal from the channel upon rotation of the first thumb lever from the second position to the first position.

11. The handheld medical suturing device of claim 5, wherein the bobbin has a proximal end opposite a distal end, the proximal end comprising a first plurality of annularly disposed ridges adapted to provide a first frictional resistance against rotation of the bobbin relative to the bobbin carrier upon rotation of the curved suturing needle assembly through the tissue between the retracted position and the extended position upon the pivoting of the handle lever relative to the handle body.

12. The handheld medical suturing device of claim 11, wherein the distal end of the bobbin comprises a second plurality of annularly disposed ridges adapted to provide a second frictional resistance against rotation of the bobbin relative to the bobbin carrier upon rotation of the curved suturing needle assembly through the tissue between the retracted position and the extended position upon pivoting of the handle lever relative to the handle body.

13. The handheld medical suturing device of claim 4, wherein the curved suturing needle assembly further comprises an outer curved needle fixed to an inner curved needle, the outer curved needle having a proximal end opposite a distal end, the inner curved needle having a proximal end opposite a distal end; and a shroud disposed along an outer surface of the outer curved needle and the inner curved needle, the shroud forming a passage for the suture.

14. The handheld medical suturing device of claim 13, wherein the shroud comprises a pointed cover encapsulating the distal end of the outer curved needle.

15. The handheld medical suturing device of claim 14, further comprising an elbow guide disposed within the pointed cover, the elbow guide adapted to engagingly guide the suture when extending from the distal end of the inner curved needle.

16. The handheld medical suturing device of claim 15, wherein the distal end of the inner curved needle defines a ramp adapted to engagingly guide the suture.

17. The handheld medical suturing device of claim 15, further comprising a single length of suture, wherein a first portion of the single length of suture is disposed around the at least one spool, wherein a second portion of the single length of suture is disposed along the curved suturing needle assembly, wherein a third portion of the single length of suture is disposed inside the bobbin carrier cavity, and wherein a fourth portion of the single length of suture is disposed around the bobbin.

18. The handheld medical suturing device of claim 15, further comprising a single length of suture, wherein a first portion of the single length of suture is disposed around the at least one spool, wherein a second portion of the single length of suture is disposed within the shroud of the curved suturing needle assembly, wherein a third portion of the single length of suture is disposed inside the bobbin carrier cavity, and wherein a fourth portion of the single length of suture is disposed around the bobbin.

19. The handheld medical suturing device of claim 2, wherein the handheld medical suturing device further comprises at least one magnet disposed within a wall of a bobbin carrier, in a spaced relation to the bobbin, and wherein the bobbin comprises a ferrous material configured for a magnetic attraction adapted to provide a frictional resistance against rotation of the bobbin relative to the bobbin carrier.

20. The handheld medical suturing device of claim 1, further comprising at least one biasing member disposed around the hinge, the at least one biasing member operatively connected to the handle body and the distal end of the handle lever, the at least one biasing member pivotally biasing the proximal end of the handle lever away from the proximal end of the handle body.

21. The handheld medical suturing device of claim 1, further comprising at least one magnet disposed within a wall of the handle body; and at least one spool of the suture disposed within an inner cavity passageway defined by the proximal end of the handle body, wherein the at least one spool comprises a ferrous material adapted for a magnetic attraction to the at least one magnet configured to provide a frictional resistance against rotation of the at least one spool relative to the wall of the handle body.

22. The handheld medical suturing device of claim 1, wherein the curved suturing needle assembly further comprises a single curved needle having an inner surface which defines an annular groove, the single curved needle comprising a plurality of containment bridges annularly disposed along the annular groove of the inner surface, the plurality of containment bridges adapted to contain the suture.

23. The handheld medical suturing device of claim 1, wherein the curved suturing needle assembly further comprises a curved hollow needle body having a proximal end opposite a distal end, wherein the proximal end defines a first orifice and the distal end defines a second orifice, the curved hollow needle body defining a passage therethrough between the first orifice and the second orifice, and wherein the suture is threaded through the first orifice, the passage, and the second orifice.

* * * * *